United States Patent
Godwin et al.

(10) Patent No.: US 10,835,616 B2
(45) Date of Patent: *Nov. 17, 2020

(54) PROCESS FOR THE CONJUGATION OF A PEPTIDE OR PROTEIN WITH A REAGENT COMPRISING A LEAVING GROUP INCLUDING A PORTION OF PEG

(71) Applicant: POLYTHERICS LIMITED, Cambridge (GB)

(72) Inventors: Antony Godwin, Cambridge (GB); George Badescu, Cambridge (GB); Matthew Bird, Cambridge (GB); Penny Bryant, Cambridge (GB); David Morris, Cambridge (GB); Mark Frigerio, Cambridge (GB)

(73) Assignee: POLYTHERICS LIMITED, Cambridge (GB)

( * ) Notice: Subject to any disclaimer, the term of this patent is extended or adjusted under 35 U.S.C. 154(b) by 365 days.

This patent is subject to a terminal disclaimer.

(21) Appl. No.: 15/517,971

(22) PCT Filed: Oct. 8, 2015

(86) PCT No.: PCT/GB2015/052952
§ 371 (c)(1),
(2) Date: Apr. 10, 2017

(87) PCT Pub. No.: WO2016/059377
PCT Pub. Date: Apr. 21, 2016

(65) Prior Publication Data
US 2017/0304461 A1    Oct. 26, 2017

(30) Foreign Application Priority Data

Oct. 14, 2014 (GB) .................................. 1418186.1
Oct. 24, 2014 (GB) .................................. 1418984.9
Oct. 24, 2014 (GB) .................................. 1418986.4
Oct. 24, 2014 (GB) .................................. 1418989.8
May 27, 2015 (GB) .................................. 1509037.6

(51) Int. Cl.
| | |
|---|---|
| *A61K 47/68* | (2017.01) |
| *A61K 47/56* | (2017.01) |
| *A61K 47/00* | (2006.01) |
| *C07K 1/00* | (2006.01) |
| *C07K 1/10* | (2006.01) |
| *C07K 1/107* | (2006.01) |

(52) U.S. Cl.
CPC .......... *A61K 47/6803* (2017.08); *A61K 47/56* (2017.08); *A61K 47/6835* (2017.08); *A61K 47/6889* (2017.08); *C07K 1/107* (2013.01); *A61K 47/00* (2013.01); *C07K 1/00* (2013.01)

(58) Field of Classification Search
None
See application file for complete search history.

(56) References Cited

U.S. PATENT DOCUMENTS

| | | |
|---|---|---|
| 8,367,065 B2 | 2/2013 | Zhao et al. |
| 2002/0150548 A1 | 10/2002 | Harris |
| 2004/0204548 A1 | 10/2004 | Kozlowski et al. |
| 2006/0210526 A1 | 9/2006 | Brocchini et al. |
| 2010/0111866 A1 | 5/2010 | Kratz |
| 2010/0239517 A1 | 9/2010 | Brocchini et al. |
| 2011/0136723 A1 | 6/2011 | Godwin |
| 2012/0014905 A1 | 1/2012 | Godwin et al. |
| 2012/0190124 A1 | 7/2012 | Smith et al. |
| 2013/0338231 A1 | 12/2013 | Godwin et al. |
| 2016/0000933 A1 | 1/2016 | Polukhtin |
| 2016/0310612 A1 | 10/2016 | Lyon et al. |

FOREIGN PATENT DOCUMENTS

| | | |
|---|---|---|
| EP | 2260873 A1 | 12/2010 |
| WO | 99/45964 A1 | 9/1999 |
| WO | 2005/037992 A2 | 4/2005 |
| WO | 2005/042581 A2 | 5/2005 |
| WO | 2008/034124 A2 | 3/2008 |
| WO | 2011/077067 A1 | 6/2011 |
| WO | 2012/177837 A2 | 12/2012 |
| WO | 2013/173391 A1 | 11/2013 |
| WO | 2013/173392 A1 | 11/2013 |
| WO | 2013/173393 A1 | 11/2013 |
| WO | 2013/190272 A1 | 12/2013 |
| WO | 2013/190292 A2 | 12/2013 |
| WO | 2014/009774 A1 | 1/2014 |
| WO | 2014/064423 A1 | 5/2014 |
| WO | 2014/064424 A1 | 5/2014 |

(Continued)

OTHER PUBLICATIONS

Wu et al (Nature Biotechnology 23(9): 1137-1146, Sep. 2005).*
Yu et al (Investigative Ophthalmology & Visual Science 49(2): 522-527, Feb. 2008).*
Golay et al (Archives of Biochemistry and Biophysics 526: 146-153, 2012).*
Bouchard et al (Bioorganic and Medicinal Chemistry Letters 24: 5357-5363, 2014).*
Khalili et al. (Bioconjugate Chem. 2012, 23, p. 2262-2277).*
Balan et al. (Bioconjugate Chem. 2007, 18, p. 61-76).*

(Continued)

*Primary Examiner* — Samantha L Shterengarts
(74) *Attorney, Agent, or Firm* — Kilyk & Bowersox, P.L.L.C.

(57) ABSTRACT

The invention relates to novel conjugating reagents capable of reaction with at least one nucleophile present in a peptide or protein, which contain at least one leaving group which is lost on reaction with said nucleophile, in which the leaving group includes a portion —$(CH_2CH_2O)_n$—, in which n is a number of six or more; and novel processes for the preparation of conjugates containing peptides or proteins made using such reagents.

21 Claims, 6 Drawing Sheets

(56) References Cited

FOREIGN PATENT DOCUMENTS

| WO | 2014/184564 A1 | 11/2014 | |
|---|---|---|---|
| WO | WO 2015/057699 | * 4/2015 | ............. A61K 47/48 |

OTHER PUBLICATIONS

International Search Report and Written Opinion issued in corresponding International Patent Application No. PCT/GB2015/052952 dated Jan. 7, 2016 (14 pages).

Belcheva et al., "Synthesis and characterization of polymer-(multi)-peptide conjugates for control of specific cell aggregation," J. Biomater. Sci. Polymer Edn., 1998, vol. 9, No. 3, pp. 207-226.

Del Rosario et al., "Sulfhydryl Site-Specific Cross-Linking and Labeling of Monoclonal Antibodies by a Fluorescent Equilibrium Transfer Alkylation Cross-Link Reagent," Bioconjugate Chemistry, 1990, vol. 1, No. 1, pp. 51-59.

Krakert et al., "Adjustment of the bioresistivity by electron irradiation: self-assembled monolayers of oligo(ethyleneglycol)-terminated alkanethiols with embedded cleavable group," Physical Chemistry Chemical Physics, 2010, vol. 12, No. 2, pp. 507-515.

Liberatore et al., "Site-Directed Chemical Modification and Cross-Linking of a Monoclonal Antibody Using Equilibrium Transfer Alkylating Cross-Link Reagents," Bioconjugate Chemistry, 1990, vol. 1, No. 1, pp. 36-50, (12 pages).

Lyon, R.P., Seattle Genetics, "Novel ADC Chemistry for Improved Stability and Pharmacokinetics," Presentation (slide set believed to have been presented at Cambridge Healthtech Institute's 4th Annual Characterization of Biotherapeutics, on May 5, 2014), 25 pages.

Marculescu et al., "Aryloxymaleimides for cysteine modification, disulfide bridging and the dual functionalization of disulfide bonds," Chemical Communications, 2014, vol. 50, No. 54, pp. 7139-7142.

Schumacher et al., "In Situ Maleimide Bridging of Disulfides and a New Approach to Protein PEGylation," Bioconjugate Chemistry, 2011, vol. 22, pp. 132-136.

Smith et al., "Protein Modification, Bioconjugation, and Disulfide Bridging Using Bromomaleimides," J. Am. Chem. Soc., 2010, vol. 132, No. 6, pp. 1960-1965.

Marculescu, "Development of Novel Maleimide Reagents for Protein Modification," University College London, Aug. 2014, pp. 1-262.

\* cited by examiner

PROCESS FOR THE CONJUGATION OF A PEPTIDE OR PROTEIN WITH A REAGENT COMPRISING A LEAVING GROUP INCLUDING A PORTION OF PEG

This application is a National Stage Application of PCT/GB2015/052952, filed Oct. 8, 2015, which claims priority to United Kingdom Patent Application No. 1418186.1, filed Oct. 14, 2014, United Kingdom Patent Application No. 1418989.8, filed Oct. 24, 2014, United Kingdom Patent Application No. 1418986.4, filed Oct. 24, 2014, United Kingdom Patent Application No. 1418984.9, filed Oct. 24, 2014, and United Kingdom Patent Application No. 1509037.6, filed May 27, 2015.

FIELD OF INVENTION

This invention relates to a novel process for the conjugation of proteins and peptides, and to novel conjugating reagents.

BACKGROUND OF THE INVENTION

Much research has been devoted in recent years to the conjugation of a wide variety of payloads, for example diagnostic, therapeutic and labelling agents, to peptides and proteins for a wide range of applications. The protein or peptide itself may have therapeutic properties, and/or it may be a binding protein.

Peptides and proteins have potential use as therapeutic agents, and conjugation is one way of improving their properties. For example, water soluble, synthetic polymers, particularly polyalkylene glycols, are widely used to conjugate therapeutically active peptides or proteins. These therapeutic conjugates have been shown to alter pharmacokinetics favourably by prolonging circulation time and decreasing clearance rates, decreasing systemic toxicity, and in several cases, displaying increased clinical efficacy. The process of covalently conjugating polyethylene glycol, PEG, to proteins is commonly known as "PEGylation".

Binding proteins, particular antibodies or antibody fragments, are frequently conjugated. The specificity of binding proteins for specific markers on the surface of target cells and molecules has led to their extensive use either as diagnostic or therapeutic agents in their own right or as carriers for payloads which may include diagnostic and therapeutic agents. Such proteins conjugated to labels and reporter groups such as fluorophores, radioisotopes and enzymes find use in labelling and imaging applications, while conjugation to cytotoxic agents and chemotherapy drugs to produce antibody-drug conjugates (ADCs) allows targeted delivery of such agents to specific tissues or structures, for example particular cell types, minimising the impact on normal, healthy tissue and significantly reducing the side effects associated with chemotherapy treatments. Such conjugates have extensive potential therapeutic applications in several disease areas, particularly in cancer.

Many methods of conjugating proteins and peptides have been reported in the literature. For example, WO 95/13312 describes conjugation via a sulfone moiety. Probably the most commonly used process involves the use of conjugating reagents based on maleimides. Such reagents are described in many publications, for example WO 2004/060965. An alternative approach which leads to more homogeneous products is described by Liberatore et al, Bioconj. Chem 1990, 1, 36-50, and del Rosario et al, Bioconj. Chem. 1990, 1, 51-59, which describe the use of reagents which may be used to cross-link across the disulfide bonds in proteins, including antibodies. WO 2005/007197 describes a process for the conjugation of polymers to proteins, using novel conjugating reagents having the ability to conjugate with both sulfur atoms derived from a disulfide bond in a protein to give novel thioether conjugates, while WO 2009/047500 describes the use of the same conjugating reagents to bond to polyhistidine tags attached to the protein. WO 2010/010324 describes the use of monofunctional reagents capable of bonding to a single nucleophile in a protein. WO 2013/190292, WO 2014/064424, WO 2014/184564 and WO 2014/064423 all describe conjugation processes using various conjugation reagents.

The common feature of most conjugation processes is that the conjugation reaction involves the loss of a leaving group present in the conjugating reagent, and reaction of the resulting moiety with a nucleophile present in the protein. Reported leaving groups include groups of the type —SR, —OR, —$SO_2R$, —$OSO_2R$, —$N^+R_3$, —$N^+HR_2$, and —$N^+H_2R$, where R, where R is alkyl or aryl, and halogen.

Marculescu et al, Chem. Commun. 2014, 50, 7139-7142, discloses aryloxymaleimide conjugating reagents containing various leaving groups. Amongst other leaving groups, a group including MeO—$(CH_2CH_2O)_2$—$CH_2CH_2$— is disclosed. The same structure is disclosed in the PhD Thesis of Christina Marculescu, "Development of Novel Maleimide Reagents for Protein Modification", University College London, August 2014.

Surprisingly, we have now found that improved results can be obtained by replacing known leaving groups in known conjugating reagents by novel leaving groups which comprise a defined number of repeating units derived from ethylene glycol.

SUMMARY OF THE INVENTION

The present invention provides a process for the conjugation of a peptide or protein, which comprises reacting said peptide or protein with a conjugating reagent capable of reaction with at least one nucleophile present in said peptide or protein, said reagent containing at least one leaving group which is lost on reaction with said nucleophile; characterised in that said leaving group includes a portion —$(CH_2CH_2O)_n$— in which n is a number of six or more.

Conjugating reagents capable of reaction with at least one nucleophile present in a peptide or protein, which contain at least one leaving group which is lost on reaction with said nucleophile, characterised in that said leaving group includes a portion —$(CH_2CH_2O)_n$— in which n is a number of six or more, are novel, and the invention therefore provides such conjugating reagents per se.

In a further embodiment, the present invention provides a process for the conjugation of a peptide or protein, which comprises reacting said peptide or protein with a conjugating reagent capable of reaction with two nucleophiles in said peptide or protein, said reagent containing a leaving group which is lost on reaction with said nucleophiles, which has two points of attachment within the conjugating reagent, and which includes a portion —$(CH_2CH_2O)_{n1}$— in which n1 is a number of two or more. Conjugating reagents capable of reaction with two nucleophiles present in a peptide or protein, which contain a leaving group which is lost on reaction with said nucleophiles, and in which said leaving group has two points of attachment within the conjugating reagent and includes a portion —$(CH_2CH_2O)_{n1}$— in which n1 is a number of two or more, arc novel, and the invention therefore provides such conjugating reagents per se.

Throughout this Specification, peptides and proteins are jointly referred to as "protein" for convenience, and except where the context requires otherwise, a reference to "protein" should be understood to include a reference to both proteins and peptides.

DETAILED DESCRIPTION OF THE INVENTION

Leaving Groups

The present invention is based on the surprising finding that when reacting a conjugating reagent including at least one leaving group, with at least one nucleophile present in a protein, a group which includes a repeating unit —(CH$_2$CH$_2$O)$_n$— in which n is at least 6 or n1 is at least 2, acts as an improved leaving group compared with known leaving groups and, where n is at least six, compared with similar leaving groups having fewer repeating —(CH$_2$CH$_2$O)— units. The novel leaving group may for example include —(CH$_2$CH$_2$O)$_n$—R$^1$ where R$^1$ is a capping group. A very wide range of capping groups may be used. R$^1$ may for example be a hydrogen atom, an alkyl group, especially a C$_{1-4}$ alkyl group, particularly a methyl group, or an optionally substituted aryl group, for example an optionally substituted phenyl group, for example a tolyl group. Alternatively, the capping group may include a functional group such as a carboxyl group or an amine group. Such capping groups may for example have the formula —CH$_2$CH$_2$CO$_2$H or —CH$_2$CH$_2$NH$_2$, and may be prepared by functionalising the terminal unit of a —(CH$_2$CH$_2$O)$_n$— chain. Alternatively, rather than being terminated by a capping group, the —(CH$_2$CH$_2$O)$_n$— or —(CH$_2$CH$_2$O)$_{n1}$— group may have two points of attachment within the conjugating reagent such that chemically the equivalent of two leaving groups are present, capable of reacting with two nucleophiles.

The —(CH$_2$CH$_2$O)$_n$— or —(CH$_2$CH$_2$O)$_{n1}$— portion of the leaving group is based on PEG, polyethylene glycol. The PEG may be straight-chain or branched, and it may be derivatised or functionalised in any way. n is a number of 6 or more, for example 6, 7, 8, 9 or 10, or more. For example, n may be from 6 to 9. n1 is a number of 2 or more, for example 2, 3, 4, 5, 6, 7, 8, 9 or 10, or more. For example, n1 may be at least 4; or n1 may be at least 5, for example from 5 to 9; or n1 may be at least 6, for example from 6 to 9. There is no particular upper limit for n or n1. n or n1 may for example be 150 or less, for example 120 or less, for example 100 or less. For example n may be from 6 or 7 to 150, for example from 6 or 7 to 120, while n1 may be from 2, 3, 4, 5, 6 or 7 to 150, for example from 4, 5, 6 or 7 to 150, for example from 4, 5, 6 or 7 to 120. The PEG portion —(CH$_2$CH$_2$O)$_n$— or —(CH$_2$CH$_2$O)$_{n1}$— of a leaving group may for example have a molecular weight of from 1 to 5 kDa; it may for example be 1 kDa, 2 kDa. 3 kDa. 4 kDa or 5 kDa. A leaving group may if desired contain two or more portions —(CH$_2$CH$_2$O)$_n$— or —(CH$_2$CH$_2$O)$_{n1}$— separated by one or more spacers.

A leaving group in a conjugating reagent according to the invention is suitably of the formula —SP, —OP, —SO$_2$P, —OSO$_2$P, or —N$^+$PR$^2$R$^3$, in which P is a group which includes a portion —(CH$_2$CH$_2$O)$_n$— and each of R$^2$ and R$^3$ independently represents a hydrogen atom, a C$_{1-4}$alkyl group, or a group P. Leaving groups —N$^+$PR$^2$R$^3$ may be prepared by protonation or quaternisation of a group —NPR$^2$. Preferably each of R$^2$ and R$^3$ represents a C$_{1-4}$alkyl group, especially a methyl group, or, especially, a hydrogen atom. Alternatively, the conjugating reagent may include a group of formula —S—P—S—; —O—P—O—; —SO$_2$—P—SO$_2$—; —OSO$_2$—P—OSO$_2$—; and —N$^+$R$^2$R$^3$—P—N$^+$R$^2$R$^3$—, in which P is a group which includes a portion —(CH$_2$CH$_2$O)$_n$— or —(CH$_2$CH$_2$O)$_{n1}$—. As above, leaving groups —N$^+$R$^2$R$^3$—P—N$^+$R$^2$R$^3$— may be prepared by protonation or quaternisation of a group —NPR$^2$—P—NR$^2$. Specific groups of this type include —S—(CH$_2$CH$_2$O)$_n$—CH$_2$—CH$_2$—S—, —O—(CH$_2$CH$_2$O)$_n$—CH$_2$—CH$_2$—O—; —SO$_2$—(CH$_2$CH$_2$O)$_n$—CH$_2$—CH$_2$—SO$_2$—; —OSO$_2$—(CH$_2$CH$_2$O)$_n$—CH$_2$—CH$_2$—OSO$_2$—; or —N$^+$R$^2$R$^3$—(CH$_2$CH$_2$O)$_n$—CH$_2$—CH$_2$—N$^+$R$^2$R$^3$—, or the corresponding groups including n1 rather than n They can also include groups of the type:

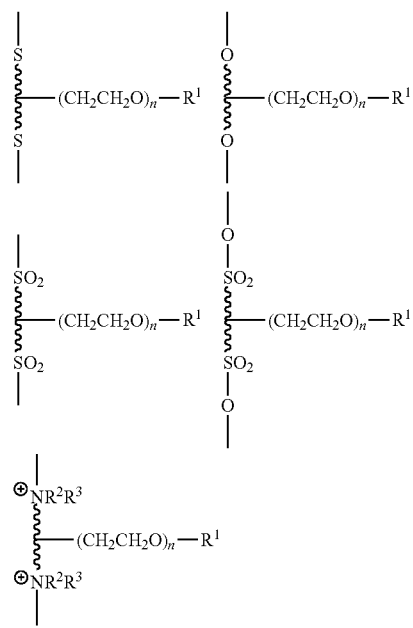

or the corresponding groups including n1 rather than n, where the —(CH$_2$CH$_2$O)$_n$— or —(CH$_2$CH$_2$O)$_{n1}$— group is carried by any suitable linking group, for example an alkylene group. These divalent groups are chemically equivalent to two leaving groups capable of reacting with two nucleophiles.

If two or more P groups are present, each P may be the same or different. Preferably the leaving group is of the formula —OSO$_2$—P—OSO$_2$—, for example —SO$_2$—(CH$_2$.CH$_2$O)$_{n1}$—CH$_2$—CH$_2$—SO$_2$—, or, especially, —SO$_2$P.

P may for example include a group of formula -T-(CH$_2$.CH$_2$O)$_n$— in which T is a linker. P may for example have the formula -T-(CH$_2$.CH$_2$O)$_n$—OR$^1$. T may for example be a direct bond, an alkyl group, for example a C$_{1-4}$alkyl group, or an optionally substituted aryl group, especially an optionally substituted phenyl group. The presence of a linker T which is a C$_{1-4}$alkyl group is often convenient because preparation of the conjugating reagent generally involves the use of a commercially-available PEG, and these are frequently terminated by a group which gives rise to a group T.

Conjugating Reagents

Many conjugating reagents which can be used to conjugate a payload to a protein are known, and the novel conjugating reagents of the invention differ from these known reagents in the nature of the leaving group(s) they contain. A conjugating reagent according to the invention must include at least one of the novel leaving groups according to the invention. It may include two or more leaving groups. If two or more novel leaving groups are present, these may be the same or different. For example, one leaving group may be a novel leaving group according to the invention, while another leaving group may be a conventional leaving group. If two or more novel leaving groups according to the invention are present, they may be the same or different, for example, they may contain portions in which each n is different. Alternatively, as mentioned above, a conjugating reagent may contain a single group which is chemically equivalent to two leaving groups and is capable of reacting with two nucleophiles.

In one preferred embodiment of the invention, the conjugating reagent contains two leaving groups according to the invention, or contains a single group which is chemically equivalent to two leaving groups and is capable of reacting with two nucleophiles, said reagent being capable of reacting with two thiol groups formed by reduction of a disulfide bond in a protein or peptide. Use of such reagents produces a conjugate by, effectively, bridging the disulfide bond in the protein or peptide.

One group of reagents is based on the bis-halo- or bis-thio-maleimides and derivatives thereof as described in Smith et al, J. Am. Chem. Soc. 2010, 132, 1960-1965, and Schumaker et al, Bioconj. Chem., 2011, 22, 132-136. These reagents contain the functional grouping:

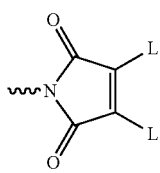

in which at least one, preferably each, L is a leaving group according to the invention. The nitrogen atom of the maleimide ring may carry a payload, for example a diagnostic, therapeutic or labelling agent, or a binding agent for a diagnostic, therapeutic or labelling agent, for example one of the formula D-Q-mentioned below. These reagents are capable of bridging a disulfide bond in a protein or peptide.

Similarly, maleimides containing a single leaving group L:

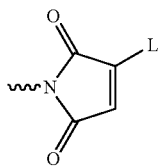

may be used. Again, the nitrogen atom of the maleimide ring may carry a payload, for example one of the formula D-Q-mentioned below.

In a preferred embodiment of the invention, the conjugating reagent contains the functional grouping:

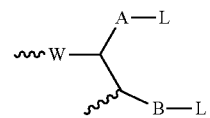

(I)

in which W represents an electron-withdrawing group, for example a keto group, an ester group —O—CO—, a sulfone group —SO$_2$—, or a cyano group; A represents a C$_{1-5}$ alkylene or alkenylene chain; B represents a bond or a C$_{1-4}$ alkylene or alkenylene chain; and either each L independently represents a leaving group, at least one of which, preferably both of which, must be a novel leaving group according to the invention, or both Ls together represent a leaving group according to the invention. Reagents of this type using conventional leaving groups are described in Bioconj. Chem 1990(1), 36-50, Bioconj. Chem 1990(1), 51-59, and J. Am. Chem. Soc. 110, 5211-5212. When reagents containing such groups react with proteins, a first leaving group L is lost to form in situ a conjugating reagent containing a functional grouping of formula:

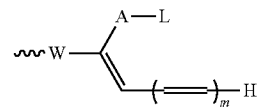

(I')

in which m is 0 to 4, which reacts with a first nucleophile. The second leaving group L is then lost, and reaction with a second nucleophile occurs. As an alternative to using a reagent containing the functional grouping I as starting material, reagents containing the functional grouping I' may be used as starting material.

Preferably W represents a keto group. Preferably A represents —CH$_2$— and B represents a bond.

Particularly preferred functional groupings of formula I and I' have the formulae:

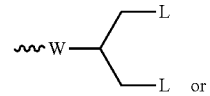

(Ia)

or

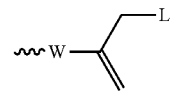

(Ia')

For example, the group may be of the formula:

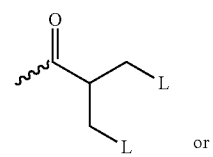

(Ib)

or

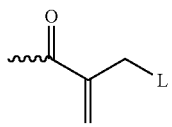

Another group of conjugating reagents contains the functional grouping:

~W—CR⁴R⁴'—CR⁴.L.L'     (II)

in which W has the meaning and the preferred meanings given above, and either
- each $R^4$ represents a hydrogen atom or a $C_{1-4}$alkyl group, $R^{R'}$ represents a hydrogen atom, and either each L independently represents a leaving group, at least one of which, preferably both of which, must be a novel leaving group according to the invention, or both Ls together represent a leaving group according to the invention; or
- each $R^4$ represents a hydrogen atom or a $C_{1-4}$alkyl group, L represents a leaving group according to the present invention, and $R^{4'}$ and L' together represent a bond.

Reagents containing the functional grouping I, I' or II are capable of bridging a disulfide bond in a protein or peptide.

Another group of conjugating reagents includes the functional grouping:

~W—(CH=CH)$_p$—(CH$_2$)$_2$-L     (III)

in which W has the meaning and preferred meanings given above and p represents 0 or an integer of from 1 to 4, preferably 0. An especially preferred reagent of this type includes the functional grouping:

~NH—CO—Ar—CO—(CH$_2$)$_2$-L     (IIIa)

in which Ar represents an optionally substituted aryl, especially phenyl, group.

Conjugating reagents according to the invention may contain more than one functional grouping for reaction with a protein. For example, a reagent may contain a functional grouping of formula I or I' at one end of the molecule, or any other functional grouping containing at least one novel leaving group according to the invention, and one or more additional functional groupings, either containing a novel leaving group according to the invention or being a conventional functional grouping capable of conjugating with a protein or any other molecule, elsewhere in the molecule. Such structures are described in for example Bcichcva et al, J. Biomatcr. Sci Polymer Edn. 9(3), 207-226 and arc useful in the synthesis of conjugates containing multiple proteins.

The novel conjugating reagents of the present invention may be prepared by methods analogous to known methods. For example, a molecule based on PEG and carrying an appropriate functionality may be introduced into a conjugating reagent in the same way that conventional leaving groups are introduced. For example, an amino or thiol-terminated PEG may be introduced into a compound containing a carbonyl group using the Mannich reaction. Specific reactions are illustrated in the Examples which follow.

Payloads

A conjugating reagent may carry a payload, for example a diagnostic, therapeutic or labelling agent, or a binding agent for a diagnostic, therapeutic or labelling agent. In this case, the reagents containing the unit of formula I/I' may have the formula (Ic) or (Ic') or, where W represents a cyano group, (Id) or (Id'):

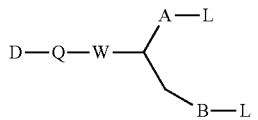

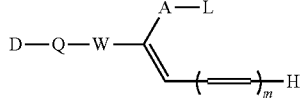

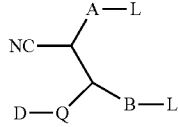

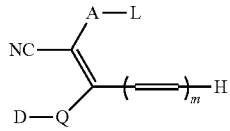

in which Q represents a linking group and D represents the payload, preferably a diagnostic, therapeutic or labelling agent, or a binding agent for a diagnostic, therapeutic or labelling agent. Preferably D-Q- includes a drug or a polymer or both a drug and a polymer. If a drug is present it may for example be a cytotoxic drug, and if a polymer is present, this is preferably polyethylene glycol.

If D represents a binding agent for a diagnostic, therapeutic or labelling agent, the preferred structure will of course depend on the structure of the diagnostic, therapeutic or labelling agent in the ultimately desired product. For example, any functional grouping capable of reacting with the diagnostic, therapeutic or labelling agent may be present. For example, functional groupings such as —CO$_2$H or a reactive derivative thereof, —NH$_2$, or —OH, may be present. Activated derivatives of carboxylic acid groups are well known in the art. For example, a carboxylic acid may be activated through the use of an activated ester such as an H-hydroxysuccinimide ester, or an acid halide. In one preferred embodiment, Q is an optionally substituted phenyl group, and D is a binding agent for a diagnostic, therapeutic or labelling agent, for example a —CO$_2$H, —NH$_2$, or —OH group.

Any suitable linking group Q may be used. In one embodiment, Q may for example be a direct bond, an alkylene group (preferably a $C_{1-10}$ alkylene group), or an optionally-substituted aryl or heteroaryl group, any of which may be terminated or (in the case of an alkylene group) interrupted by one or more oxygen atoms, sulfur atoms, —NR groups (in which R represents a hydrogen atom or an alkyl (preferably $C_{1-6}$alkyl), aryl (preferably phenyl), or alkyl-aryl (preferably $C_{1-6}$alkyl-phenyl) group), keto groups, —O—CO— groups, —CO—O— groups, —O—CO—O—, —O—CO—NR—, —NR—CO—O—, —CO—NR— and/or —NR.CO— groups. Such aryl and heteroaryl groups Q form one preferred embodiment of the invention. Suitable aryl groups include phenyl and naphthyl groups, while suitable heteroaryl groups include pyridine, pyrrole, furan, pyran, imidazole, pyrazole, oxazole, pyridazine, pyrimidine and purine. Especially suitable linking groups Q are heteroaryl or, especially, aryl groups, especially phenyl groups. Where D is a binding group, these may for example contain a —CO$_2$H, —NH$_2$, or —OH group as described above. Where D is a diagnostic, therapeutic or labelling agent, these may have a linking group to the group D, for example a group which is, or contains, a —NR.CO— or —CO.NR— group, for example an —NH.CO— or —CO.NH— group.

Specific groups D-Q- where D includes a binding group include the following:

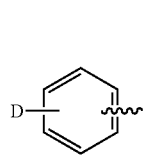 or 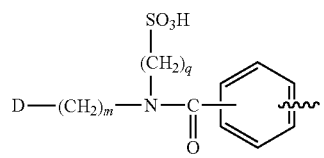

in which D represents a binding group, for example —CO₂H, —NH₂, or —OH, each of m and q represents an integer from 1 to 6, for example 2 or 3, and in which the phenyl ring may be unsubstituted or substituted by, for example, any of the substituents mentioned below.

Substituents which may be present on an optionally substituted aryl, especially phenyl, or heteroaryl group include for example one or more of the same or different substituents selected from alkyl (preferably $C_{1-4}$alkyl, especially methyl, optionally substituted by OH or CO₂H), —CN, —NO₂, —CO₂R, —COH, —CH₂OH, —COR, —OR, —OCOR, —OCO₂R, —SR, —SOR, —SO₂R, —NHCOR, —NRCOR, —NHCO₂R, —NR.CO₂R, —NO, —NHOH, —NR.OH, —C═N—NHCOR, —C═N—NR.COR, —N⁺R₃, —N⁺H₃, —N⁺HR₂, —N⁺H₂R, halogen, for example fluorine or chlorine, —C≡CR, —C═CR₂ and —C═CHR, in which each R independently represents a hydrogen atom or an alkyl (preferably $C_{1-6}$alkyl), aryl (preferably phenyl), or alkyl-aryl (preferably $C_{1-6}$alkyl-phenyl) group. The presence of electron withdrawing substituents is especially preferred. Preferred substituents include for example CN, NO₂, —OR, —OCOR, —SR, —NHCOR, —NR.COR, —NHOH and —NR.COR.

In another embodiment, a linker Q may contain a degradable group, i.e. it may contain a group which breaks under physiological conditions, separating D from the protein to which, ultimately, it will be bonded. Alternatively, Q may be a linker that is not cleavable under physiological conditions. Where a linker breaks under physiological conditions, it is preferably cleavable under intracellular conditions. Where the target is intracellular, preferably the linker is substantially insensitive to extracellular conditions (i.e. so that delivery to the intracellular target of a sufficient dose of the therapeutic agent is not prohibited).

Where Q contains a degradable group, this is generally sensitive to hydrolytic conditions, for example it may be a group which degrades at certain pH values (e.g. acidic conditions). Hydrolytic/acidic conditions may for example be found in endosomes or lysosomes. Examples of groups susceptible to hydrolysis under acidic conditions include hydrazones, semicarbazones, thiosemicarbazones, cis-aconitic amides, orthoesters and ketals. Examples of groups susceptible to hydrolytic conditions include:

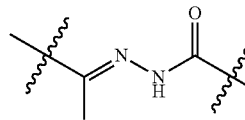 and 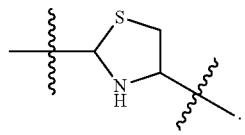

In a preferred embodiment, the linker is or includes

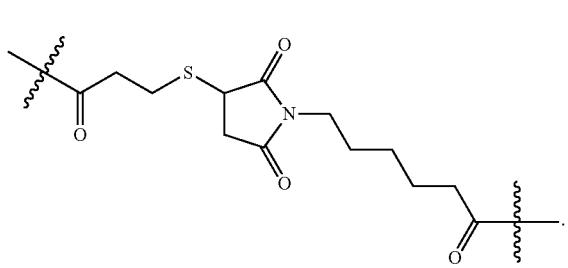 [SMILES: *C(=O)CCCCCN1C(=O)CC(SCCC(*)=O)C1=O]

For example, it may be or include:

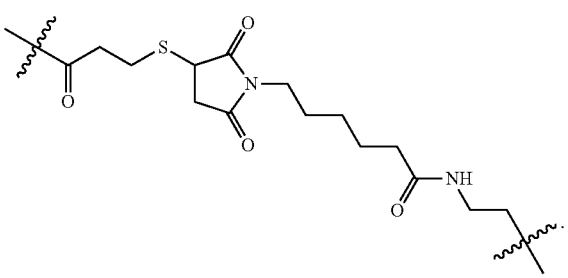 [SMILES: *CCNC(=O)CCCCCN1C(=O)CC(SCCC(*)=O)C1=O]

The linker Q may also be susceptible to degradation under reducing conditions. For example, it may contain a disulfide group that is cleavable on exposure to biological reducing agents, such as thiols. Examples of disulfide groups include:

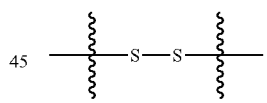 and 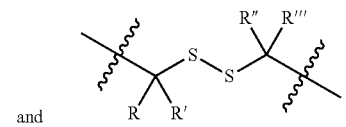

in which R, R', R" and R'" are each independently hydrogen or $C_{1-4}$alkyl. In a preferred embodiment the linker is or includes

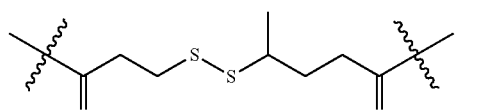

or

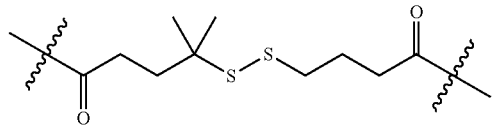

For example, it may be or include

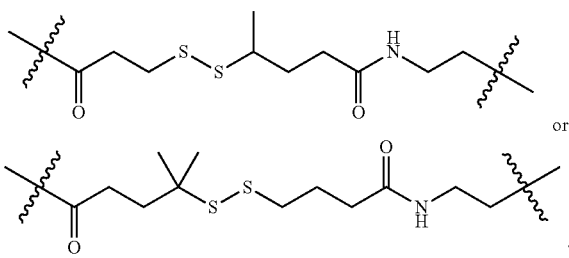

or

The linker Q may also contain a group which is susceptible to enzymatic degradation, for example it may be susceptible to cleavage by a protease (e.g. a lysosomal or endosomal protease) or peptidase. For example, it may contain a peptidyl group comprising at least one, for example at least two, or at least three amino acid residues (e.g. Phe-Leu, Gly-Phe-Leu-Gly, Val-Ala, Val-Cit, Phe-Lys). For example, it may be or include an amino acid chain having from 1 to 5, for example 2 to 4, amino acids. Another example of a group susceptible to enzymatic degradation is:

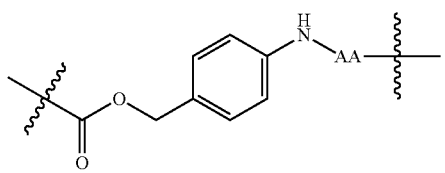

wherein AA represents a protease-specific amino acid sequence, such as Val-Cit.

In a preferred embodiment, the linker Q is or includes:

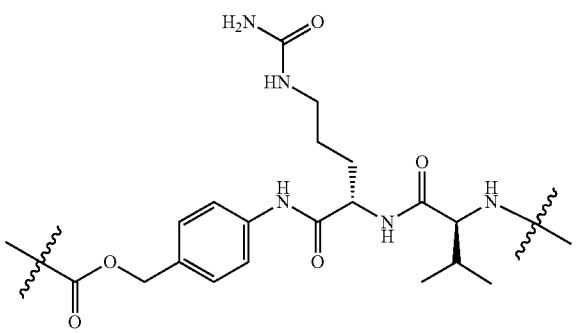 [SMILES: *N[C@H](C(=O)N[C@@H](CCCNC(N)=O)C(=O)Nc1ccc(COC(*)=O)cc1)C(C)C]

For example, it may be or include

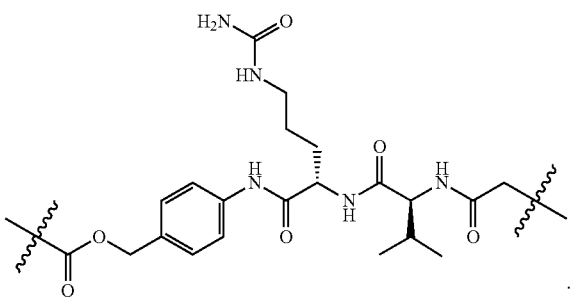 [SMILES: *CC(=O)N[C@H](C(=O)N[C@@H](CCCNC(N)=O)C(=O)Nc1ccc(COC(*)=O)cc1)C(C)C]

The linker Q may carry a single group D, or more than one group D. Multiple groups D may be incorporated by the use of a branching linker Q, which may for example incorporate an aspartate or glutamate or similar residue. This introduces a branching element of formula:

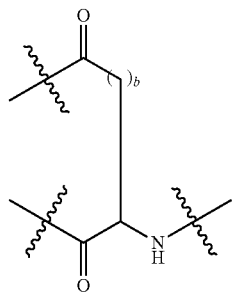

where b is 1, 2 or 3, b=1 being aspartate and b=2 being glutamate, and b=3 representing one preferred embodiment. Each of the acyl moieties in the above formula may be coupled to a group D. The branching group above may be incorporate a —CO.CH$_2$— group, thus:

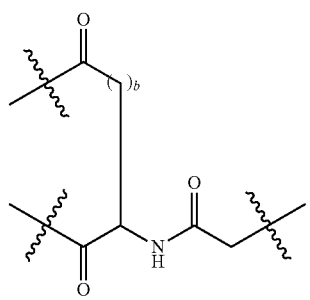

If desired, the aspartate or glutamate or similar residue may be coupled to further aspartate and/or glutamate and/or similar residues, for example:

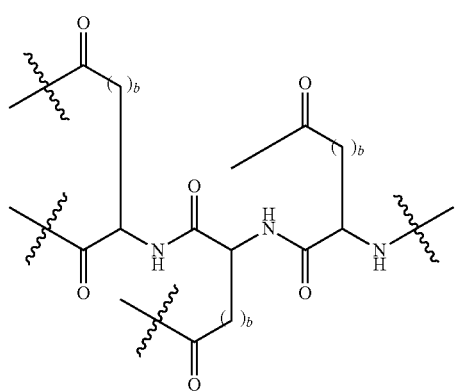

or

-continued

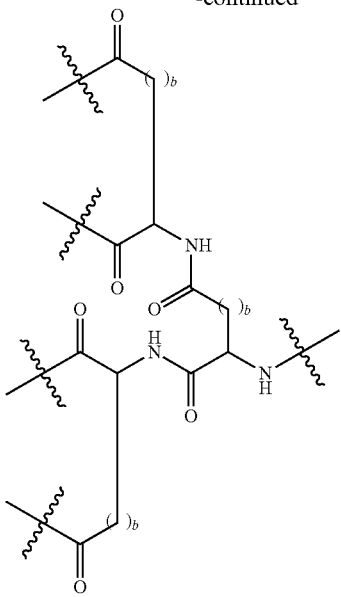

and so on.

All of the above linkers may be bonded to a polymer, for example via an amide bond. Polymers are discussed below.

Preferred reagents including the unit of formula I/I' include: or

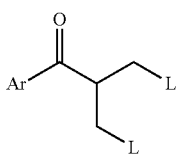
(Ie)

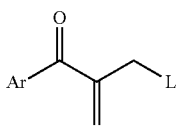
(Ie')

in which Q and D have the meanings given above.

A particularly preferred reagent of this type has the formula:

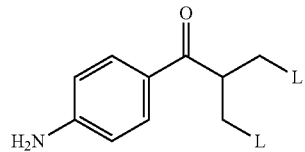
(If)

or

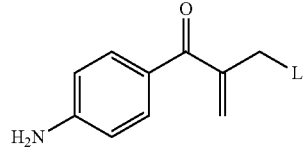
(If')

in which Ar represents an optionally-substituted aryl, especially phenyl, group, for example one of those listed above. For example, the reagent, or a precursor of the reagent, may be of the formula:

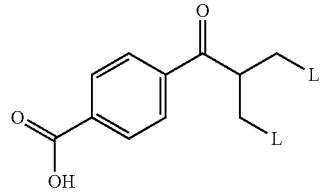
(Ig)

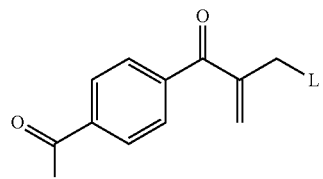
(Ig')

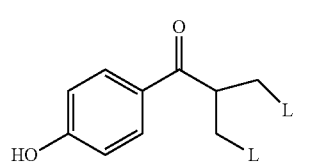
(Ih)

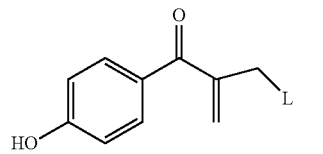
(Ih')

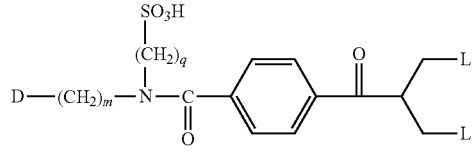
(Ii)

(Ii')

(Ij)

in which D is a —CO$_2$H, —NH$_2$ or —OH group, especially a —CO$_2$H group, and each of m and q is an integer from 1 to 6, for example 2 or 3. Preferably one of m and q is 2 and the other is 3.

The above reagents may be functionalised to carry any desired payload. For example, the NH$_2$ group shown in the formulae (Ig)/(Ig'), the carboxylic acid group in formulae (Ih)/(Ih') or the hydroxy group in formulae (Ii)/(Ii'), or the corresponding group D in the formula Ij above may be used to react with any suitable group in order to attach a payload, giving a compound in which the NH$_2$ group or carboxylic acid group becomes part of a further group D-Q-; or the aryl/phenyl group in the formulae (If), (If'), (Ig), (Ig'), (Ih), (Ih'), (Ii), (Ii') or (Ij) above may carry an additional suitable reactive group, which may be used to attach a payload.

Other preferred conjugating reagents carrying a payload have the formulae:

$$D\text{-}Q\text{-}W\text{—}CR^2R^{2'}\text{—}CR^2.L.L' \qquad (IIa)$$

or $$D\text{-}Q\text{-}(CH{=}CH)_p\text{—}(CH_2)_2\text{-}L \qquad (IIIa)$$

for example $$D\text{-}Q\text{-}NH\text{—}CO\text{—}Ar\text{—}CO\text{—}(CH_2)_2\text{-}L \qquad (IIIb)$$

in which the various substituents have the meanings and preferred meanings given above.

When D or Q incorporates a polymer, the conjugating reagent may be one of the reagents having the basic structure described in WO 99/45964, WO 2005/007197, or WO 2010/100430, the contents of which are incorporated herein by reference. Preferably a polymer-containing reagent contains a functional group of formula I as described above and is of the formula Ii below:

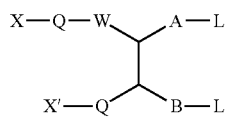
(Ii)

in which one of X and X' represents a polymer and the other represents a hydrogen atom;

Q represents a linking group;

W represents an electron-withdrawing group, for example a keto group, an ester group —O—CO— or a sulfone group —SO₂—; or, if X' represents a polymer, X-Q-W together may represent an electron withdrawing group, for example a cyano group;

A represents a $C_{1-5}$ alkylene or alkenylene chain;

B represents a bond or a $C_{1-4}$ alkylene or alkenylene chain; and each L independently represents a leaving group according to the present invention, or both Ls together represent a leaving group according to the invention.

Related conjugating reagents have the general formulae (Ii') or (IIa):

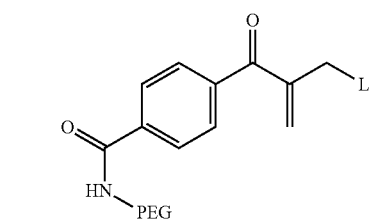
(Ii')

in which X, X', Q, W, A and L have the meanings given for the general formula Ii, and m represents 0 to 4; or $$X\text{-}Q\text{-}W\text{—}CR^4R^{4'}\text{—}CR^4.L.L' \qquad (IIa)$$

in which X, Q and W have the meanings given for the general formula Ii, and either each $R^4$ represents a hydrogen atom or a $C_{1-4}$alkyl group, $R^{4'}$ represents a hydrogen atom, and either each L independently represents a leaving group, at least one of which, preferably both of which, must be a novel leaving group according to the invention, or both Ls together represent a leaving group according to the invention; or each $R^4$ represents a hydrogen atom or a $C_{1-4}$alkyl group, L represents a leaving group according to the present invention, and $R^{4'}$ and L' together represent a bond.

Preferred meanings for the various substituents in formulae Ii, Ii' and IIa are as given above. In formulae Ii and Ii', preferably X represent a polymer, and X'-Q- represents a hydrogen atom. The linkage to the polymer X may be by way of a hydrolytically labile bond, or by a non-labile bond.

An especially preferred polymeric conjugating reagent has the formula:

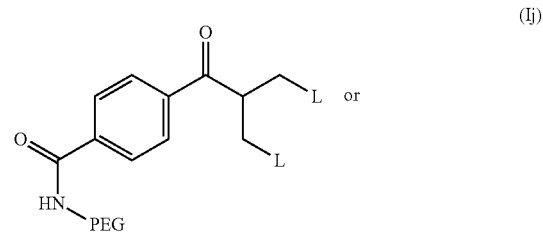

Another group of preferred reagents for use in the process of the invention is based on those described in WO 2010/010324. These reagents have the general formula:

$$X\text{-}[Q\text{-}W\text{—}(CH{=}CH)_p\text{—}(CH_2)_2\text{-}L]_q \qquad (IIIc)$$

in which X, Q, W and L have the meanings and preferred meanings given above; p represents 0 or an integer of from 1 to 4, preferably 0; and q represents an integer of from 1 to 8, preferably 1. An especially preferred reagent of the formula IIIc has the formula:

$$X\text{—}NH\text{—}CO\text{—}Ar\text{—}CO\text{—}(CH_2)_2\text{-}L \qquad (IIId)$$

In preferred embodiments of the above formulae, either the linker Q or the polymer X may incorporate a payload, for example a diagnostic, therapeutic or labelling agent. Particularly valuable are reagents of the above formulae in which either the linker Q or the polymer X incorporates a drug molecule: these reagents may be for example be used in the synthesis of antibody-drug conjugates.

Any desired payload, for example a diagnostic, therapeutic or labelling agent, or a binding agent for a diagnostic, therapeutic or labelling agent, may be included in the conjugating reagents according to the invention. The inclusion of one or more drug molecules, for example a cytotoxic agent or a toxin, is preferred. Auristatins and maytansinoids are typical cytotoxic drugs. It is often preferred that drug conjugates, particularly antibody drug conjugates, should contain multiple copies of the drug. Labelling agents (which should be understood to include imaging agents) may for example include a radionuclide, a fluorescent agent (for example an amine derivatised fluorescent probe such as 5-dimethylaminonaphthalene-1-(N-(2-aminoethyl))sulfonamide-dansyl ethylenediamine, Oregon Green® 488 cadaverine (catalogue number O-10465, Molecular Probes), dansyl cadaverine, N-(2-aminoethyl)-4-amino-3,6-disulfo-1,8-naphthalimide, dipotassium salt (lucifer yellow ethylenediamine), or rhodamine B ethylenediamine (catalogue number L-2424, Molecular Probes), or a thiol derivatised fluorescent probe for example BODIPY® FL L-cystine (catalogue number B-20340, Molecular Probes). A binding agent may for example be a chelating agent, for example desferrioxamine or biotin, which could then be used to bind any other desired moiety, for example one of those mentioned above, or it may be a reactive group as discussed above.

Our copending application GB 1418984 provides a conjugate comprising a protein, peptide and/or polymer attached to a maytansine-containing payload via a linker, a conjugating reagent useful in forming such conjugates and a maytansine-containing compound for use as payload. The maytansine-containing payloads and compounds consist of at least two maytansine moieties linked to each other through a non-degradable bridging group. These maytansines may be used as payloads in the present invention, and the reagents form one aspect of the present invention. Our copending application discloses the following:

"The present invention provides in a first aspect a maytansine-containing compound, in which at least two maytansine moieties (D) are linked to each other through a bridging group (Bd). The bridging group (Bd) is non-degradable under physiological conditions. Advantageously, the bridging group (Bd) has at least 3 chain carbon atoms and optionally contains poly(ethylene glycol) spacers in addition to the 3 chain carbon atoms. Advantageously, no two heteroatoms are adjacent to one another in the bridging group. Advantageously, the bridging group does not include the moiety: —C(O)—CH(NR$^1$X)—(CH$_2$)$_b$—C(O)—, where b is 1, 2 or 3, R$^1$ is selected from hydrogen and C$_1$ to C$_6$ alkyl, and X is any group. The maytansine-containing compound of the first aspect, in which two maytansine moieties are present, may be represented by the following formula (1):

D-Bd-D                                                                  (I)

In a second aspect, the invention provides a conjugating reagent, which contains a functional group capable of reaction with a peptide or protein and/or a functional group capable of reacting with a polymer, the payload being attached to the functional group(s) via one or more linkers, characterised in that the conjugation reagent comprises a maytansine-containing payload consisting of at least two maytansine moieties linked to each other through a non-degradable bridging group, with the proviso that when the conjugating reagent comprises a functional group capable of reaction with at a peptide or protein, the linker attaching the payload to the functional group capable of reaction with at a peptide or protein is degradable. When the conjugating reagent contains a functional group capable of reaction with at least one nucleophile present in a peptide or protein, the functional group including at least one leaving group which is lost on reaction with said nucleophile, the maytansinc-containing payload consisting of at least two maytansine moieties linked to each other through a non-degradable bridging group is advantageously attached to the functional group capable of reaction with at least one nucleophile present in a peptide or protein via a degradable linker. The conjugating reagent optionally contains a functional group capable of reaction with at least one nucleophile present in a peptide or protein, the functional group advantageously including at least one leaving group which is lost on reaction with said nucleophile, characterised in that the conjugation reagent comprises a maytansine-containing payload consisting of at least two maytansine moieties, especially two maytansine moieties, linked to each other through a non-degradable bridging group, and in that the payload is attached to the functional group capable of reaction with at least one nucleophile present in a peptide or protein via a linker, especially a degradable linker. The linker is suitable for linking the bridging group to a protein or peptide capable of binding to a partner or target. Preferably, the bridging group (Bd) of the maytansine-containing payload (D$_2$Bd) is connected to a degradable linker (Lk$^d$) that includes a degradable group which breaks under physiological conditions. The degradable group may, for example, be sensitive to hydrolytic conditions, especially acidic conditions; be susceptible to degradation under reducing conditions; or be susceptible to enzymatic degradation. The maytansine-containing conjugating reagent of the second aspect, in which two maytansine moieties are present, may be represented by the following formula (II):

D$_2$Bd-Lk-F                                                            (II)

in which D$_2$Bd represents a maytansine-containing payload consisting of two maytansine moieties linked to each other through a non-degradable bridging group, Lk is a linker, especially a degradable linker (Lk$^d$), and F represents a functional group capable of reaction with a peptide or protein and/or a functional group capable of reacting with a polymer.

The present invention further provides a process for the conjugation of a peptide, protein and/or a polymer, which comprises reacting said peptide, protein and/or a polymer with a conjugating reagent of the second aspect of the invention. When the conjugating reagent is reacted with a peptide or polymer, said conjugating reagent is advantageously capable of reaction with at least one nucleophile present in said peptide or protein, said reagent advantageously containing at least one leaving group which is lost on reaction with said nucleophile.

The invention also provides in a third aspect a conjugate comprising a protein, peptide and/or polymer attached to a maytansine-containing payload via a linker, characterised in that the maytansine-containing payload consists of at least two maytansine moieties linked to each other through a non-degradable bridging group. When the conjugate comprises a protein or peptide, the linker attaching the payload to the protein or peptide is advantageously degradable. The conjugate of the third aspect of the invention may, for example may, for example, comprise a maytansine-containing drug moiety (D$_2$Bd) linked via a linker (Lk), especially a degradable linker (Lk$^d$), to a protein or peptide (Ab) capable of binding to a partner or target, wherein the maytansine-containing drug moiety (D$_2$Bd) comprises at least two maytansine moieties (D) linked to each other through a non-degradable bridging group (Bd). A maytansine-containing conjugate of the third aspect of the invention, in which two maytansine moieties (D) are present, may be represented by the following formula (III):

D$_2$Bd-Lk-Ab                                                           (III)

The linker (Lk) is advantageously a degradable linker (Lk$^d$) that includes a degradable group which cleaves under physiological conditions separating the maytansine-containing drug moiety (D₂Bd) comprising at least two maytansine moieties (D) linked to each other through a bridging group (Bd) from the protein or peptide (Ab) capable of binding to a partner or target. The degradable group may, for example, be sensitive to hydrolytic conditions, especially acidic conditions; be susceptible to degradation under reducing conditions; or be susceptible to enzymatic degradation. The non-degradable bridging group (Bd) contains no groups that are susceptible to cleavage under the same conditions as those under which the degradable group in the degradable linker cleaves.

The maytansine-containing compound of the first aspect of the invention, may, for example, comprise or consist of at least two maytansine moieties (D), especially two maytansine moieties, linked to each other through a bridging group (Bd) having at least 3 chain carbon atoms, especially at least 7 chain carbon atoms, and optional poly(ethylene glycol) units in addition to the chain carbon atoms, with the proviso that no two heteroatoms are adjacent to one another in the bridging group and with the proviso that the bridging group does not include the moiety: —C(O)—CH(NR¹X)—(CH₂)$_b$—C(O)—, where b is 1, 2 or 3, R¹ is selected from hydrogen and C₁ to C₆ alkyl, and X is any group. Optionally, the bridging group incorporates from 0 to 8 carbonyl groups, especially from 2 to 8 carbonyl groups. The bridging group optionally incorporates from 0 to 4 unsaturated carbon-carbon double bonds; and/or from 0 to 4 C₃ to C₁₀ aryl or heteroaryl groups in the chain. Optionally, the chain is interspersed with from 0 to 11, especially from 2 to 11, chain heteroatoms selected from N, O and S, with the proviso that no two heteroatoms are adjacent to one another.

Advantageously, a chain carbon atoms in the bridging group is substituted with a pendant connecting group selected from amine, carboxy, alkyne, azide, hydroxyl or thiol. Advantageously the bridging group includes at least one amide linkage in the chain."

Use of the present invention enables efficient conjugation of a very wide range of payloads. Yields obtained using known technologies can be low for some payloads. For example, conjugation of proteins to payloads which do not contain PEG can be low-yielding, and use of the present invention can give higher yields. Further, conjugation may occur significantly more rapidly and hence more efficiently than when using known technologies.

Polymers Present in the Conjugating Reagents

As mentioned above, the conjugating reagent may be used to conjugate an oligomer or a polymer (jointly referred to herein as "polymer" for convenience), especially a water soluble, synthetic polymer, particularly polyalkylene glycol, to a protein. In other words, the payload (for example D or X in the above general formulae) may be, or may include, a polymer. A polymer may for example be a polyalkylene glycol, a polyvinylpyrrolidone, a polyacrylate, for example polyacryloyl morpholine, a polymethacrylate, a polyoxazoline, a polyvinylalcohol, a polyacrylamide or polymethacrylamide, for example polycarboxymethacrylamide, or a HPMA copolymer. Additionally, the polymer may be a polymer that is susceptible to enzymatic or hydrolytic degradation. Such polymers, for example, include polyesters, polyacetals, poly(ortho esters), polycarbonates, poly(imino carbonates), and polyamides, such as poly(amino acids). A polymer may be a homopolymer, random copolymer or a structurally defined copolymer such as a block copolymer, for example it may be a block copolymer derived from two or more alkylene oxides, or from poly(alkylene oxide) and either a polyester, polyacetal, poly(ortho ester), or a poly (amino acid). Polyfunctional polymers that may be used include copolymers of divinylether-maleic anhydride and styrene-maleic anhydride.

Naturally occurring polymers may also be used, for example polysaccharides such as chitin, dextran, dextrin, chitosan, starch, cellulose, glycogen, poly(sialylic acid), hyaluronic acid and derivatives thereof. A protein may be used as the polymer. This allows conjugation to the first protein, for example an antibody or antibody fragment, of a second protein, for example an enzyme or other active protein, or a scaffolding protein such as avidin that can bind to biotinylated molecules. Also, if a peptide containing a catalytic sequence is used, for example an O-glycan acceptor site for glycosyltransferase, it allows the incorporation of a substrate or a target for subsequent enzymatic reaction. Polymers such as polyglutamic acid may also be used, as may hybrid polymers derived from natural monomers such as saccharides or amino acids and synthetic monomers such as ethylene oxide or methacrylic acid.

If the polymer is a polyalkylene glycol, this is preferably one containing C₂ and/or C₃ units, and is especially a polyethylene glycol. A polymer, particularly a polyalkylene glycol, may contain a single linear chain, or it may have branched morphology composed of many chains either small or large. The so-called Pluronics are an important class of PEG block copolymers. These are derived from ethylene oxide and propylene oxide blocks. Substituted, or capped, polyalkylene glycols, for example methoxypolyethylene glycol, may be used.

The polymer may, for example, be a comb polymer produced by the method described in WO 2004/113394, the contents of which are incorporated herein by reference. For example, the polymer may be a comb polymer having a general formula:

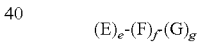

where:
E, where present, is obtainable by additional polymerisation of one or more olefinically unsaturated monomers which are not as defined in F;
F is obtainable by additional polymerisation of a plurality of monomers which are linear, branched, or star-shaped, substituted or non-substituted, and have an olefinically unsaturated moiety;
G, where present, is obtainable by additional polymerisation of one or more olefinically-unsaturated monomers which are not as defined in F;
e and g are an integer between 0 and 500;
f is an integer of 0 to 1000;
wherein at least one of D, E and F is present.

A polymer for conjugation to a protein may optionally be derivatised or functionalised in any desired way. In one preferred embodiment, the polymer carries, for example, a diagnostic agent, a therapeutic agent, or a labelling agent, for example one of those mentioned above, or a binding agent capable of binding a diagnostic agent, a therapeutic agent, or a labelling agent. Reactive groups may be linked at the polymer terminus or end group, or along the polymer chain through pendent linkers; in such case, the polymer is for example a polyacrylamide, polymethacrylamide, polyacrylate, polymethacrylate, or a maleic anhydride copolymer. Multimeric conjugates that contain more than one biological molecule, can result in synergistic and additive benefits. If desired, the polymer may be coupled to a solid support using conventional methods.

The optimum molecular weight of the polymer will of course depend upon the intended application. Long-chain polymers may be used, for example the number average molecular weight may be up to around 75,000, for example up to 50,000, 40,000 or 30,000 g/mole. For example, the number average molecular weight may be in the range of from 500 g/mole to around 75,000 g/mole. However, very small oligomers, consisting of discrete PEG chains with, for example, as few as 2 repeat units, for example from 2 to 50 repeat units, are useful for some applications, and are present in one preferred embodiment of the invention. For example, the polymer may contain from 2 to 48, for example from 2 to 36, for example from 2 to 24, units may be used. Straight chain or branched PEGs with 12, 20, 24, 36, 40 or 48 repeat units may for example be used. When the protein to be conjugated is intended to leave the circulation and penetrate tissue, for example for use in the treatment of inflammation caused by malignancy, infection or autoimmune disease, or by trauma, it may be advantageous to use a lower molecular weight polymer in the range up to 30,000 g/mole. For applications where the polymer-protein conjugate is intended to remain in circulation it may be advantageous to use a higher molecular weight polymer, for example in the range of 20,000-75,000 g/mole.

The polymer to be used should be selected so the conjugate is soluble in the solvent medium for its intended use. For biological applications, particularly for diagnostic applications and therapeutic applications for clinical therapeutic administration to a mammal, the conjugate will be soluble in aqueous media.

Preferably the polymer is a synthetic polymer, and preferably it is a water-soluble polymer. The use of a water-soluble polyethylene glycol is particularly preferred for many applications.

Our copending application GB 1418986 relates to the use of PEG-containing linkers of a particular structure, and these may be used in the present invention. That application discloses the following:

"The invention provides a conjugate of a protein or peptide with a therapeutic, diagnostic or labelling agent, said conjugate containing a protein or peptide bonding portion and a polyethylene glycol portion; in which said protein or peptide bonding portion has the general formula:

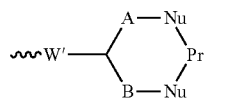
(I)

in which Pr represents said protein or peptide, each Nu represents a nucleophile present in or attached to the protein or peptide, each of A and B independently represents a $C_{1-4}$alkylene or alkenylene chain, and W' represents an electron withdrawing group or a group obtained by reduction of an electron withdrawing group; and in which said polyethylene glycol portion is or includes a pendant polyethylene glycol chain which has a terminal end group of formula —$CH_2CH_2OR$ in which R represents a hydrogen atom, an alkyl group, for example a $C_{1-4}$alkyl group, especially a methyl group, or an optionally substituted aryl group, especially a phenyl group, especially an unsubstituted phenyl group.

The invention also provides a conjugating reagent capable of reacting with a protein or peptide, and including a therapeutic, diagnostic or labelling agent and a polyethylene glycol portion; said conjugating reagent including a group of the formula:

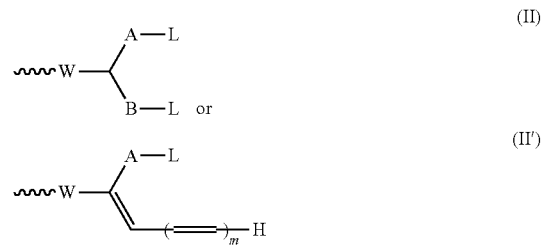

in which W represents an electron withdrawing group, A and B have the meanings given above, m is 0 to 4, and each L independently represents a leaving group; and in which said polyethylene glycol portion is or includes a pendant polyethylene glycol chain which has a terminal end group of formula —$CH_2CH_2OR$ in which R represents a hydrogen atom, an alkyl group, for example a $C_{1-4}$alkyl group, especially a methyl group, or an optionally substituted aryl group, especially a phenyl group, especially an unsubstituted phenyl group.

The invention also provides a process for the preparation of a conjugate according to the invention, which comprises reacting a protein or peptide with a conjugating reagent according to the invention.

The conjugate of the invention may be represented schematically by the formula:

(III)

in which D represents the therapeutic, diagnostic or labelling agent, F' represents the group of formula I, and PEG represents the pendant polyethylene glycol chain having a terminal end group of formula —$CH_2CH_2OR$.

The reagent of the invention may be represented schematically by the formula:

(IV)

in which D represents the therapeutic, diagnostic or labelling agent, F represents the group of formula II or II', and PEG represents the pendant polyethylene glycol chain having a terminal end group of formula —$CH_2CH_2OR$. The functional grouping F is capable of reacting with two nucleophiles present in a protein or peptide as explained below.

A polyethylene glycol (PEG) portion of the conjugates and reagents of the invention is or includes a pendant PEG chain which has a terminal end group of formula —CH$_2$CH$_2$OR in which R represents a hydrogen atom, an alkyl group, for example a C$_{1-4}$alkyl group, especially a methyl group, or an optionally substituted aryl group, especially a phenyl group, especially an unsubstituted phenyl group. Preferably R is a methyl group or a hydrogen atom.

The overall size of the PEG portion will of course depend on the intended application. For some applications, high molecular weight PEGs may be used, for example the number average molecular weight may be up to around 75,000, for example up to 50,000, 40,000 or 30,000 g/mole. For example, the number average molecular weight may be in the range of from 500 g/mole to around 75,000. However, smaller PEG portions may be preferred for some applications.

In one preferred embodiment, all of the PEG in the PEG portion is present in the pendant PEG chain. In another embodiment, PEG may also be present in the backbone of the molecule, and this is discussed in more detail below.

As with the PEG portion, the size of the pendant PEG chain will depend on the intended application. For some applications, high molecular weight pendant PEG chains may be used, for example the number average molecular weight may be up to around 75,000. for example up to 50,000, 40,000 or 30,000 g/mole. For example, the number average molecular weight may be in the range of from 500 g/mole to around 75,000. However, for many applications, smaller pendant PEG chains may be used.

For example said PEG chain may have a molecular weight up to 3,000 g/mole. However, very small oligomers, consisting of discrete PEG chains with, for example, as few as 2 repeat units, for example from 2 to 50 repeat units, are useful for some applications, and are present as said PEG chain in one preferred embodiment of the invention. The pendant PEG chain may be straight-chain or branched. PEG chains, for example straight-chain or branched chains with 12, 20, 24, 36, 40 or 48 repeat units may for example be used."

Conjugation Processes

Conjugating reagents containing a leaving group according to the invention may be reacted with a protein or peptide to form a conjugate, and such a reaction forms a further aspect of the invention. In a preferred embodiment of this aspect of the invention, a conjugating reagent having one of the structures I, I', II or III described above (including all of the preferred sub-structures) is reacted with a protein or peptide to form a conjugate. The immediate product of the conjugation process using one of these reagents is a conjugate which contains an electron-withdrawing group W. However, the conjugation process is reversible under suitable conditions. This may be desirable for some applications, for example where rapid release of the protein is required, but for other applications, rapid release of the protein may be undesirable. It may therefore be desirable to stabilise the conjugates by reduction of the electron-withdrawing moiety W to give a moiety which prevents release of the protein. Accordingly, the process described above may comprise an additional optional step of reducing the electron withdrawing group W in the conjugate. The use of a borohydride, for example sodium borohydride, sodium cyanoborohydride, potassium borohydride or sodium triacetoxyborohydride, as reducing agent is particularly preferred. Other reducing agents which may be used include for example tin(II) chloride, alkoxides such as aluminium alkoxide, and lithium aluminium hydride.

Thus, for example, a moiety W containing a keto group may be reduced to a moiety containing a CH(OH) group; an ether group CH.OR may be obtained by the reaction of a hydroxy group with an etherifying agent; an ester group CH.O.C(O)R may be obtained by the reaction of a hydroxy group with an acylating agent; an amine group CH.NH$_2$, CH.NHR or CH.NR$_2$ may be prepared from a ketone by reductive amination; or an amide CH.NHC(O)R or CH.N(C(O)R)$_2$ may be formed by acylation of an amine. A sulfone may be reduced to a sulfoxide, sulfide or thiol ether. A cyano group may be reduced to an amine group.

A key feature of using conjugating reagents of formula I or II described above is that an α-methylene leaving group and a double bond are cross-conjugated with an electron withdrawing function that serves as a Michael activating moiety. If the leaving group is prone to elimination in the cross-functional reagent rather than to direct displacement and the electron-withdrawing group is a suitable activating moiety for the Michael reaction then sequential intramolecular bis-alkylation can occur by consecutive Michael and retro Michael reactions. The leaving moiety serves to mask a latent conjugated double bond that is not exposed until after the first alkylation has occurred to give a reagent of formula I' and bis-alkylation results from sequential and interactive Michael and retro-Michael reactions. The cross-functional alkylating agents may contain multiple bonds conjugated to the double bond or between the leaving group and the electron withdrawing group.

Where bonding to the protein is via two sulfur atoms derived from a disulfide bond in the protein, the process may be carried out by reducing the disulfide bond in situ following which the reduced product reacts with the reagent having one of the structures I or II. Preferably the disulfide bond is reduced and any excess reducing agent is removed, for example by buffer exchange, before the conjugating reagent is introduced. The disulfide can be reduced, for example, with dithiothreitol, mercaptoethanol, or tris-carboxyethylphosphine using conventional methods.

Conjugation reactions may be carried out under similar conditions to known conjugation processes, including the conditions disclosed in the prior art mentioned above. For example when using conjugating reagents having one of the structures I, I' or II, the conjugation reaction according to the invention may be carried out under reaction conditions similar to those described in WO 2005/007197, WO 2009/047500, WO 2014/064423 and WO 2014/064424. The process may for example be carried out in a solvent or solvent mixture in which all reactants are soluble. For example, the protein may be allowed to react directly with the polymer conjugating reagent in an aqueous reaction medium. This reaction medium may also be buffered, depending on the pH requirements of the nucleophile. The optimum pH for the reaction will generally be at least 4.5, typically between about 5.0 and about 8.5, preferably about 6.0 to 7.5. The optimal reaction conditions will of course depend upon the specific reactants employed.

Reaction temperatures between 3-40° C. are generally suitable when using an aqueous reaction medium. Reactions conducted in organic media (for example THF, ethyl acetate, acetone) are typically conducted at temperatures up to ambient. In one preferred embodiment, the reaction is carried out in aqueous buffer which may contain a proportion of organic solvent, for example up to 20% by volume of organic solvent, typically from 5 to 20% by volume organic solvent.

The protein can be effectively conjugated using a stoichiometric equivalent or a slight excess of conjugating reagent. However, it is also possible to conduct the conjugation reaction with an excess of conjugating reagent, and this may be desirable for some proteins. The excess reagent can easily be removed by conventional means, for example ion exchange or HPLC chromatography, during subsequent purification of the conjugate.

Of course, it is possible for more than one conjugating reagent to be conjugated to a protein, where the protein contains sufficient suitable attachment points. For example, in a protein which contains two different disulfide bonds, or in a protein which contains one disulfide bond and also carries a polyhistidine tag, it is possible to conjugate two molecules of the reagent per molecule of protein.

Proteins

Any desired peptide or protein which contains nucleophilic groups may be conjugated using the process of the present invention. Suitable proteins include for example peptides, polypeptides, antibodies, antibody fragments, enzymes, cytokines, chemokines, receptors, blood factors, peptide hormones, toxin, transcription proteins, or multimeric proteins.

The following gives some specific proteins which may be conjugated using the present invention. Enzymes include carbohydrate-specific enzymes, proteolytic enzymes and the like, for example the oxidoreductases, transferases, hydrolases, lyases, isomerases and ligases disclosed by U.S. Pat. No. 4,179,337. Specific enzymes of interest include asparaginase, arginase, adenosine deaminase, superoxide dismutase, catalase, chymotrypsin, lipase, uricase, bilirubin oxidase, glucose oxidase, glucuronidase, galactosidase, glucocerbrosidase, glucuronidase, and glutaminase.

Blood proteins include albumin, transferrin, Factor VII, Factor VIII or Factor IX, von Willebrand factor, insulin, ACTH, glucagen, somatostatin, somatotropins, thymosin, parathyroid hormone, pigmentary hormones, somatomedins, erythropoietin, luteinizing hormone, hypothalamic releasing factors, antidiuretic hormones, prolactin, interleukins, interferons, for example IFN-α or IFN-β, colony stimulating factors, hemoglobin, cytokines, antibodies, antibody fragments, chorionicgonadotropin, follicle-stimulating hormone, thyroid stimulating hormone and tissue plasminogen activator.

Other proteins of interest are allergen proteins disclosed by Dreborg et al Crit. Rev. Therap. Drug Carrier Syst. (1990) 6 315-365 as having reduced allergenicity when conjugated with a polymer such as poly(alkylene oxide) and consequently are suitable for use as tolerance inducers. Among the allergens disclosed are Ragweed antigen E, honeybee venom, mite allergen and the like.

Glycopolypeptides such as immunoglobulins, ovalbumin, lipase, glucocerebrosidase, lectins, tissue plasminogen activator and glycosylated interleukins, interferons and colony stimulating factors are of interest, as are immunoglobulins such as IgG, IgE, IgM, IgA, IgD and fragments thereof.

Of particular interest are receptor and ligand binding proteins and antibodies and antibody fragments which are used in clinical medicine for diagnostic and therapeutic purposes. The binding protein/antibody may be conjugated with a diagnostic, therapeutic or labelling agent, for example a radioisotope or a cytotoxic/antiinfective drug. The use of the invention in the preparation of antibody-drug conjugates where the drug is a cytotoxic drug, for example an auristatin or maytansinoid, is especially preferred.

The protein may be derivatised or functionalised if desired. In particular, prior to conjugation, the protein, for example a native protein, may have been reacted with various blocking groups to protect sensitive groups thereon; or it may have been previously conjugated with one or more polymers or other molecules, either using the process of this invention or using an alternative process. In one embodiment of the invention, it contains a polyhistidine tag, which can be targeted by the conjugating reagent according to the invention.

In the aspect of the invention in which the conjugating reagent is capable of reaction with two nucleophiles present in a peptide or protein, the reagent may be defined as in the clauses below.

1. A conjugating reagent which is capable of reaction with two nucleophiles present in a peptide or protein, which contains a leaving group which is lost on reaction with said nucleophiles, and in which said leaving group has two points of attachment within the conjugating reagent and includes a portion —$(CH_2CH_2O)_{n1}$ in which n1 is a number of two or more.

2. A conjugating reagent as defined in clause 1, in which n1 is from 2 to 5, or from 5 to 9.

3. A conjugating reagent as defined in either clause 1 or clause 2, in which the portion —$(CH_2CH_2O)_{n1}$— has a molecular weight of up to 5 kDa.

4. A reagent as defined in any one of the preceding clauses, in which said leaving group is of the formula —S—P—S—,  —O—P—O—,   —$SO_2$—P—$SO_2$—, —$OSO_2$—P—$OSO_2$—, or —$N^+R^2R^3$—P—$N^+R^2R^3$—, in which P is a group which includes a portion —$(CH_2CH_2O)_{n1}$— and each of $R^2$ and $R^3$ independently represents a hydrogen atom or a $C_{1-4}$alkyl group or a group P.

5. A reagent as defined in any one of clauses 1 to 4, in which said leaving group is —S—$(CH_2CH_2O)_{n1}$—$(CH_2CH_2)$—S—, —O—$(CH_2CH_2O)_{n1}$—$(CH_2CH_2)$—O—, —$SO_2$—$(CH_2CH_2O)_{n1}$—$(CH_2CH_2)$—$SO_2$—, —$OSO_2$—$(CH_2CH_2O)_{n1}$—$(CH_2CH_2)$—$OSO_2$—, —$N^+R^2R^3$—$(CH_2CH_2O)_{n1}$—$(CH_2CH_2)$—$N^+R^2R^3$—, or one of the groups of formula

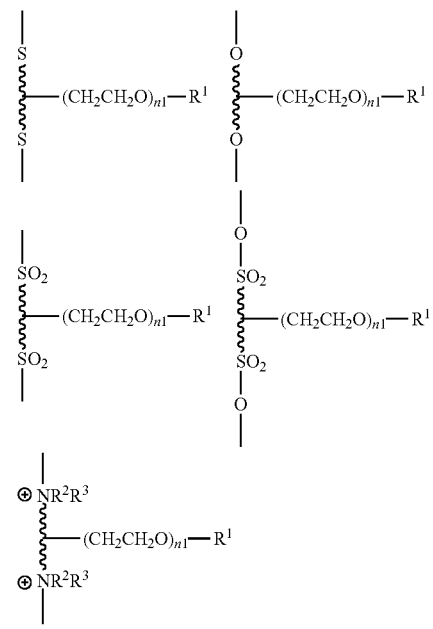

where $R^1$ is a capping group and each of $R^2$ and $R^3$ independently represents a hydrogen atom or a $C_{1-4}$alkyl group.

6. A reagent as defined in clause 5, in which said leaving group is —SO$_2$—(CH$_2$CH$_2$O)$_n$—(CH$_2$CH$_2$)—SO$_2$—.

7. A reagent as defined in clause 5, in which R$^1$ represents a hydrogen atom, a C$_{1-4}$alkyl group, an optionally substituted aryl group, or a group of formula —CH$_2$CH$_2$CO$_2$H or —CH$_2$CH$_2$NH$_2$.

8. A reagent as defined in any one of the preceding clauses, which carries a payload which is a diagnostic, therapeutic or labelling agent or a binding agent for a diagnostic, therapeutic or labelling agent.

9. A reagent as defined in any one of clauses 1 to 8, which contains the functional grouping I, I', II or III:

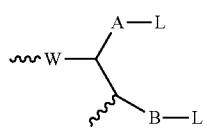
(I)

in which W represents an electron-withdrawing group; A represents a C$_{1-5}$ alkylene or alkenylene chain; B represents a bond or a C$_{1-4}$ alkylene or alkenylene chain; and both Ls together represent a leaving group which includes a portion —(CH$_2$CH$_2$O)$_{n1}$— in which n1 is a number of two or more; or

~W-CR$^4$R$^{4'}$—CR$^4$.L.L'  (II)

in which W has the meaning given for the general formula I, and either (i) each R$^4$ represents a hydrogen atom or a C$_{1-4}$alkyl group, R$^{4'}$ represents a hydrogen atom, and L and L' together represent a leaving group which includes a portion —(CH$_2$CH$_2$O)$_{n1}$— in which n is a number of two or more.

10. A reagent as defined in clause 9 which has the general formula:

(Ic)

D—Q—W—CR$^2$R$^{2'}$—CR$^2$•L•L'  (IIa)

in which Q represents a linking group and D represents a payload which is a diagnostic, therapeutic or labelling agent or a binding agent for a diagnostic, therapeutic or labelling agent.

11. A reagent as defined in clause 10, which contains the functional grouping:

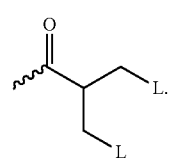
(Ib)

12. A reagent as defined in clause 11, which has the general formula:

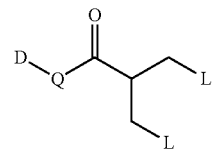
(Ie)

in which Q represents a linking group and D represents a payload which is a diagnostic, therapeutic or labelling agent or a binding agent for a diagnostic, therapeutic or labelling agent.

13. A reagent as defined in either clause 10 or clause 12, in which D-Q includes a drug or a polymer or both a drug and a polymer.

14. A reagent as defined in clause 13, in which the drug if present is a cytotoxic drug, and the polymer if present is polyethylene glycol.

Figure 1:
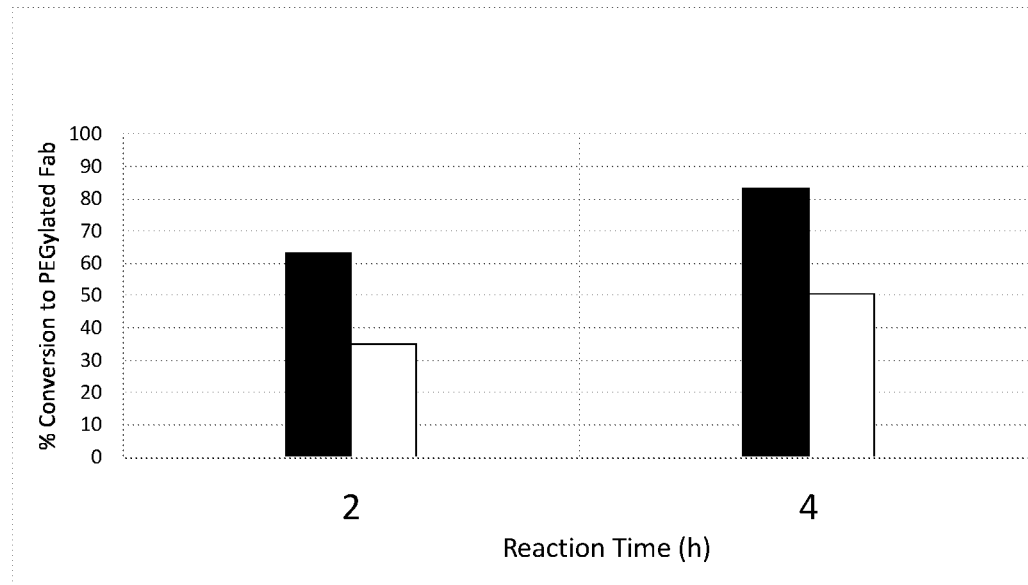
FIG. 1 shows the results of Example 17.

The following Examples illustrate the invention.

EXAMPLE 1

Synthesis of a Conjugation Reagent 2 Comprising 7 Repeat Unit Ethylene Glycol Leaving Groups Step 1: Synthesis of Compound 1.

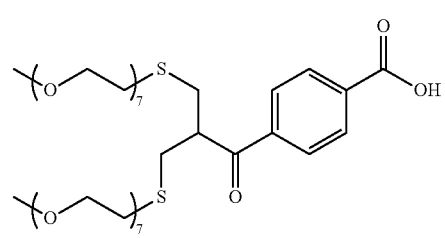

To a stirred solution of 4-[2,2-bis[p-tolylsulfonyl)-methyl]acetyl]benzoic acid (1.50 g, *Nature Protocols*, 2006, 1(54), 2241-2252) in dimethylformamide (DMF, 70 mL) was added alpha-methoxy-omega-mercapto hepta(ethylene glycol) (3.20 g, Iris Biotech) and triethylamine (2.50 mL). The resulting reaction mixture was stirred under an inert nitrogen atmosphere at room temperature. After 19 h, volatiles were removed in vacuo. The resulting residue was dissolved in water (2.4 mL) and purified by reverse phase C18-column chromatography eluting with buffer A (v/v): water:5% acetonitrile: 0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give 4-[2,2-bis[alpha-methoxy-omega-thio-hepta(ethylene glycol)]acetyl]-benzoic acid compound 1 as a thick clear colourless oil (1.77 g, 66%) m/z [M+H⁺]901.

Step 2: Synthesis of Reagent 2.

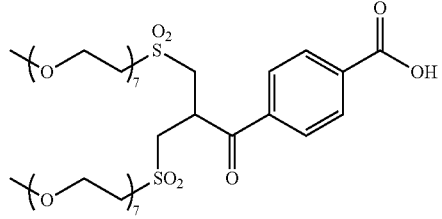

2

To a stirred solution of 1 (1.32 g) in methanol:water (18 mL, 9:1 v/v) at room temperature was added Oxone® (2.70 g). After 2.5 h, the volatiles were removed in vacuo and water was azeotropically removed with acetonitrile (2×15 mL). The resulting residue was dissolved in dichloromethane (3×10 mL), filtered through a column of magnesium sulfate and washed with dichloromethane (2×7 mL). The eluent and washings were combined and the volatiles were removed in vacuo to give a thick clear pale yellow oil 1.29 g, 92%. A portion of the residue (700 mg) was dissolved in water:acetonitrile (1.50 mL, 3:1 v/v), and purified by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give 4-[2,2-bis[alpha-methoxy-omega-sulfonyl hepta(ethylene glycol)]acetyl]benzoic acid reagent 2 as a thick clear colourless oil (524 mg, 68%) m/z [M+H⁺]965.

EXAMPLE 2

Synthesis of a PEGylation Reagent 3 Comprising 7 Repeat Unit Ethylene Glycol Leaving Groups and a 10 kDa PEG

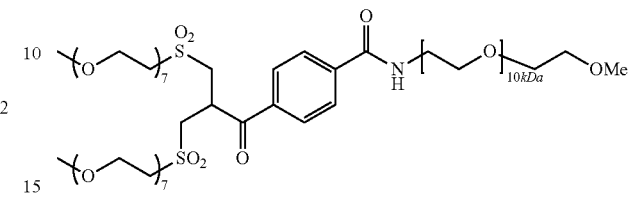

2

A stirred solution of reagent 2 (14 mg) in DMF (600 μL) was cooled to 0° C. under an argon atmosphere and 1-[bis(dimethylamino)methylene]-1H-1,2,3-triazolo[4,5-b]pyridinium 3-oxid hexafluorophosphate (HATU) (5.5 mg) and N-methylmorpholine (NMM) (1.5 μL) were added. The solution was stirred for 0.5 h at 0° C. when a solution of 10 kDa H₂N-PEG-OMe (132 mg) in dichloromethane (600 μL) was added. The resulting solution was stirred for 5 min at 0° C. before addition of further HATU (5.5 mg) and NMM (1.5 μL). The reaction solution was allowed to stir at 0° C. for 2 h before being warmed to room temperature. After 22 h, the volatiles were removed in vacuo. The resulting residue was dissolved in water and acetonitrile (v/v; 1/1, 2.0 mL), and purified by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give bis-mPEG(7u)sulfone-propanoyl-benzamide-PEG(10 kDa)OMe reagent 3 as a white powder (72 mg, 53%). ¹H NMR (600 MHz, MeOH-∂₄) 3.35 (6H), 3.36 (3H), 3.40 (4H), 3.46-3.59 (10H), 3.56-3.70 (1065H, m, PEG), 3.71-3.77 (7H), 3.85-3.91 (4H), 4.76 (1H), 8.00 (2H), 8.18 (2H).

EXAMPLE 3

Synthesis of a Fluorescent Conjugation Reagent 4 Comprising 7 Repeat Unit Ethylene Glycol Leaving Groups and a Rhodamine B dye

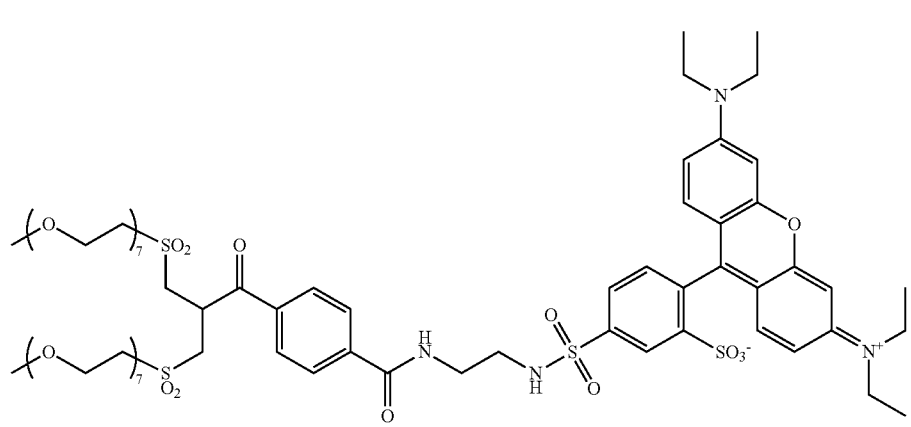

4

Reagent 2 (38 mg) and Lissamine rhodamine B ethylenediamine (20 mg, Invitrogen) were dissolved in 1.5 mL of anhydrous DMF and cooled to 0° C. HATU (15 mg) was added and the solution was stirred for 2 min before addition of NMM (8.7 μL). The reaction mixture was stirred for 2 h at 0° C. The crude reaction was partially concentrated under high vacuum for 3 h, then purified by reverse phase C18-column chromatography eluting with buffer A (v/v): water: 5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give bis-mPEG(7u)sulfone-propanoyl-benzamide-rhodamine B reagent 4 as a purple solid (43 mg, 69%). m/z [M+H]$^+$ (1549, 80%), [M+2H]$^{2+}$ (783, 100%). $^1$H NMR (600 MHz; MeOH-$\partial_4$) 1.45 (9H, s), 2.40-2.45 (8H, m), 3.40-3.46 (2H, m), 3.52-3.66 (m, PEG and CH$_2$-Ts), 4.27 (1H, q), 8.01 (2H, d), 8.08 (1H, dd), 8.15 (2H, d), 8.66 (1H, d).

EXAMPLE 4

Synthesis of a Conjugation Reagent 5 Comprising 7 Repeat Unit Ethylene Glycol Leaving Groups and an Auristatin Cytotoxic Payload

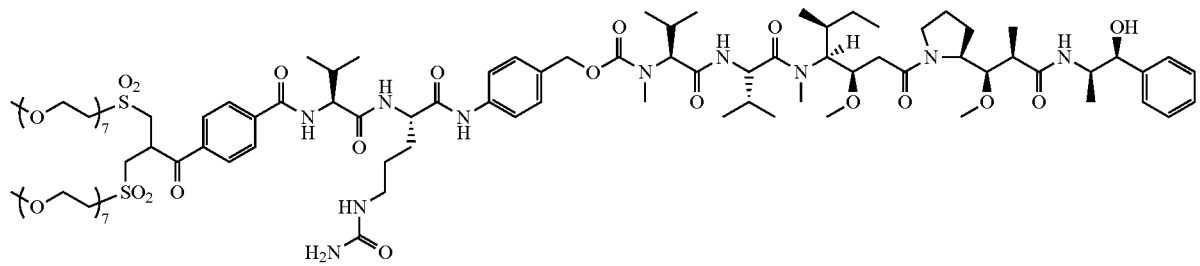

To the TFA salt of val-cit-PAB-MMAE salt having the structure below:

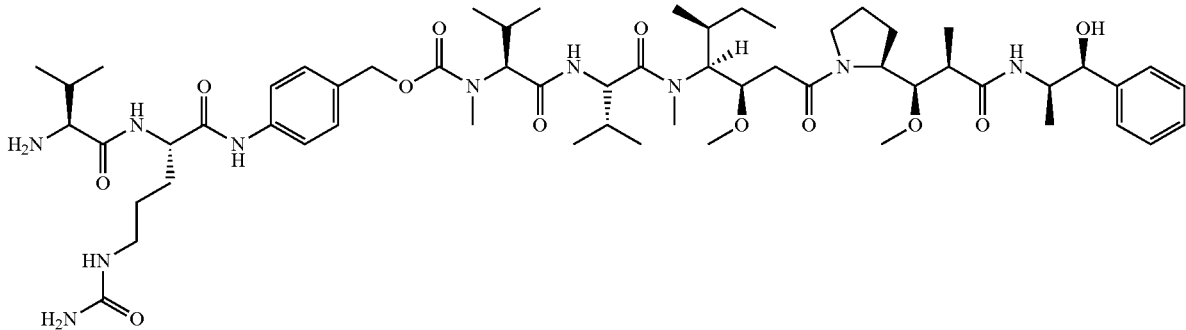

(25.0 mg) was added a solution of reagent 2 (15.6 mg) in DMF (1.5 mL) and stirred under an inert nitrogen atmosphere at room temperature for 5 min. The mixture was cooled to 0° C. and aliquots of HATU (6.1 mg) and NMM (1.8 μL) were added every 20 min for a total of 5 additions. After 1.5 h, the reaction mixture was warmed to room temperature. After 2 h, volatiles were removed in vacuo. The resulting residue was dissolved in water and acetonitrile (v/v; 1/1, 0.6 mL), and purified by reverse phase C18-column chromatography eluting with buffer A (v/v): water: 5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give bis-mPEG(7u)sulfone-propanoyl-benzamide-val-cit-PAB-MMAE reagent 5 as a white powder (22.4 mg, 68%) m/z [M+2H$^{2+}$] 1035.

EXAMPLE 5

Synthesis of a Conjugation Reagent 6 Comprising 7 Repeat Unit Ethylene Glycol Leaving Groups and an Auristatin Cytotoxic Payload

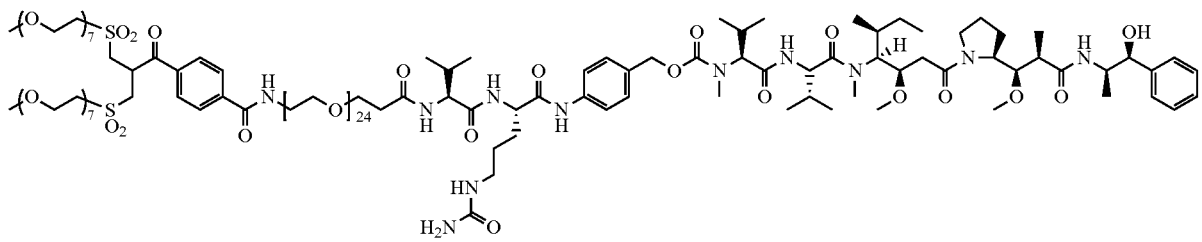

6

Step 1: Synthesis of Compound 7

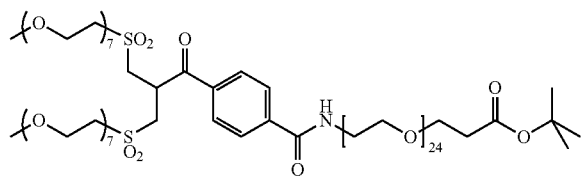

7

Stock solutions of HATU (394 mg) in DMF (4 ml) and NMM (114 µL) in DMF (4 mL) were prepared. To a DMF (10 mL) solution of reagent 2 (250 mg) was added H$_2$N-dPEG-(24u)-(CO$_2$$^t$Bu) (405 mg). The mixture was diluted with DMF (5 mL) and was stirred under an inert nitrogen atmosphere at room temperature for 5 min. The mixture was cooled to 0° C. and aliquots of HATU (1 mL) and NMM (1 mL) were added every 10 min for a total of 4 additions. After 40 min the reaction mixture was warmed to room temperature. After 2.5 h volatiles were removed in vacuo. The resulting residue was dissolved in water (2 mL), and the product was isolated by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 0:100 v/v), the organic solvent was removed in vacuo and the aqueous solvent was removed by lyophilisation to give the bis-mPEG(7u)sulfone-propanoyl-benzamide-PEG(24u)-$^t$butyl ester compound 7 as a thick clear pale yellow oil (422 mg, 76%) m/z [M−(tBu)+3H$^{3+}$] 698.46 Da.

Step 2: Synthesis of Compound 8.

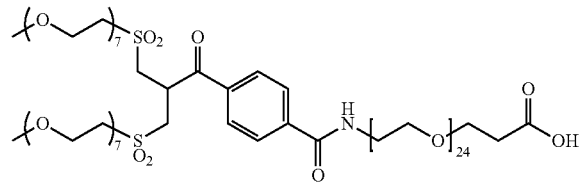

8

Reagent 7 (382 mg) was dissolved in formic acid (5 mL). The reaction mixture was stirred under an inert nitrogen atmosphere at room temperature for 1 h. The formic acid was removed by lyophilisation. The resulting solid was dissolved in water (1 mL), and the product was isolated by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 0:100 v/v), the organic solvent was removed in vacuo and the aqueous solvent was removed by lyophilisation to give the bis-mPEG(7u)sulfone-propanoyl-benzamide-PEG(24u) acid compound 8 as a white solid (194 mg, 53%) m/z [M+3H$^{3+}$] 698.33 Da.

Step 3: Synthesis of Reagent 6.

Reagent 8 (15 mg) was dissolved in DMF (0.2 mL) and val-cit-PAB-MMAE.TFA salt (11 mg) in DMF (0.2 mL) was added. The mixture was cooled to 0° C. and stirred under an inert atmosphere. HATU (2.7 mg) and NMM (0.7 mg) were added in succession and the reaction mixture was allowed to stir at 0° C. Additional amounts of HATU (2.7 mg) and NMM (0.4 mg) were added every 20 min for a total of 5 additions, and the reaction mixture was stirred at 0° C. After 1 h 40 min, the reaction was cooled to −20° C. for 16 h. The reaction solution was quenched with water (0.4 mL) and purified by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give bis-mPEG(7u)sulfone-propanoyl-benzamide-PEG(24u)-val-cit-PAB-MMAE reagent 6 as a thick clear colourless oil (7.9 mg, 34%) m/z [M+2H]$^{2+}$ 1599.98.

EXAMPLE 6

Synthesis of a Conjugation Reagent 9 Comprising 7 Repeat Unit Ethylene Glycol Leaving Groups and a Maytansinoid Cytotoxic Payload with buffer A (v/v): water:5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give the bis-mPEG(7u)sulfone-propanoyl-benzamide-val-ala-PAB-AHX-DM1 reagent 9 as a clear colourless oil (6.5 mg, 74%) m/z [M+H$^+$] 2030.

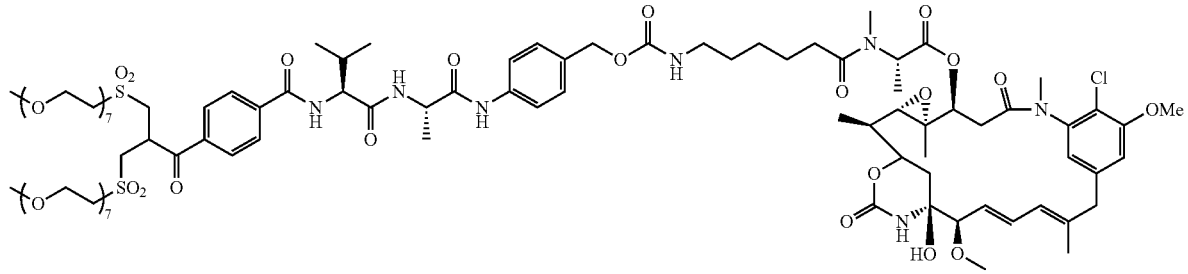

9

To a stirred solution of the val-ala-PAB-AHX-DM1 having the structure below:

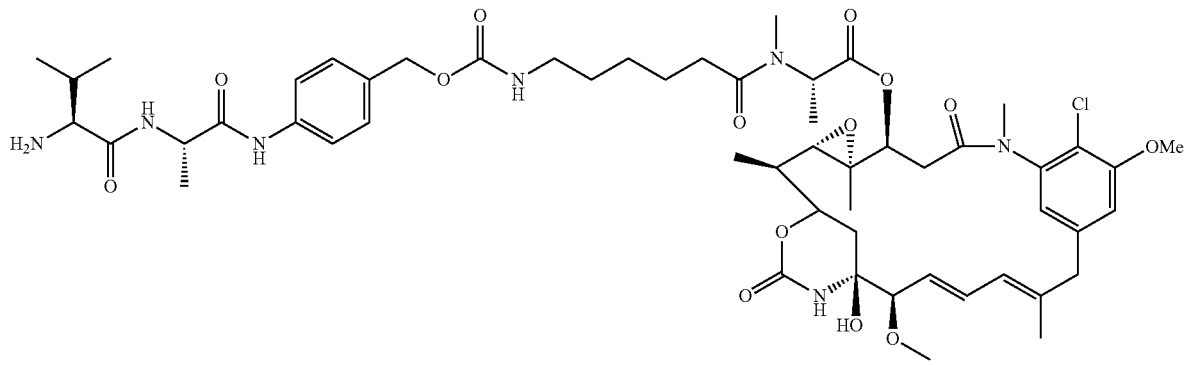 [SMILES: COc1cc2cc(c1Cl)N(C)C(=O)C[C@H](OC(=O)[C@H](C)N(C)C(=O)CCCCCNC(=O)OCc1ccc(NC(=O)[C@H](C)NC(=O)[C@@H](N)C(C)C)cc1)[C@]1(C)O[C@H]1[C@H](C)C1C[C@@](O)(NC(=O)O1)[C@H](OC)/C=C/C=C(\C)C2]

(5.2 mg) in anhydrous DMF (400 μL) was added reagent 2 (6 mg) and stirred for 5 min at 0° C. HATU (2.62 mg) and NMM (0.44 mg) were added in succession and the reaction mixture was allowed to stir at 0° C. After 20 min, an additional amount of HATU (2.62 mg) and NMM (0.44 mg) was added and the reaction mixture was stirred at 0° C. After 2.5 h, the reaction was cooled to −20° C. for 16 h. The reaction solution was concentrated in vacuo and then purified by reverse phase C18-column chromatography eluting

EXAMPLE 7

Synthesis of a Conjugation Reagent 10 Comprising 7 repeat Unit Ethylene Glycol Leaving Groups and a Maytansinoid Cytotoxic Payload

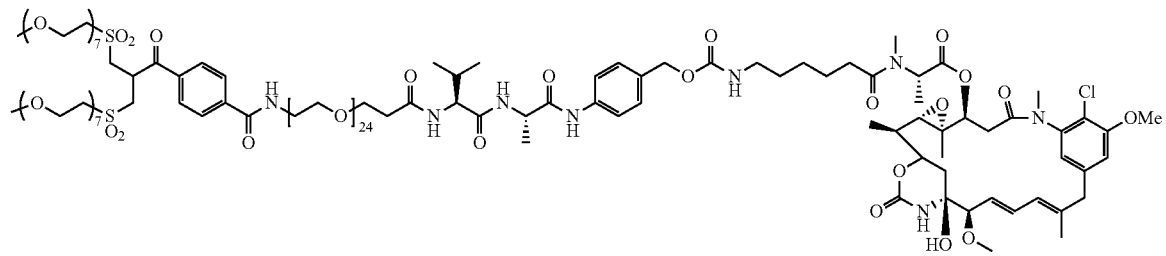

10

To a stirred solution of val-ala-PAB-AHX-DM1 (5.0 mg) in anhydrous DMF (400 μL) was added reagent 8 (13 mg) and stirred for 5 min at 0° C. HATU (2.62 mg) and NMM (0.44 mg) were added in succession and the reaction mixture was allowed to stir at 0° C. After 20 min, an additional amount of HATU (2.62 mg) and NMM (0.44 mg) was added and the reaction mixture was stirred at 0° C. After 2.5 h, the reaction was cooled to −20° C. for 16 h. The reaction solution was concentrated in vacuo and then purified by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give the bis-mPEG(7u)sulfone-propanoyl-benzamide-PEG(24u)-val-ala-PAB-AHX-DM1 reagent 10 as thick yellow oil (5.6 mg, 41%) m/z $[M-OH+H]^{2+}$ 1571.5.

EXAMPLE 8

Synthesis of Conjugation Reagents 12, 13, 14 and 15 Comprising Either 2 Repeat Unit, 12 Repeat Unit, 1 kDa, 2 kDa or 5 kDa Polymeric Ethylene Glycol leaving Groups Respectively and a Maytansinoid Cytotoxic Payload

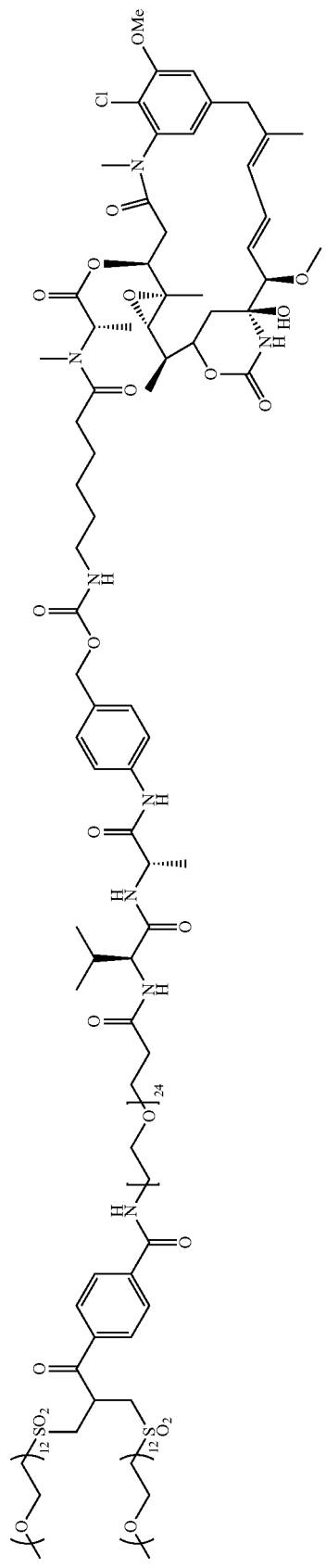
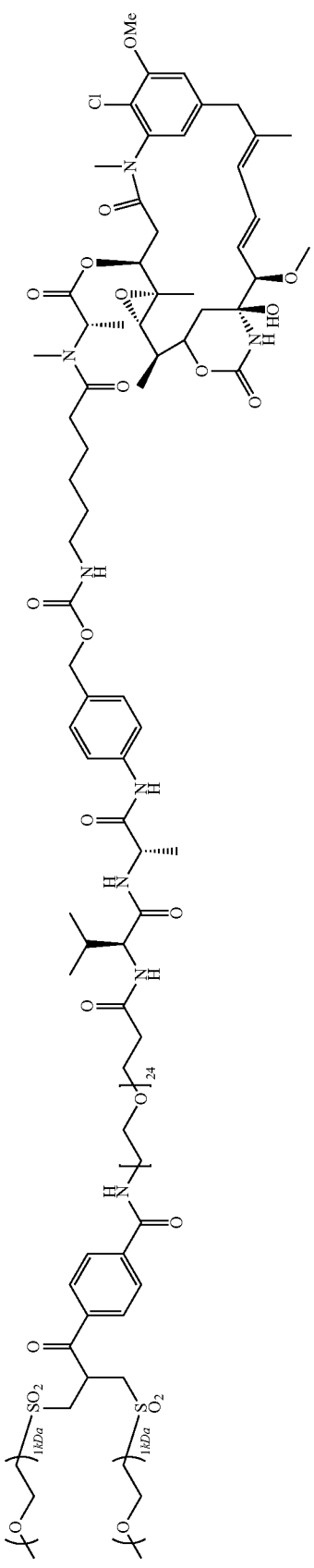

-continued
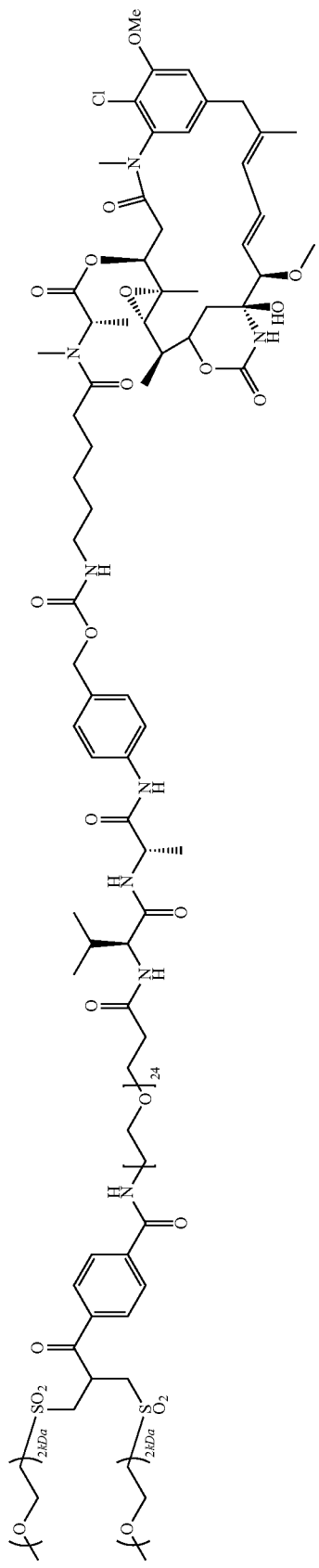
14
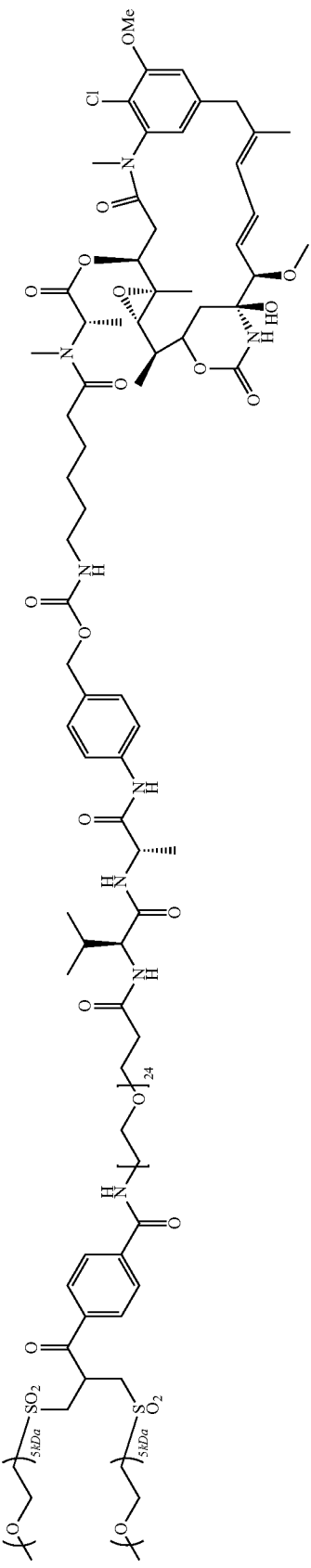
15

Maytansanoid reagents bis-mPEG(12u)sulfone-propanoyl-benzamide-PEG(24u)-val-ala-PAB-AHX-DM1 12, bis-mPEG(1 kDa)sulfone-propanoyl-benzamide-PEG(24u)-val-ala-PAB-AHX-DM1 13, bis-mPEG(2 kDa)sulfone-propanoyl-benzamide-PEG(24u)-val-ala-PAB-AHX-DM1 14 and bis-mPEG(5 kDa)sulfone-propanoyl-benzamide-PEG(24u)-val-ala-PAB-AHX-DM1 15 were synthesised in an analogous way as that described for reagent 10 in Example 7, using the thiols 2-(2-methoxyethoxy)ethanethiol, alpha-methoxy-omega-mercapto dodeca(ethylene glycol), alpha-methoxy-omega-mercapto poly(ethylene glycol 1 kDa), alpha-methoxy-omega-mercapto poly(ethylene glycol 2 kDa) and alpha-methoxy-omega-mercapto poly(ethylene glycol 5 kDa) respectively instead of alpha-methoxy-omega-mercapto hepta(ethylene glycol) for the synthesis of compound 1 in Example 1.

EXAMPLE 9

Synthesis of Conjugation Reagents 17, 18, 19 and 20 Comprising Either 2 Repeat Unit, 12 Repeat Unit, 1 kDa, 2 kDa or 5 kDa Polymeric Ethylene Glycol Leaving Groups Respectively and an Auristatin Cytotoxic Payload

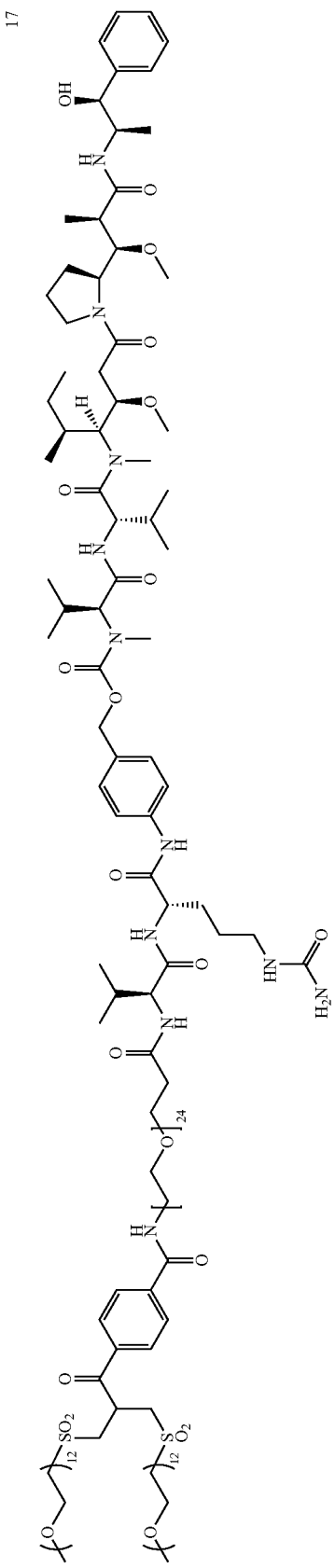
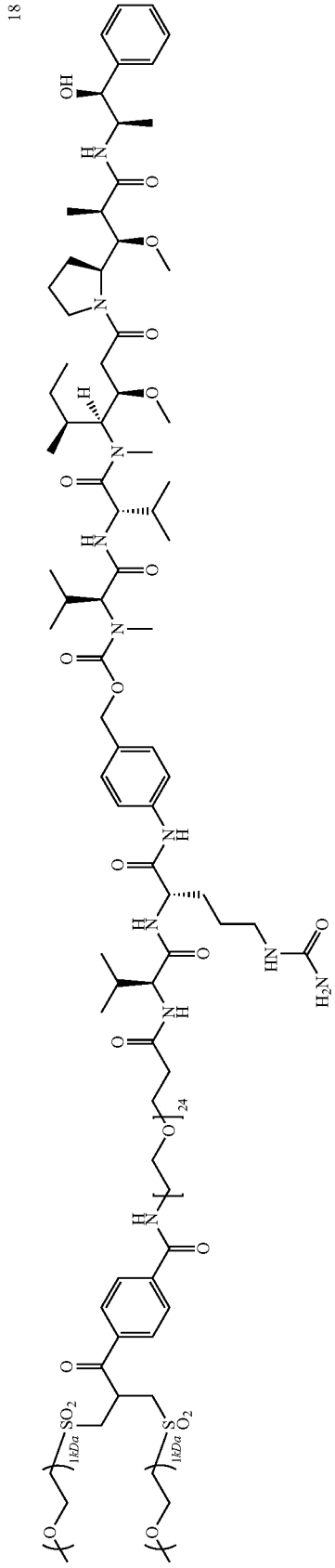
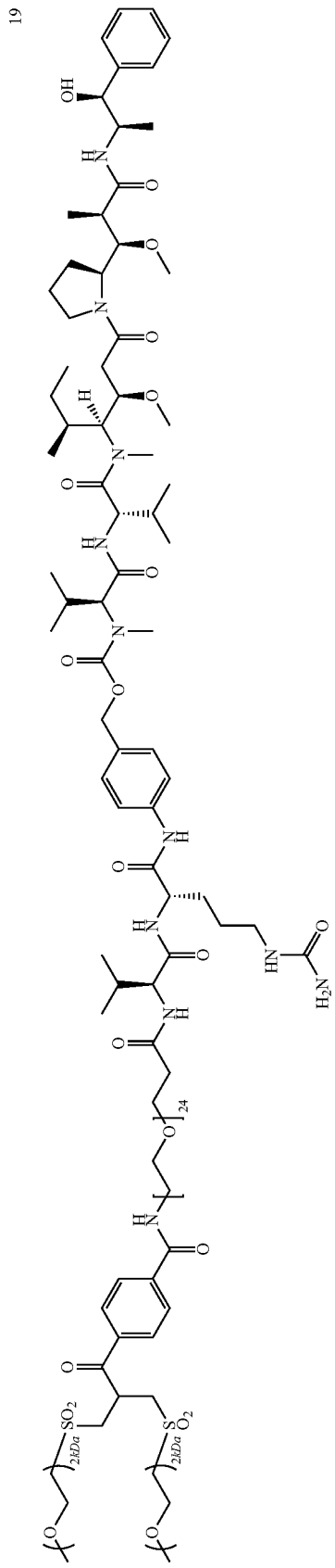

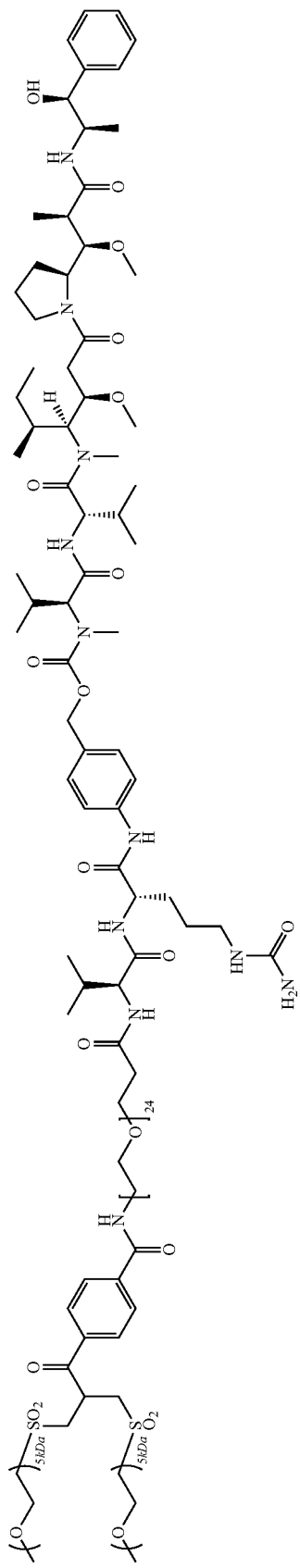

Auristatin reagents bis-mPEG(12u)sulfone-propanoyl-benzamide-PEG(24u)-val-cit-PAB-MMAE 17, bis-mPEG(1 kDa)sulfone-propanoyl-benzamide-PEG(24u)-val-cit-PAB-MMAE 18, bis-mPEG(2 kDa)sulfone-propanoyl-benzamide-PEG(24u)-val-cit-PAB-MMAE 19 and bis-mPEG(5 kDa)sulfone-propanoyl-benzamide-PEG(24u)-val-cit-PAB-MMAE 20 were synthesised in an analogous way as that described for reagent 6 in Example 5, using the thiols 2-(2-methoxyethoxy)ethanethiol, alpha-methoxy-omega-mercapto dodeca(ethylene glycol), alpha-methoxy-omega-mercapto poly(ethylene glycol 1 kDa), alpha-methoxy-omega-mercapto poly(ethylene glycol 2 kDa) and alpha-methoxy-omega-mercapto poly(ethylene glycol 5 kDa) respectively instead of alpha-methoxy-omega-mercapto hepta(ethylene glycol) for the synthesis of compound 1 in Example 1.

EXAMPLE 10

Synthesis of Conjugation Reagent 21 Comprising a Maytansinoid Cytotoxic Payload temperature and after 22 h the volatiles were removed in vacuo. The resulting residue was dissolved in dichloromethane (1 mL) and purified by normal phase column chromatography eluting with dichloromethane:methanol (100:0 v/v to 80:20 v/v). The organic solvent was removed in vacuo to give Fmoc-L-Glu-[O$^t$Bu]-[PEG(24u)-OMe] as a colourless oil (84 mg, 67%). Piperidine (49 µL) was added to a solution of compound Fmoc-L-Glu-[O$^t$Bu]-[PEG(24u)-OMe](74 mg) in DMF (2 mL) under an argon atmosphere and the resulting solution stirred at room temperature for 22 h, after which the volatiles were removed in vacuo. The resulting residue was triturated with hexane (3×0.7 mL). The organic solvent was decanted each time and the resulting residue dried in vacuo to give the L-Glu-[OtBu]-[PEG(24u)-OMc] compound 22 as a white solid (61 mg, 97%). m/z [M+H]$^+$ (1097, 10%), [M+2H]$^{2+}$ (1035, 100%).

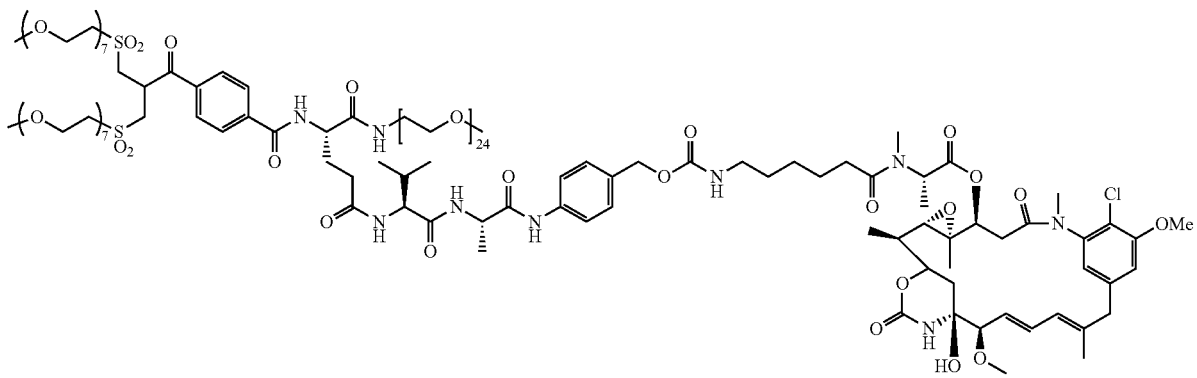

21

Step 1: Synthesis of Compound 22.

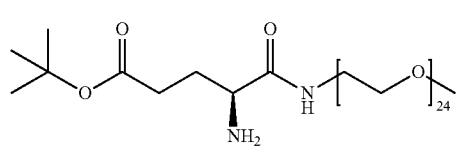

22

A solution of Fmoc-L-Glu-(OtBu)-OH (36 mg) in DMF (2 mL) was cooled to 0° C. under an argon atmosphere and (benzotriazol-1-yloxy)tris-(dimethylamino) phosphonium hexafluorophosphate (BOP) (41 mg) was added, followed by NH$_2$-PEG(24u)-OMe (100 mg) and N,N-diisopropylethylamine (19 µL). The solution was allowed to warm to room Step 2: Synthesis of Compound 23.

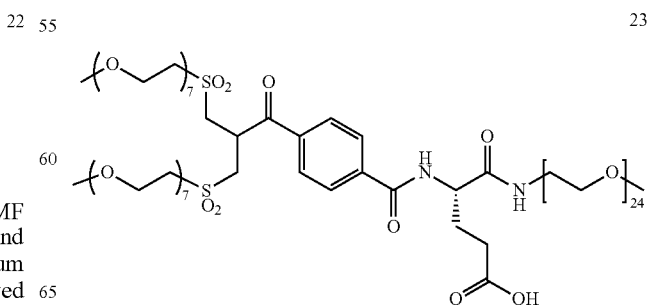

23

A solution of compound 22 (26.6 mg) in DMF (550 μL) was cooled to 0° C. under an argon atmosphere to which HATU (10.5 mg) was added and the solution stirred for 0.5 h at 0° C. To this was added a solution of reagent 2 (32 mg) in DMF (550 μL). The resulting solution was stirred for 5 min at 0° C. before addition of NMM (2.9 μL) and HATU (10.5 mg). The reaction solution was allowed to stir at 0° C. for 2 h before being warmed to room temperature and stirred for a further 3.5 h. After this time the volatiles were removed in vacuo. The resulting residue was dissolved in water and acetonitrile (v/v; 1/1, 1.2 ml), and purified by reverse phase C18-column chromatography eluting with buffer A (v/v): water:5% acetonitrile:0.1% formic acid and buffer B (v/v): acetonitrile:0.1% formic acid (100:0 v/v to 0:100 v/v). The organic solvent was removed in vacuo and the aqueous solvent removed by lyophilisation to give bis-mPEG(7u) sulfone-propanoyl-benzamide-L-Glu-[OtBu]-[PEG(24u)-OMe] as a colourless oil (30.5 mg, 55%). $^1$H NMR (400 MHz, MeOH-$\partial_4$) 8.19 (2H, d), 8.04 (2H, d), 4.83-4.71 (1H, m), 4.58 (1H, dd), 3.92-3.83 (6H, m), 3.78-3.56 (140H, m), 3.57-3.51 (6H, m), 3.40 (4H, dd), 3.36 (3H, s), 3.35 (6H, s), 2.41 (2H, t), 2.24-2.13 (1H, m), 2.10-1.98 (1H, m), 1.45 (9H, s); m/z [M+Na]$^+$ (2243, 50%), [M+H]$^+$ (2221, 40%), [M+Na+2H]$^{3+}$ (747, 100%). A solution of bis-mPEG(7u) sulfone-propanoyl-benzamide-L-Glu-[OtBu]-[PEG(24u)-OMe] (30 mg) in dichloromethane (2 mL) under an argon atmosphere was cooled to 0° C. to which trifluoroacetic acid (500 μL) was added and the resulting solution stirred for 1.5 h. The reaction mixture was allowed to warm to room temperature and stirred for a further 1 h. After this time the volatiles were removed in vacuo. The resulting residue was dissolved in water and acetonitrile (v/v; 1/1, 0.6 mL), and purified by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent removed by lyophilisation to give the bis-mPEG(7u)sulfone-propanoyl-benzamide-L-Glu-[OH]-[PEG(24u)-OMe] compound 23 as a colourless oil (20 mg, 68%). $^1$H NMR (400 MHz, MeOH-$\partial_4$) 8.19 (2H, d), 8.04 (2H, d), 4.81-4.72 (1H, m), 4.59 (1H, dd), 3.92-3.84 (6H, m), 3.67-3.50 (146H, m), 3.40 (4H, dd), 3.36 (3H, s), 3.35 (6H, s), 2.48 (2H, t), 2.26-2.15 (1H, m), 2.15-2.03 (1H, m); m/z [M+H]$^+$ (2165, 55%), [M+2H]$^{2+}$ (1083, 60%), [M+2H+Na]$^{3+}$ (729, 100%).

Step 3: Synthesis of Reagent 21

A solution of compound 23 (15.0 mg) in DMF (600 μL) was cooled to 0° C. under an argon atmosphere. HATU (2.9 mg) was added and the solution stirred for 0.5 h at 0° C. To this was added a solution of val-ala-PAB-AHX-DM1 (9.2 mg) and NMM (0.84) in DMF (600 μL), which had been stirred at room temperature for 0.5 h. After 5 min, an additional amount of HATU (2.9 mg) and NMM (0.8 μL) was added and the reaction mixture stirred at 0° C. After 3 h, an additional amount of HATU (0.7 mg) was added and the reaction mixture stirred at 0° C. After a further 2 h, the reaction was stored at −20° C. for 16 h. The reaction solution was concentrated in vacuo and purified by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent removed by lyophilisation to give the bis-mPEG(7u)sulfone-propanoyl-benzamide-L-Glu-[val-ala-PAB-AHX-DM1]-[PEG(24u)-OMe] compound 21 as a thick clear colourless oil (14.3 mg, 64%). $^1$H NMR (600 MHz, MeOH-$\partial_4$) (selected characteristic signals) 5.69 (1H, dd), 6.59 (1H, dd), 6.68 (1H, s), 6.69 (1H, d), 7.10 (1H, s), 7.28 (2H, d), 7.57 (2H, d), 8.01 (2H, d), 8.16 (2H, d); m/z [M-AHX-DM1]$^+$ (2422, 40%).

EXAMPLE 11A

Synthesis of a Conjugation Reagent 24 Comprising 7 Repeat Unit Polymeric Leaving Groups and a Maytansinoid Cytotoxic Payload

24

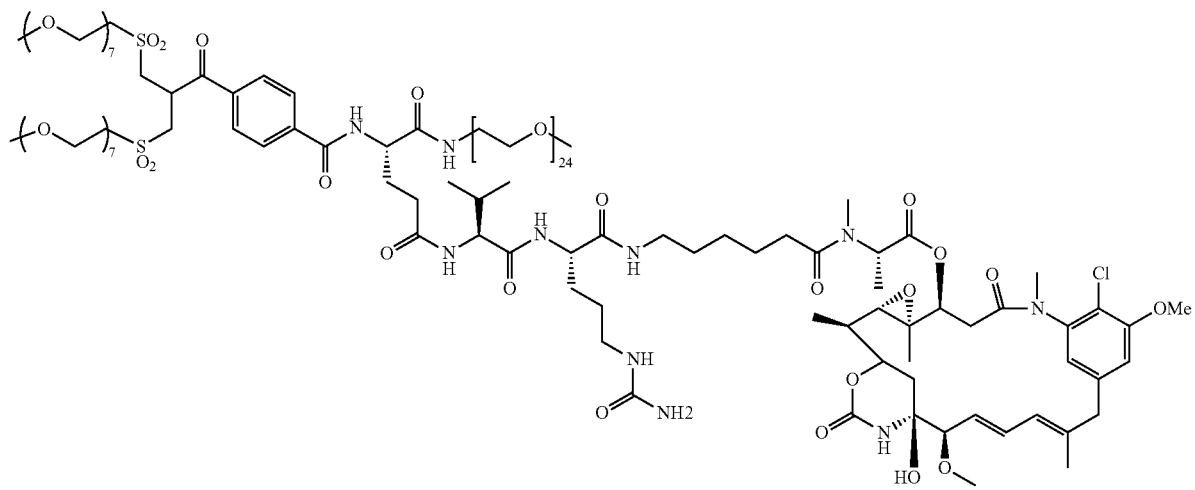

A solution of compound 23 (12.4 mg) in DMF (500 μL) was cooled to 0° C. under an argon atmosphere. HATU (2.4 mg) was added and the solution stirred for 0.5 h at 0° C. To this was added a solution of val-cit-AHX-DM1 (made in an analogous way to compound 50 using AHX-DM1 instead of compound 47, 6.4 mg) and NMM (0.7 μL) in DMF (500 μL), which had been stirred at room temperature for 0.5 h. After 5 min, an additional amount of HATU (1.2 mg) and NMM (0.4 μL) was added and the reaction mixture stirred at room temperature. After 2 h, an additional amount of HATU (1.2 mg) and NMM (0.4 μL) was added and the reaction mixture stirred at room temperature. After a further 1 h, the reaction solution was concentrated in vacuo and purified by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent removed by lyophilisation to give bis-mPEG(7u)sulfone-propanoyl-benzamide-L-Glu-[val-cit-AHX-DM1]-[PEG(24u)-OMe] 24 as a thick clear colourless oil (9.6 mg, 53%). m/z [M–H$_2$O]$^+$(3148, 8%), [M–H$_2$O]$^{2+}$ (1575, 40%), [M–H$_2$O]$^{3+}$ (1050, 100%), 1036 [M–NHCO—H$_2$O]$^{3+}$.

EXAMPLE 11B

Synthesis of a Conjugation Reagent 25 Comprising an Auristatin Cytotoxic Payload

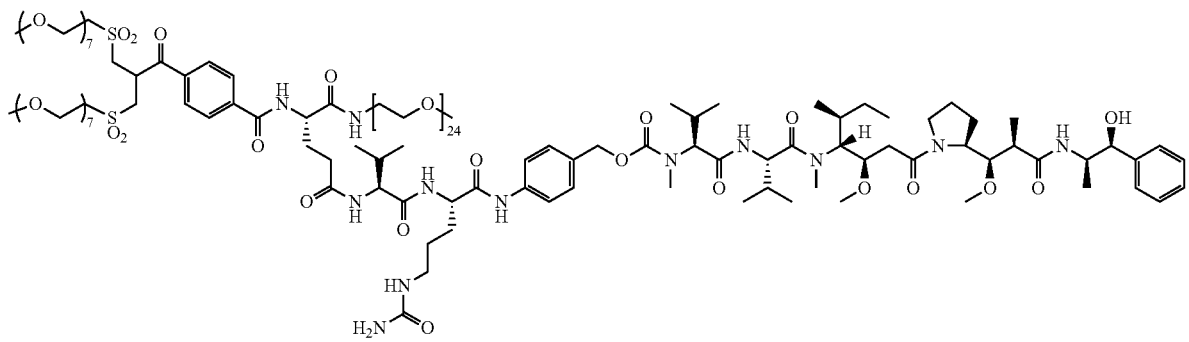

25

Reagent 25 was synthesised in analogous way to reagent 24 of Example 11A from compound 23 and val-cit-PAB-MMAE TFA salt. Bis-mPEG(7u)sulfone-propanoyl-benzamide-L-Glu-[val-cit-PAB-MMAE]-[PEG(24u)-OMe] 25 was isolated as a colourless oil. m/z [M+H]$^+$ (3270, 12%), [M+2H]$^{2+}$ (1636, 50%), [M+3H]$^{3+}$ (1091, 100%).

EXAMPLE 12

Synthesis of Conjugation Reagent 27 for Imaging and Chelating Applications Comprising 7 Repeat Unit Polymeric Ethylene Glycol Leaving Groups and Desferrioxamine

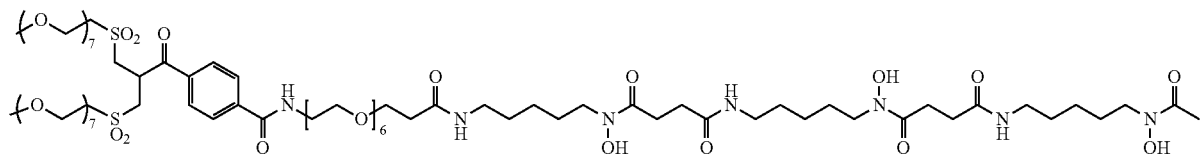

27

Step 1: Synthesis of Compound 28.

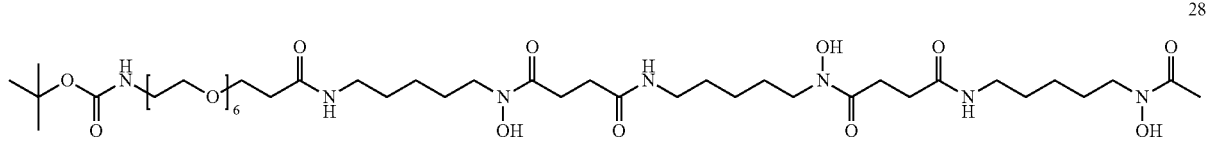

28

10

To a solution of 21-(Boc-amino)-4,7,10,13,16,19-hexaoxaheneicosanoic acid (50 mg, Sigma-Aldrich) in DMF (2 mL) under an argon atmosphere at room temperature was added (benzotriazol-1-yloxy)tris-(dimethylamino) phosphonium hexafluorophosphate (BOP) (73 mg) and the solution was stirred for 0.5 h. To this was added a solution of desferrioxamine mesylate (87 mg, Sigma-Aldrich) and N,N-diisopropylethylamine (29 μL) in DMF (2 mL) which had been stirred at room temperature for 0.5 h. After 24 h the reaction solution was concentrated in vacuo and then purified directly by reverse phase C18-column chromatography eluting with buffer A (v/v): water:5% acetonitrile:0.1% formic acid and buffer B (v/v): acetonitrile:0.1% formic acid (100:0 v/v to 50:50 v/v). The organic solvent was removed in vacuo and the aqueous solvent was removed by lyophilisation to give the BocNH-PEG(6u)-desferrioxamine compound 28 as a white solid (50 mg, 46%) m/z [M+Na]+ (1019, 50%), [M+H]+ (997, 95%), [M+2H]2+ (499, 100%); 1H NMR (600 MHz; MeOH-δ4) 1.28-1.38 (7H, m), 1.43 (9H, s), 1.49-1.55 (6H, m), 1.60-1.67 (5H, m), 2.09 (3H, s), 2.41-2.47 (6H, m), 2.76 (4H, t), 3.14-3.19 (6H, m), 3.21 (2H, t), 3.50 (2H, t), 3.57-3.65 (27H, m), 3.70-3.73 (2H, t).

Step 2: Synthesis of Compound 29.

NH2-PEG(6u)-desferrioxamine compound 29 as a white solid (44 mg, quantitative yield) which was used in the next step without any further purification: m/z [M+H]+ (897, 100%), [M+2H]2+ (449, 100%).

Step 3: Synthesis of Reagent 27.

A solution of reagent 2 (17 mg) in DMF (750 μL) was cooled to 0° C. under an argon atmosphere before HATU (8.0 mg) was added and the solution was stirred for 0.5 h at 0° C. To this was added a solution of compound 29 (23 mg) and NMM (2.1 μL) in DMF (750 μL) and the reaction mixture was stirred at 0° C. Additional amounts of reagent 2, HATU and NMM were added over 4 h. After a further 15 h, the reaction solution was concentrated in vacuo and then purified by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 50:50 v/v). The organic solvent was removed in vacuo and the aqueous solvent was removed by lyophilisation to give the bis-mPEG(7u)sulfone-pro-

29

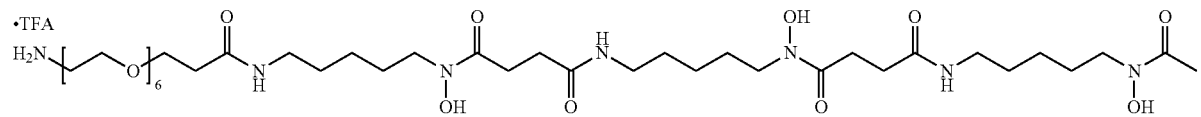

A solution of compound 28 (49 mg) in dichloromethane (DCM) (3 mL) under an argon atmosphere was cooled to 0° C. and trifluoroacetic acid (TFA) (750 μL) was added. The solution was allowed to warm to room temperature. After 1 h, toluene (2 mL) was added to the reaction mixture and the volatiles were removed in vacuo. The resulting residue was dissolved in Buffer A (v/v): water:5% acetonitrile:0.1% formic acid (2 mL) and the aqueous solvent was removed by lyophilisation to remove any residual TFA and to give the panoyl-benzamide-PEG(6u)-desferrioxamine reagent 27 as a clear colourless oil (20.6 mg, 49%) m/z [M+H]+ (1844, 95%), [M+2H]2+ (922, 100%), [M+3H]3+ (615, 100%).

EXAMPLE 13 (COMPARATIVE)

Synthesis of Conjugation Reagent 30 for Imaging and Chelating Applications Comprising Tosyl Leaving Groups and Desferrioxamine

30

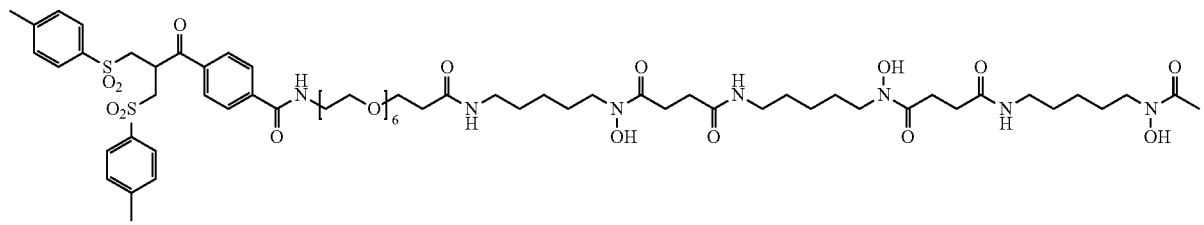

To a solution of compound 29 (43 mg) in DMF (2.5 mL) was added NMM (6 μL) and the solution was stirred for 0.5 h at room temperature. To this was added a solution of the known 4-[2,2-bis[(p-tolylsulfonye-methyl]acetyl]benzoic acid (29 mg, Nature Protocols, 2006, 1(54), 2241-2252) in DMF (700 μL). Additional NMM was added to the reaction mixture after 1 h, 2 h, 19 h, 23 h and 25 h (15.6 μL in total). After 26 h the reaction solution was concentrated in vacuo and then purified by reverse phase C18-column chromatography eluting with buffer A (v/v): water:5% acetonitrile: 0.05% trifluoroacetic acid and buffer B (v/v): acetonitrile: 0.05% trifluoroacetic acid (100:0 v/v to 0:100 v/v). The organic solvent was removed in vacuo and the aqueous solvent was removed by lyophilisation to give the bis-tolylsulfone-propanoyl-benzamide PEG(6u)-desferrioxamine reagent 30 as a clear colourless oil (19 mg, 29%) m/z [M+H]$^+$ (1379, 98%), [M+2H]$^{2+}$ (690, 100%); $^1$H NMR (600 MHz; MeOH-$\delta_4$) 1.28-1.36 (7H, m), 1.48-1.55 (6H, m), 1.59-1.65 (5H, m), 2.09 (3H, s), 2.40-2.46 (6H, m), 2.50 (6H, s), 2.74-2.78 (4H, m), 3.14-3.17 (5H, m), 3.55-3.61 (23H, m), 3.62-3.70 (12H, m), 3.75-3.80 (2H, m). 4.09-4.14 (1H, m), 7.44 (4H, d), 7.55 (2H, d), 7.62 (4H, d), 7.82 (2H, d).

EXAMPLE 14

Synthesis of a Conjugation Reagent 31 Comprising a hexaPEG-Disulfone Leaving Group and a Maytansinoid Cytotoxic Payload

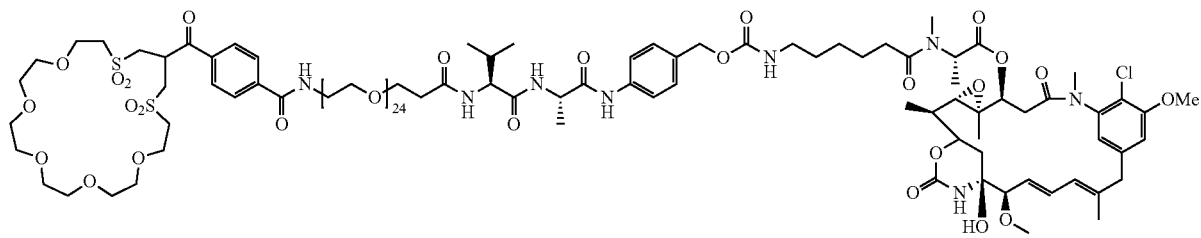

31

Step 1: Synthesis of Compound 32.

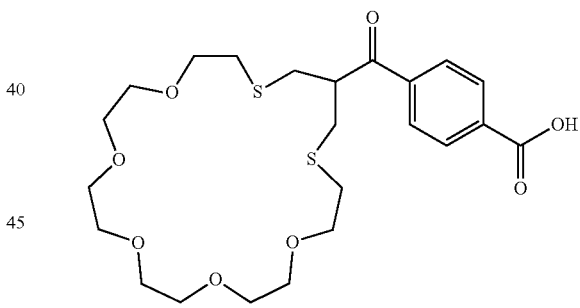

32

To a stirred solution of 4-[2,2-bis[(p-tolylsulfonyl)-methyl]acetyl]benzoic acid (542 mg, Nature Protocols, 2006, 1(54), 2241-2252) in DMF (40 mL) was added hexa(ethylene glycol) dithiol (400 μL) and Cs$_2$CO$_3$ (2.4 g). The resulting reaction mixture was stirred under an inert nitrogen atmosphere at room temperature. After 40 h, volatiles were removed in vacuo. The resulting residue was dissolved in water (4 mL), and purified by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give the hexaPEG-dithioether propanoyl-benzoic acid compound 32 as a white solid (180 mg, 33.1%) m/z [M+Na$^+$] 525. $^1$HNMR (600 MHz, CDCl$_3$) 2.72-2.78 (4H, m, CH$_2$-S), 2.95-3.04 (4H, m), 3.65-3.72(18H, m, PEG), 4.76 (1H, m), 8.11 (2H, d), 8.21 (2H, d).

Step 2: Synthesis of Compound 33.

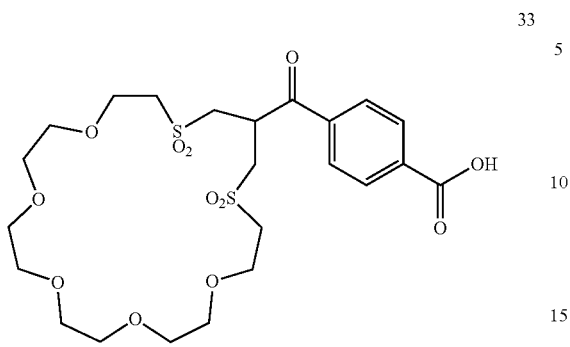

The hexaPEG-disulfone propanoyl-benzoic acid compound 33 was synthesised in an analogous way as that described for reagent 2 in Example 1, using compound 32 instead of compound 1.

Step 3: Synthesis of Compound 34.

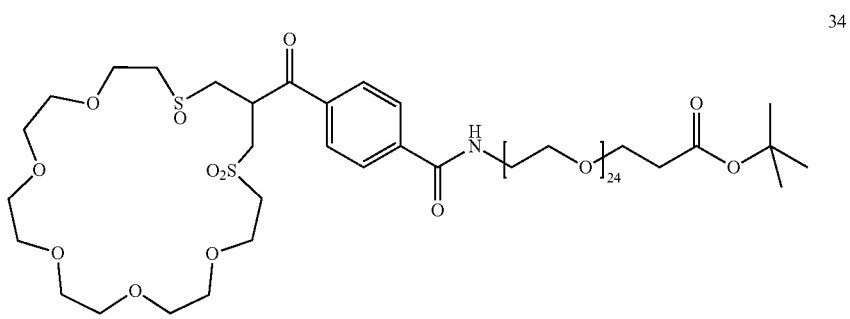

The hexaPEG-disulfone propanoyl-benzamide-PEG(24u)-ᵗbutyl ester compound 34 was synthesised in an analogous way as that described for compound 7 in Example 5, using compound 33 instead of compound 2.

Step 4: Synthesis of Compound 35.

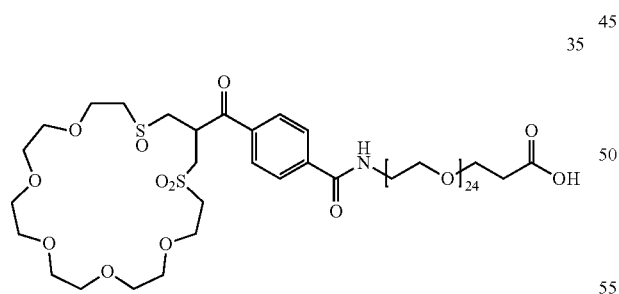

The hexaPEG-disulfone propanoyl-benzamide-PEG(24u)-acid compound 35 was synthesised in an analogous way as that described for compound 8 in Example 5, using compound 34 instead of compound 7.

Step 5: Synthesis of Reagent 31.

The maytansanoid reagent hexaPEG-disulfone propanoyl-benzamide-PEG(24u)-val-ala-PAB-AHX-DM1 31 was synthesised in an analogous way as that described for reagent 10 in Example 7, using compound 35 instead of compound 8.

EXAMPLE 15 (COMPARATIVE)

Synthesis of a Conjugation Reagent 36 Comprising Tosyl Leaving Groups and a Rhodamine B Dye

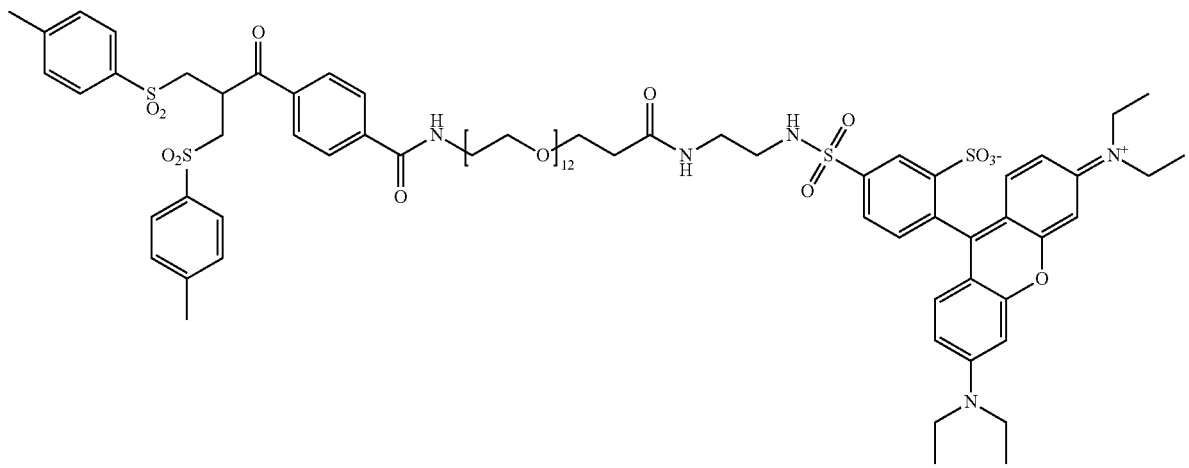

36

Step 1: Synthesis of Compound 37.

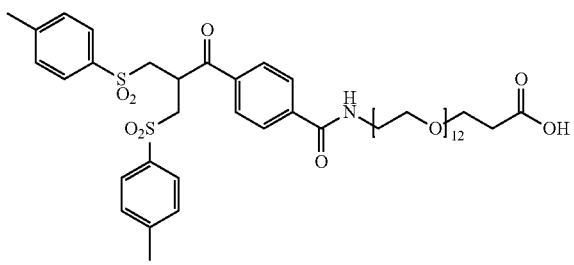

37

The 4-[2,2-bis[(p-tolylsulfonyl)-methyl]acetyl]benzamide-PEG(12u)-acid compound 37 was synthesised in an analogous way as that described for reagent 8 in Example 5, using the known 4-[2,2-bis[(p-tolylsulfonyl)-methyl]acetyl]benzoic acid (*Nature Protocols*, 2006, 1(54), 2241-2252) instead of reagent 2.

Step 2: Synthesis of Reagent 36.

The 4-[2,2-bis[(p-tolylsulfonyl)-methyl]acetyl]benzamide-PEG(12u)-rhodamine B reagent 36 was synthesised in an analogous way as that described for reagent 4 in Example 3, using compound 37 instead of reagent 2.

EXAMPLE 16

Synthesis of a Conjugation Reagent 38 Comprising a 7 Repeat Unit Polymeric Leaving Group, an Aryl Leaving Group and an Auristatin Cytotoxic Payload

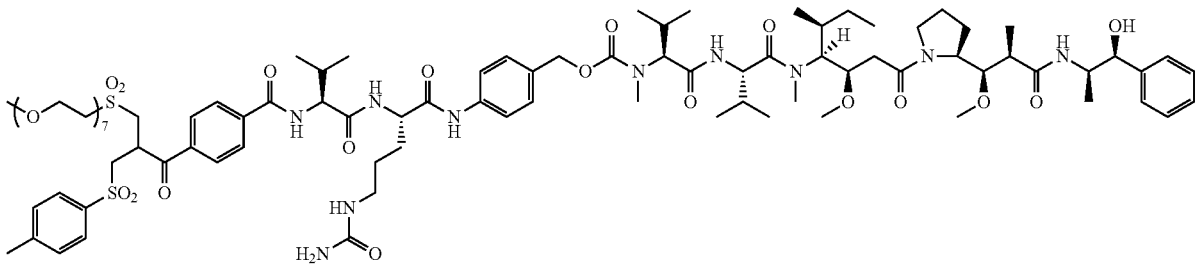

38

Step 1: Synthesis of Compound 39.

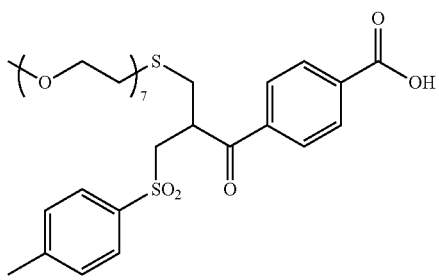

39

To a stirred solution of the known 4-[2,2-bis[(p-tolylsulfonyl)-methyl]acetyl]benzoic acid (200 mg, *Nature Protocols,* 2006, 1(54), 2241-2252) in dimethylformamide (DMF, 8 mL) was added alpha-methoxy-omega-mercapto hepta (ethylene glycol) (142 mg) and NMM (264 µL). The resulting reaction mixture was stirred under an inert nitrogen atmosphere at room temperature. After 19 h, volatiles were removed in vacuo and the resulting residue was dissolved in acetonitrile (800 µL), and purified by reverse phase C18-column chromatography eluting with buffer A (v/v): water: 5% acetonitrile: 0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give mono-mPEG(7u)sulfone-propanoyl-benzamide-mono-(tosylmethyl) propanoyl)benzoic acid compound 39 as a thick clear colourless oil (132 mg, 47%) m/z [M+H$^+$] 701.1.

Step 2: Synthesis of Reagent 40.

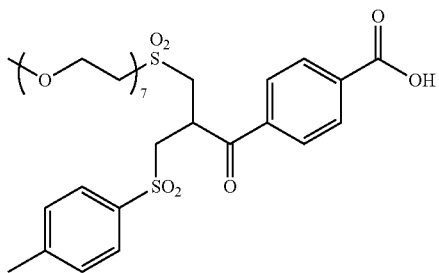

40

To a stirred solution of compound 39 (116 mg) in methanol:water (5 mL, 9:1 v/v) at room temperature was added Oxone© (305 mg). After 75 min, the volatiles were removed in vacuo and water was azeotropically removed with acetonitrile (3×15 mL). The resulting residue was dissolved in dichloromethane (3×10 mL), filtered through a column of magnesium sulphate and washed with dichloromethane (2×7 mL). The eluent and washings were combined and the volatiles were removed in vacuo to give a thick clear pale yellow oil. The residue was dissolved in water:acetonitrile (800 µL, 1:4 v/v), and purified by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give the 4-(3-((2-hepta(ethylene glycol) methoxyethyl) sulfonyl)-2-(tosylmethyl) propanoyl) benzoic acid compound 40 as a thick clear colourless oil (103 mg, 78%) m/z [M+H$^+$] 733.2.

Step 3: Synthesis of Reagent 38

To val-cit-PAB-MMAE.TFA salt (25.0 mg) was added a solution of reagent 40 (11.8 mg) in DMF (1.5 mL) and stirred under an inert atmosphere at room temperature for 5 min. The mixture was cooled to 0° C. and aliquots of HATU (6.1 mg) and NMM (1.8 µL) were added over a period of 5 h for a total of 5 additions. After 1.5 h, the reaction mixture was warmed to room temperature. After 6 h, volatiles were removed in vacuo, and the resulting residue was dissolved in water and acetonitrile (v/v; 1/4, 0.6 mL), and purified by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give mono-mPEG(7u)sulfone-mono-(tosylmethyl propanoyl-benzamide-)-val-cit-PAB-MMAE reagent 38 as a bright white powder (13.0 mg, 44%) m/z [M+2H$^{2+}$] 919.3.

EXAMPLE 17

PEGylation at a Reduced Fab Disulfide Bond using Reagent 3 and Comparison with the Known PEGylation Reagent 4-[2,2-bis[(p-tolylsulfonyl)-methyl] acetyl]benzamide-PEG(10 kDa)-OMe 41 (*Nature Protocols,* 2006, 1(54), 2241-2252)

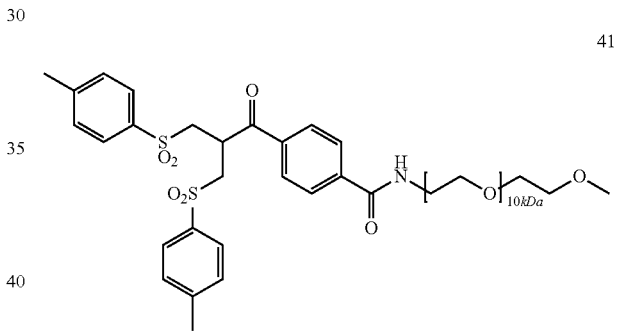

41

The interchain disulfide of a Fab (5.71 mg, 2.33 mg/mL in PBS produced by papain digestion of trastuzumab), was reduced by adding 50 µL of 0.5 M dithiothreitol (DTT) aqueous solution and incubating at 22° C. for 1 h. The reducing agent was then removed using a PD10 column equilibrated with 20 mM sodium phosphate buffer, 150 mM NaCl, 20 mM EDTA, pH 7.5, and the reduced Fab diluted further to 1.24 mg/mL with the same buffer. Reagents 3 and 41 were dissolved independently in ultrapure water at 10 mg/mL and added to separate solutions of reduced Fab at 1.5 molar equivalents of PEG reagent to Fab. The PEGylation reactions were allowed to progress at 22° C., whereupon samples were taken for SDS-PAGE analysis after 2 and 4 h.

The % conversion to PEGylated Fab was estimated based on SDS-PAGE band density using an ImageQuant™ system (GE Healthcare). The results are shown in FIG. 1, which compares the extent of conjugation of PEGylation Reagent 3 (black bars) vs Reagent 41 (white bars) to the Fab. Reaction with reagent 3 gave 63% and 83% conversion to PEGylated Fab at 2 h and 4 h respectively. For reagent 41, conversions were 35% and 51% at 2 and 4 h respectively. These data show that reagent 3 reacts more quickly, producing a larger amount of PEGylated Fab in a shorter timeframe than reagent 41.

EXAMPLE 18

PEGylation at an Interferon-Alpha Disulfide Bond using Reagent 3 and Comparison with the Known PEGylation Reagent 41

Figure 2:
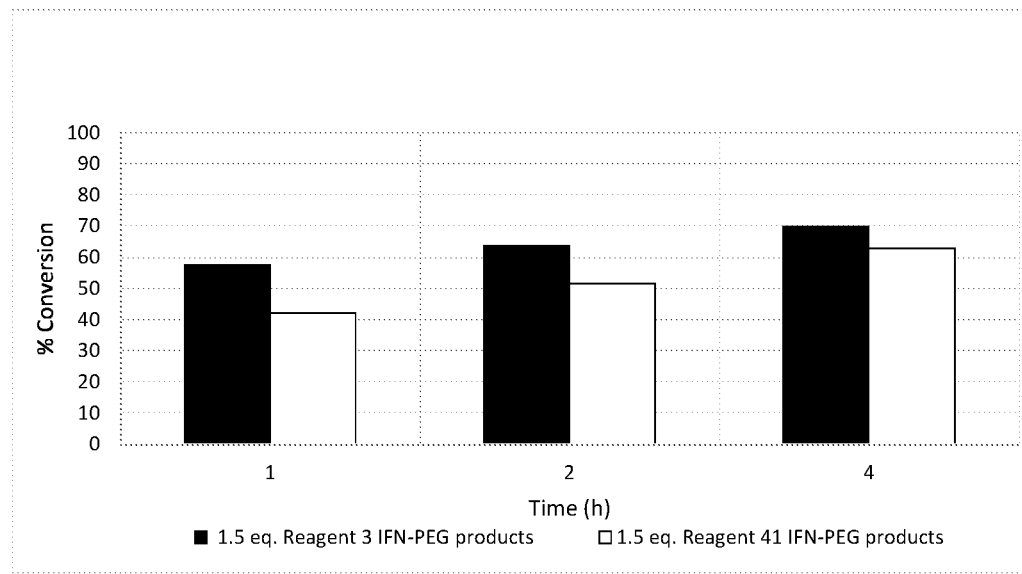
FIG. 2 shows the results of Example 18.

Interferon α-2a (IFN) (4 mL, 0.93 mg/mL, in 20 mM Tris pH 8.0, ~100 mM NaCl, protease inhibitors, 1 mM EDTA, 10% Glycerol) was buffer exchanged into phosphate buffered saline (PBS), pH 7.4 using Zeba™ spin 5 mL columns. IFN was reduced by treatment with DTT (25 mM) for 30 min at 22° C. Reductant was removed using a PD10 desalting column equilibrated with PBS at pH 7.4. Reagents 3 and 41 (1.5 eq. per IFN sulfide) were conjugated to IFN (0.7 mg/mL) at 4° C. Samples of the reaction mixtures were analysed by SDS-PAGE after 1 h, 2 h and 4 h incubation. The % conversion to PEGylated IFN was estimated based on SDS-PAGE band density using an ImageQuant™ system (GE Healthcare). The results are shown in FIG. 2, which compares the conjugation efficiency of fluorescent reagent 4 possessing polymeric ethylene glycol leaving groups and an analogous reagent 41 lacking polymeric leaving groups. Reagent 3 reacted faster and produced a greater amount of IFN-PEG(10 kDa)-OMe (band corresponding to approximately 35 kDa), compared to the equivalent timepoint for reagent 41.

EXAMPLE 19

Figure 3:
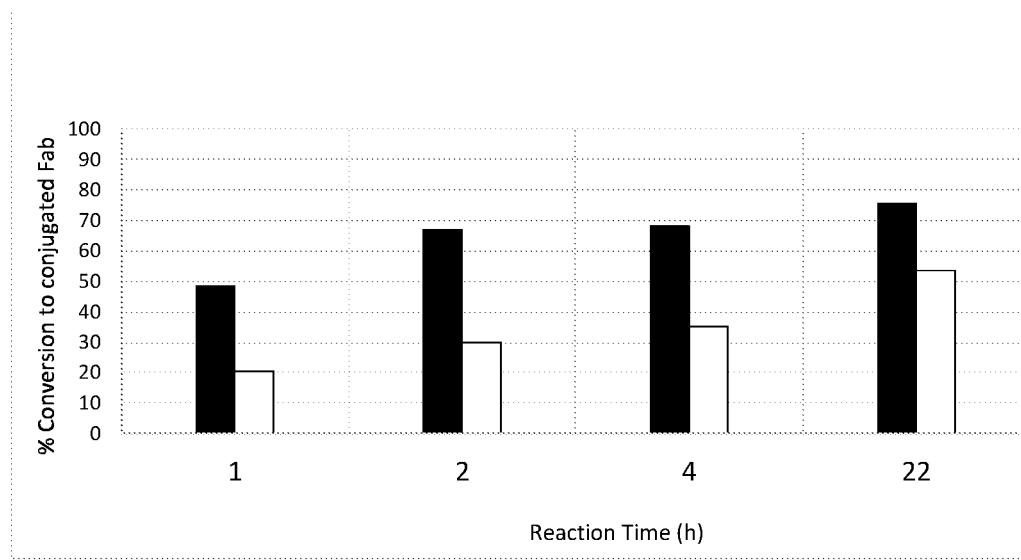
FIG. 3 shows the results of Example 19.

Comparison of the Conjugation Efficiency of Fluorescent Reagent 4 Possessing Polymeric Ethylene Glycol Leaving Groups and an Analogous Reagent 36 Lacking Polymeric Leaving Groups Using a similar conjugation method to that described in Example 17, reagents 4 and 36 were dissolved separately in 100% MeCN at 1.53 mg/mL and 1.67 mg/mL, respectively, prior to conjugation. To the Fab solution (1.24 mg/mL, 0.475 mL in PBS), reagent 4 or reagent 36 (18 μL) was added corresponding to 1.5 equivalents. The reaction was allowed to progress 22 h at 22° C. and samples were taken for SDS-PAGE analysis during the reaction. The % conversion to rhodamine-conjugated Fab was estimated based on SDS-PAGE band density using an ImageQuant™ system (GE Healthcare). The results are shown in FIG. 3, which compares the conversion to rhodamine conjugated Fab using reagent 4 (black bars) and reagent 36 (white bars), at 1.5 equivalents of reagent. Reagent 4 gave a higher conversion to conjugated Fab at each timepoint.

EXAMPLE 20

Comparison of the Antibody Conjugation of Cytotoxic Reagent 5 Possessing Polymeric Ethylene Glycol Leaving Groups with an Analogous Reagent 42 (4-[2,2-bis[(p-tolylsulfonyl)-methyl]acetyl]benzamide-val-cit-PAB-MMAE) Lacking Polymeric Leaving Groups Reagent 42 was synthesised as described within WO2014064423.

Figure 4:
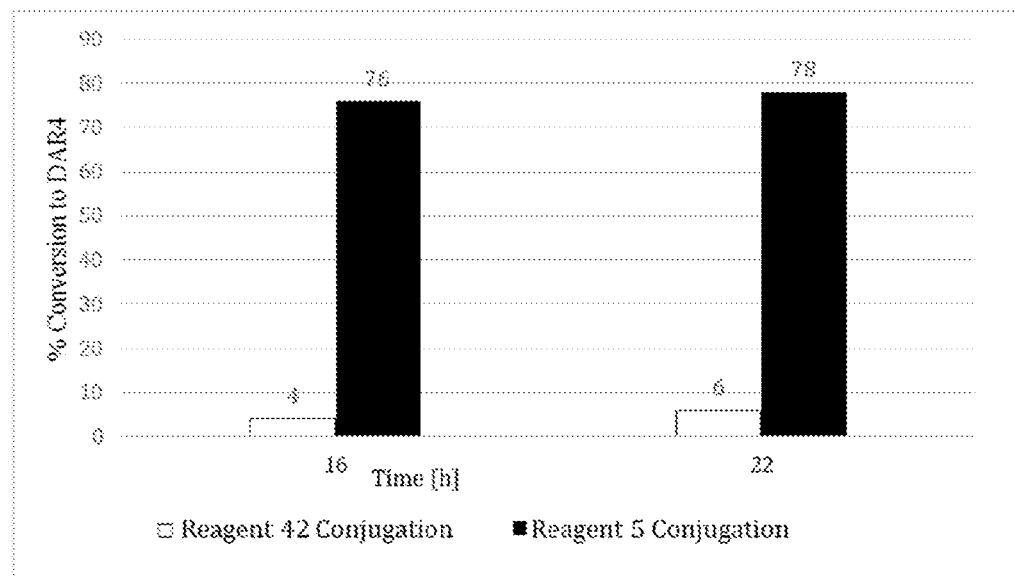
FIG. 4 shows the results of Example 20.

Both reagents 5 and 42 were conjugated to the antibody trastuzumab using an analogous method to the Examples described in WO2014064423. Briefly, trastuzumab (5.2 mg/mL) was reduced with tris(2-carboxyethyl)phosphine (TCEP) at 40° C. for 1 h. Conjugation of the antibody with 1.5 molar equivalents of either reagent 5 or 42 per interchain disulfide bond was then performed by dissolving both reagent 5 and reagent 42 in DMF to a final concentration of 1.6 mM. The antibody solution was diluted to 4.21 mg/mL with 20 mM sodium phosphate buffer, 150 mM NaCl, 20 mM EDTA, pH 7.5. Reagent 5 and 42 were added to separate aliquots of antibody. The final antibody concentration in the reaction was adjusted to 4 mg/mL with 20 mM sodium phosphate buffer, 150 mM NaCl, 20 mM EDTA, pH 7.5. Each solution was mixed gently and incubated at 22° C. for 22 h. At 16 and 22 h an aliquot was taken, treated with N-acetyl-L-cysteine (20 eq. over reagent) for 1 h at 22° C. and then analysed by HIC. The % conversion of product with a drug to antibody ratio (DAR) of four was determined based on the % area of the absorbance peaks measured at 280 nm from the HIC chromatograms and results are shown in FIG. 4, which shows the comparison of conjugation of reagents 5 (black bars) and 42 (white bars) to an antibody. The results in FIG. 4 show that 6% of DAR 4 conjugate was produced with reagent 42 after 22 h, whereas reagent 5 gave 78% of DAR 4 conjugate after 22 h.

EXAMPLE 21

Comparison of the Antibody Conjugation of Cytotoxic Reagents 5, 6 and 10 all Possessing Polymeric Ethylene Glycol Leaving Groups with Analogous Reagents 42, 43 and 44 Lacking Polymeric Leaving Groups Reagent 43 was synthesised as described within WO2014064423 and reagent 44 was synthesised as described within WO2014064424.

(a) Comparison of the antibody conjugation of cytotoxic reagent 43 (4-[2,2-bis[(p-tolylsulfonyl)-methyl]acetyl]benzamide-PEG(24u)-val-cit-PAB-MMAE) and reagent 5.

Figure 5:
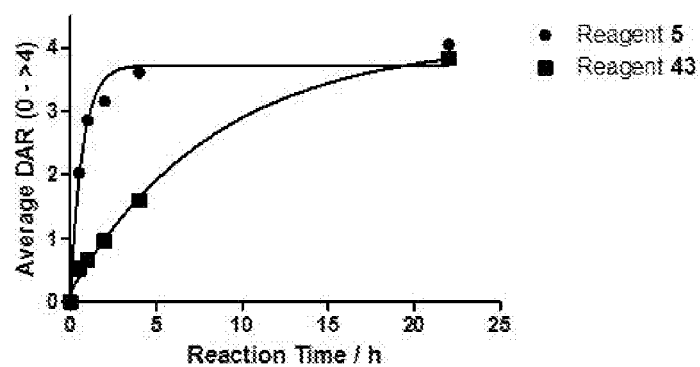
FIGS. 5, 6 and 7 show the results of Example 21.

The reaction conditions used for conjugation of cytotoxic reagent 43 with antibody (5 mg scale) were the same as those described above for Example 20 with the following differences: The reagents 43 and 5 were prepared as 3.2 mM MeCN solutions. Aliquots of reaction solution were taken after 0.5, 1, 2, 4 and 22 h, quenched by treatment with N-acetyl-L-cysteine (1 h at 22° C.), and analysed by HIC. The results of these conjugation reactions are shown in FIG. 5, which is a time course analysis comparing the rate of conjugation (Average DAR) for reagent 5 and reagent 43 over 22 h. In FIG. 5, it can be seen that the rate of product formation was much faster for reagent 5 than for reagent 43. The DAR 4 species were purified from each reaction mixture using HIC and analysed by SDS-PAGE. From SDS-PAGE analysis, the % of half antibody species present for each sample were determined by ImageQuant™ analysis of the stained gel and the result is shown in Table 1, where the conjugate prepared from reagent 43 had almost twice the amount of half antibody species as the conjugate produced from reagent 5. This indicates the conjugate produced from reagent 5 had significantly more heavy to heavy interchain covalent bonding and better resembles the structure of the unconjugated antibody.

TABLE 1

| Sample | % of half antibody species present by SDS-PAGE analysis (H + L chain species) |
|---|---|
| Trastuzumab-5 conjugate | 27% |
| Trastuzumab-43 conjugate | 47% |

(b) Comparison of the antibody conjugation of cytotoxic reagent 44 (4-[2,2-bis[(p-tolylsulfonyl)-methyl] acetyl] benzamide-PEG(24u)-val-ala-PAB-AHX-DM1) and reagent 10.

Figure 6:
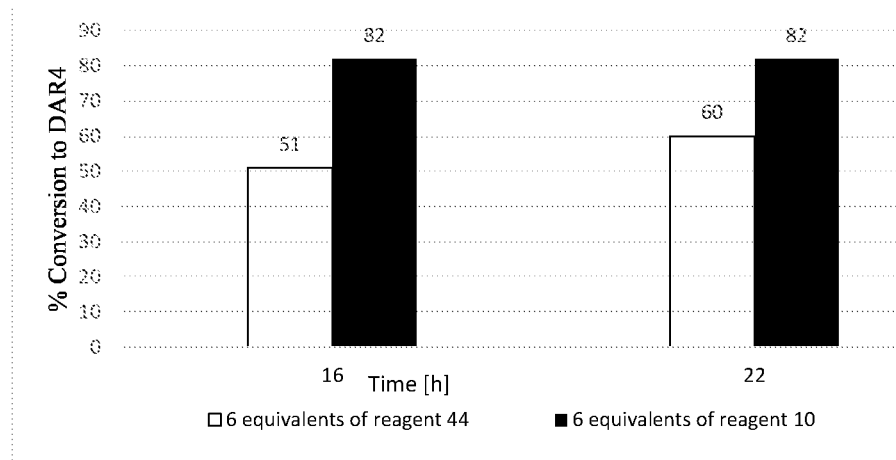

The reaction conditions used for conjugation of cytotoxic reagent 44 with antibody (3.8 mg scale) were the same as those described above for Example 20. An aliquot of reaction solution was taken after 16 and 22 h and quenched by treatment with N-acetyl-L-cysteine. Each aliquot was analysed by HIC and the % conversion to DAR 4 product determined. The result is shown in FIG. 6, which is a comparison of conjugation of reagents 10 (black bars) and 44 (white bars) to an antibody. It can be seen that reagent 10 gave more DAR 4 product after both 16 h and 22 h.

Figure 7:
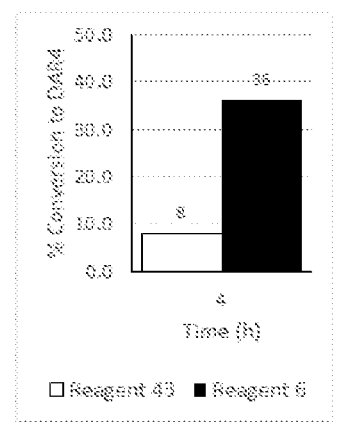

(c) Comparison of the antibody conjugation of cytotoxic reagent 43 (4-[2,2-bis[(p-tolylsulfonyl)-methyl]acetyl]benzamide-PEG(24u)-val-cit-PAB-MMAE) and reagent 6. The reaction conditions used for conjugation of cytotoxic reagent 6 with antibody (1 mg scale) were analogous to those described above for Example 20 with the following differences: Reagent 6 was prepared as a 3.2 mM MeCN solution and the MeCN concentration in the reaction was 5%. An aliquot of reaction solution was taken after 4 h, quenched by treatment with N-acetyl-L-cysteine, and analysed by analytical HIC and the % of DAR 4 product present determined. The results are shown in FIG. 7, which is a comparison of conjugation of reagents 6 (black bar) and 43 (white bar) to an antibody. It can be seen that reagent 6 (black bar) gave significantly more DAR 4 product after 4 h than reagent 43 (white bar).

EXAMPLE 22

Figure 8:
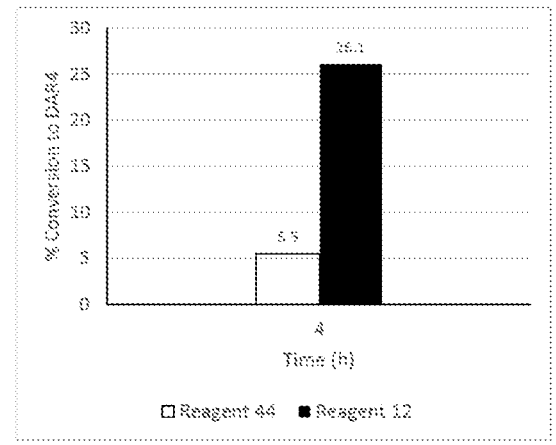
FIG. 8 shows the results of Example 22.

Comparison of the Antibody Conjugation of Cytotoxic Reagent 12 Possessing Polymeric Ethylene Glycol Leaving Groups with an Analogous Reagent 44 without Polymeric Leaving Groups The reaction conditions used for conjugation of cytotoxic reagent 12 with an antibody (1 mg scale) were the same as those described above for Example 20. An aliquot of reaction solution was taken after 4 h, quenched by treatment with N-acetyl-L-cysteine and analysed by HIC. The results are shown in FIG. 8, which is a comparison of conjugation of reagents 44 (white bar) and 12 (black bar) to an antibody. In FIG. 8, it can be seen that reagent 12 gave a significantly higher yield of the DAR 4 product after 4 h compared with reagent 44.

EXAMPLE 23

Comparison of the Antibody Conjugation of Cytotoxic Reagents 14, 15 and 31 Possessing Polymeric Ethylene Glycol Leaving Groups with an Analogous Reagent 44 without Polymeric Leaving Groups The reaction conditions used for conjugation of cytotoxic reagents 14, 15 and 31 with antibody (1 mg scale) were the same as those described above for Example 20. An aliquot of reaction solution was taken after 4 h and quenched by treatment with N-acetyl-L-cysteine. Each aliquot was analysed by HIC and the % of DAR 4 product present determined. Results for conjugation with reagents 14, 15, 31 and 44 are displayed in Table 2, where is can be seen that reagents 14, 15 and 31 gave over twice the amount of DAR 4 product compared to reagent 44 after 4 h.

TABLE 2

Comparison of conjugation of reagents 14, 15, 31 and 44 to an antibody after 4 h reaction.

| Reagent used for conjugation to an antibody | % DAR 4 product after 4 h |
|---|---|
| 44 | 9 |
| 14 | 24 |
| 15 | 23 |
| 31 | 28 |

EXAMPLE 24

Preparation of Antibody Drug Conjugates

Antibody drug conjugates were prepared from reagents 21, 24 and 25 by methods analogous to those described in WO2014064423 and WO2014064424. Briefly, antibody (trastuzumab or brentuximab) was reduced using tris(2-carboxyethyl)phosphine at 40° C. for 1 h. Conjugation of the antibody with 1.5 molar equivalents of reagent per interchain disulfide bond was then performed by dissolving reagents to a final concentration of 1.6 mM in either acetonitrile or DMF. The antibody solution was diluted to 4.21 mg/mL with 20 mM sodium phosphate buffer, 150 mM NaCl, 20 mM EDTA, pH 7.5. Reagents were added to antibody and the final antibody concentration in the reaction was adjusted to 4 mg/mL with 20 mM sodium phosphate buffer, 150 mM NaCl, 20 mM EDTA, pH 7.5. Each solution was mixed gently and incubated at 22° C. Antibody drug conjugate product was purified by hydrophobic interaction chromatography for each conjugate.

EXAMPLE 25

PEGylation of a Histidine-Tagged Interferon-Alpha using Reagent 3 at pH 6.6 and 7.9

Figure 9:
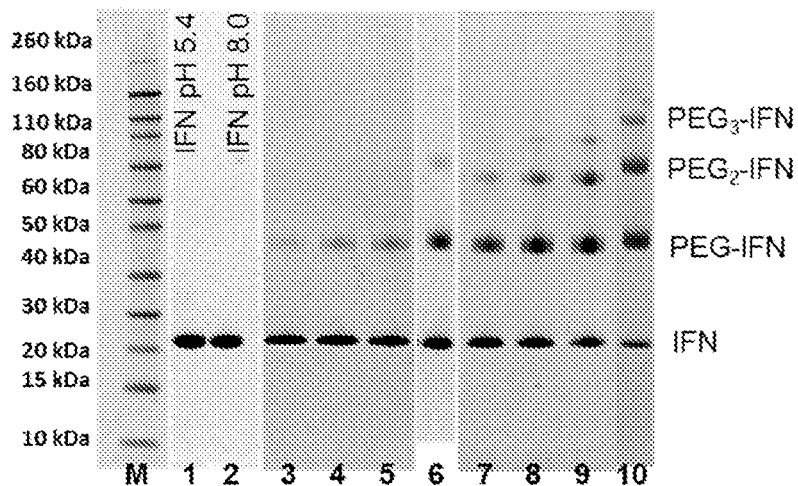
FIG. 9 shows the results of Example 25.

The conjugation of interferon α-2a (IFN) possessing an 8-histidine tag with reagent 3 was carried out at 2.5 mg/mL at either pH 6.6 or pH 7.9, achieved by mixing sodium acetate pH 5.3 or sodium phosphate pH 8.0 with sodium phosphate pH 7.4 respectively. Reagent 3 at 1, 1.5 and 2 eq. per IFN was used. The resulting reaction mixtures were incubated for 22 h at 22° C. with an interim analysis at 4 h. The reaction mixtures were analysed by SDS-PAGE and the results are shown in FIG. 9. In FIG. 9, Lane M indicates Novex Protein Standards; lane 1 indicates IFN at pH 5.4; lane 2 indicates IFN at pH 8.0; lanes 3-5 indicate conjugated product from 1, 1.5 and 2 eq. reagent 3 respectively at 4 h at pH 6.6; lane 6 indicates conjugated product from 1.5 eq. reagent 3 at 4 h, pH 7.9; lanes 7-9 indicate conjugated product from 1, 1.5 and 2 eq. reagent 3 respectively at 22 h at pH 6.6; lane 10 indicates conjugated product from 1.5 eq. reagent 3 respectively at 22 h at pH 7.9.

EXAMPLE 26
Synthesis of a Disulfide Bridging Reagent 45
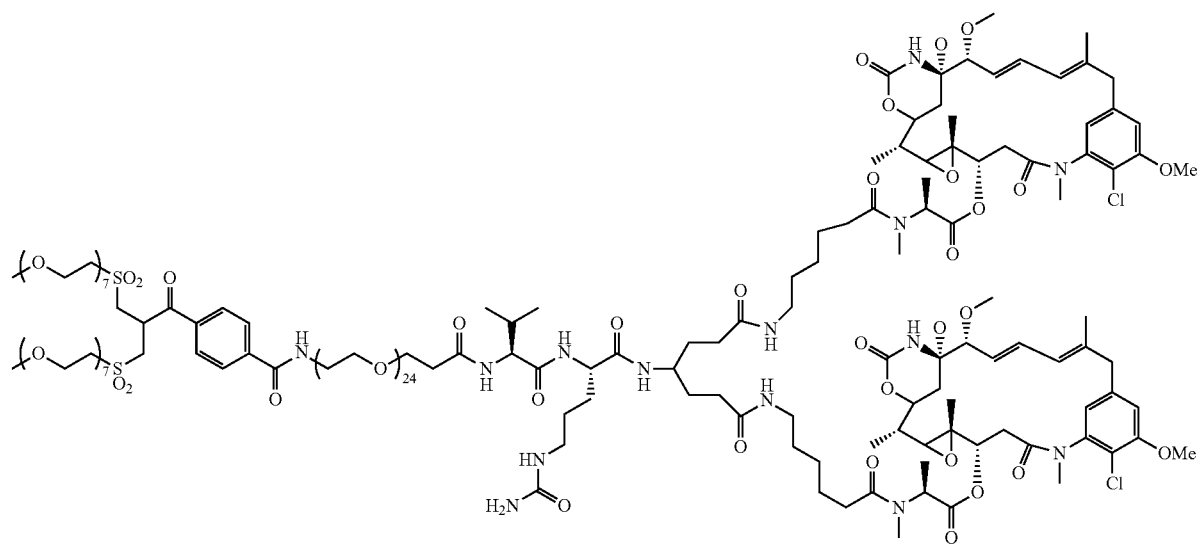
Step 1: Synthesis of Compound 46.
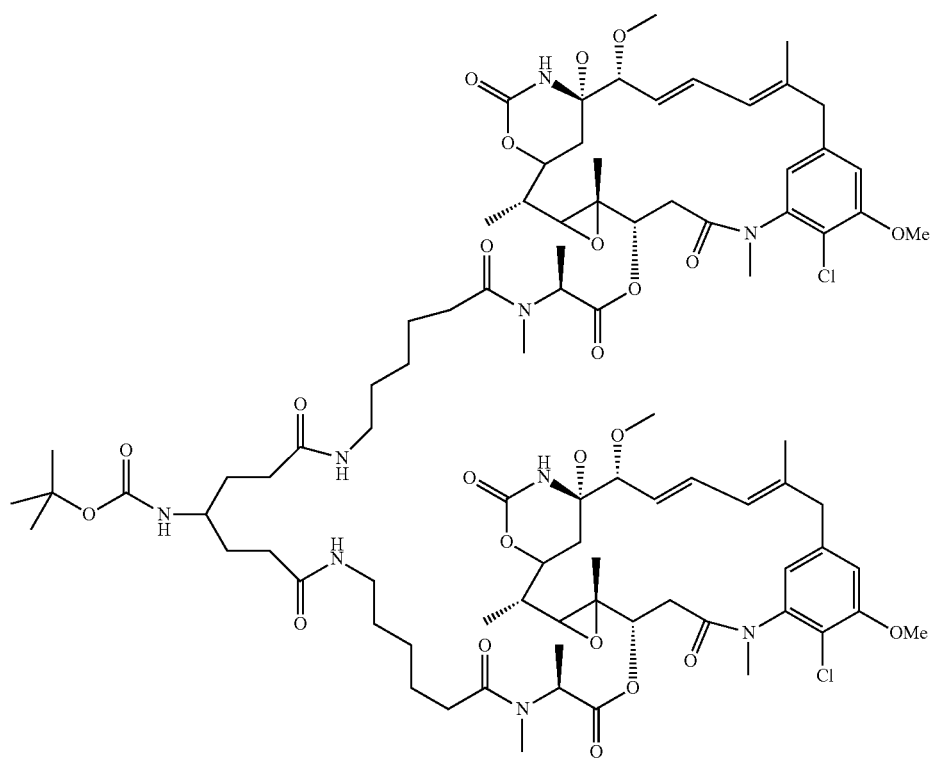

To a stirred solution of aminohexanoic maytansine (AHX-DM1).TFA salt (29.4 mg) of formula:

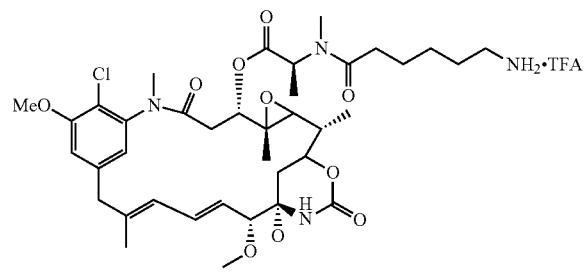

in dimethylformamide (DMF) (400 μL) was added a solution of 4-(N-Boc-amino)-1,6-heptanedioic acid bis-pentafluorophenyl ester (10.2 mg) in DMF (200 μL). The solution was cooled to 0° C. before addition of N,N-diisopropylethylamine (DIPEA) (13.5 μL). The solution was allowed to warm to room temperature and stirred for 18.5 h. The reaction solution was purified by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 0:100 v/v). The solvent was removed by lyophilisation to give 4-(N-boc-amino)-1,6-heptanediamide bis-AHX-DM1 compound 46 (assumed quantitative yield, 29.7 mg) as a white solid m/z [M+2H−2(H$_2$O)—NHCO]$^{2+}$ 844 (100%), [M+H]$^+$ 1767.

Step 2: Synthesis of Cytotoxic Payload 47.

Compound 46 (assumed quantitative yield, 29.7 mg) was dissolved in formic acid (700 μL) and the solution stirred at room temperature for 1.5 h. Volatiles were removed in vacuo and the residue converted to the trifluroacetic acid salt by dissolving in a buffer A:buffer B 50:50 v/v % mixture (1.5 mL, buffer A (v/v): water:5% acetonitrile:0.05% trifluoroacetic acid and buffer B (v/v): acetonitrile:0.05% trifluoroacetic acid). The solution was stirred at room temperature for 5 min before the solvent was removed by lyophilisation. The process was repeated to give 4-(amino)-1,6-heptanediamide bis-AHX-DM1 compound 47 as an off-white solid (18.0 mg, 60% over 2 steps) m/z [M+2H−2(H$_2$O)—NHCO]$^{2+}$ 794 (100%), [M+H]$^+$ 1667.

Step 3: Synthesis of Compound 48.

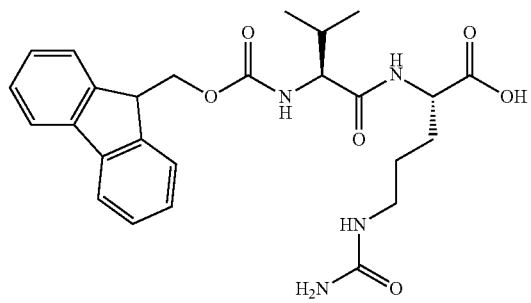

48

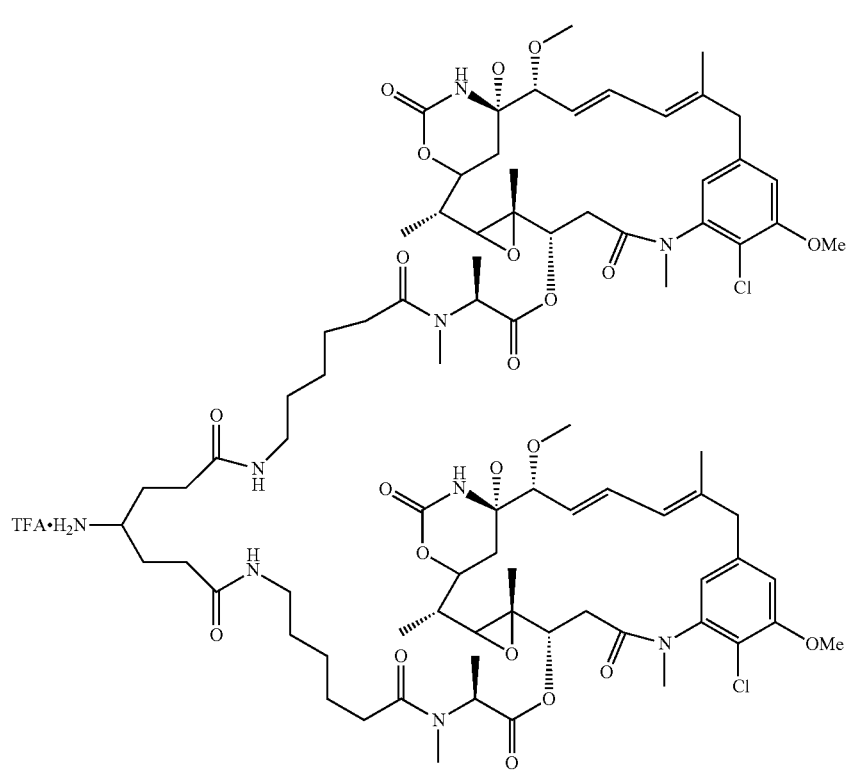

47

Compound 48 was synthesised following the procedure described in patent (EP 0 624 377 A2) to give a white solid with spectroscopic data in agreement with that previously reported.

Step 4: Synthesis of Compound 49.

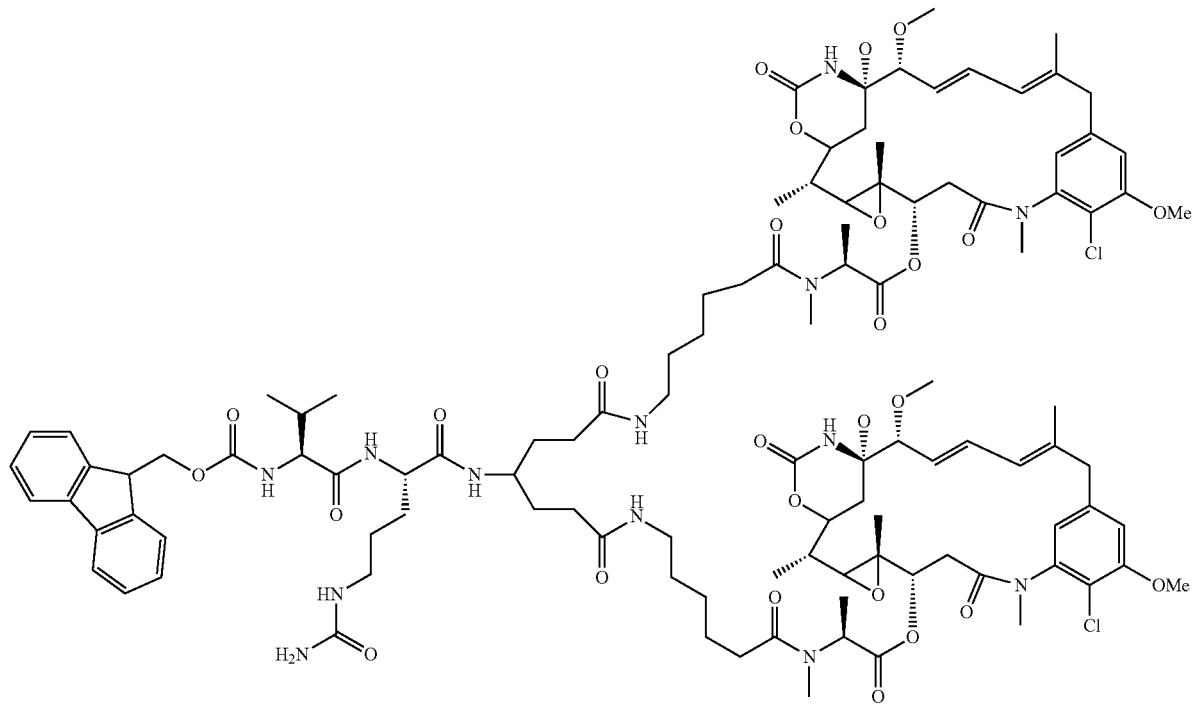

Stock solutions of compound 48 (20.0 mg) in DMF (500 µL) and HATU (40.0 mg) in DMF (400 µL) were prepared. To a stirred solution of compound 47 (14.0 mg) in DMF (700 µL) was added aliquots of compound 48 stock solution (126.9 µL) and HATU stock solution (77.8 µL). The reaction solution was cooled to 0° C. before the addition of DIPEA (4.11 µL). The solution was stirred at 0° C. for 50 min before further aliquots of compound 48 stock solution (126.9 µL), HATU stock solution (77.8 µL) and DIPEA (4.11 µL) were added. The solution was stirred for 40 min at 0° C. The reaction solution was purified by reverse phase C18-column chromatography eluting with buffer A (v/v): water:0.05% trifluoroacetic acid and buffer B (v/v): acetonitrile:0.05% trifluoroacetic acid (100:0 v/v to 0:100 v/v). The solvent was removed by lyophilisation to give 4-(Fmoc-val-cit-amido)-1,6-heptanediamide bis-AHX-DM1 compound 49 (assumed quantitative yield, 16.9 mg) as an off-white solid m/z $[M+2H-2(H_2O)]^{2+}$ 1055 (100%).

Step 5: Synthesis of Compound 50.

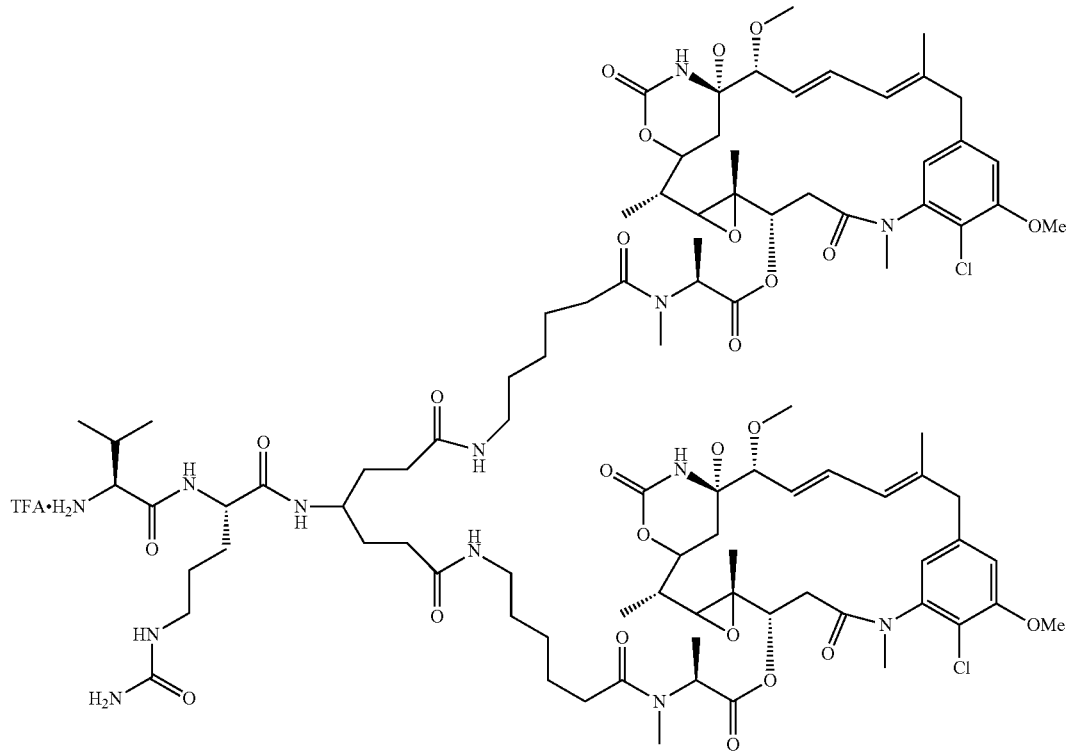

To a stirred solution of compound 49 (assumed quantitative yield, 16.9 mg) in DMF (500 μL) was added piperidine (3.04 μL). The reaction solution was stirred at room temperature for 1.5 h before purification by reverse phase C18-column chromatography eluting with buffer A (v/v): water:0.05% trifluoroacetic acid and buffer B (v/v): acetonitrile:0.05% trifluoroacetic acid (100:0 v/v to 0:100 v/v). The solvent was removed by lyophilisation to give 4-(val-cit-amido)-1,6-heptanediamide bis-AHX-DM1 compound 50 as an off-white solid (8.8 mg, 55% over 2 steps) m/z $[M+2H]^{2+}$ 962 (100%).

Step 6: Synthesis of Disulfide Bridging Reagent 45 Comprising the Cytotoxic Payload 47.

Stock solutions of compound 8 (13.5 mg) in DMF (100 μL), HATU (10.0 mg) in DMF (200 μL) and NMM (5.83 μL) in DMF (94.2 μL) were prepared. To a stirred solution of 50 (1.8 mg) in DMF (80 μL) was added aliquots of compound 23 stock solution (16.5 μL) and HATU stock solution (20.2 μL). The reaction solution was cooled to 0° C. before adding an aliquot of NMM stock solution (5 μL). The solution was allowed to stir at 0° C. for 1 h before warming to room temperature. After 3.5 h, the reaction solution was purified by reverse phase C18-column chromatography eluting with buffer A (v/v): water:0.05% trifluoroacetic acid and buffer B (v/v): acetonitrile:0.05% trifluoroacetic acid (100:0 v/v to 0:100 v/v). The solvent was removed by lyophilisation to give bis-mPEG(7u)sulfone-propanoyl-benzamide-val-cit-amido)-1,6-heptanediamide bis-AHX-DM1 reagent 45 as a solid (1.5 mg, 42%) m/z $[M+4H-2(H_2O)]^{4+}$ 992 (100%), $[M+3H-2(H_2O)]^{3+}$ 1321, $[M+2H-2(H_2O)]^{2+}$ 1982.

EXAMPLE 27

Synthesis of a Disulfide Bridging Reagent 51 Comprising the Cytotoxic Payload 47

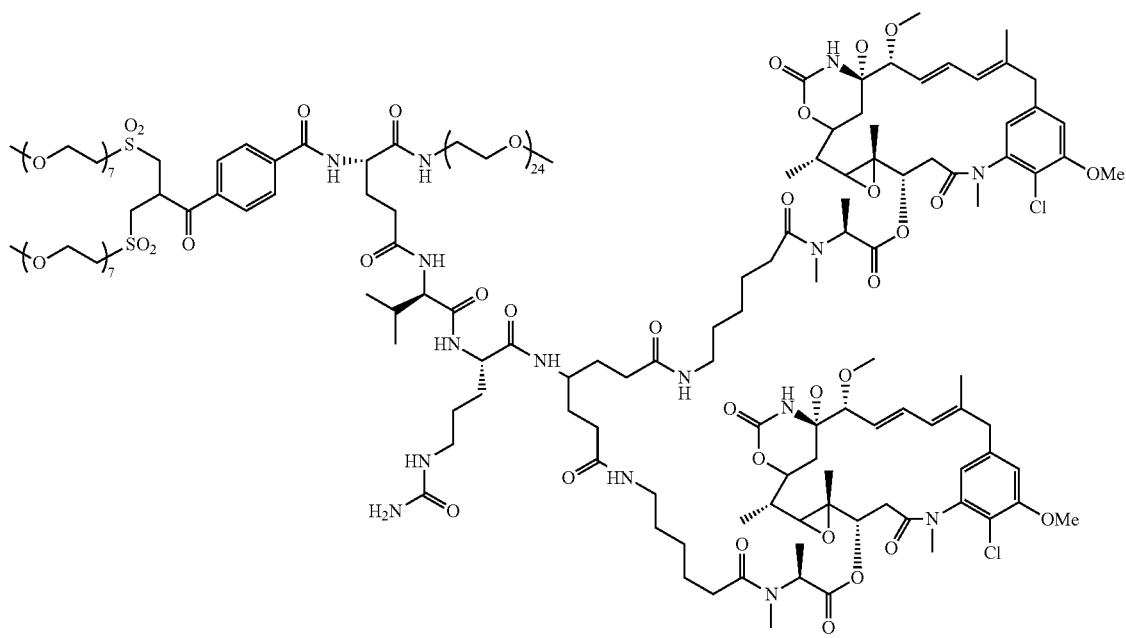

Step 1: Synthesis of Reagent 51.

Stock solutions of HATU (10 mg) in DMF (200 µL) and NMM (5.83 µL) in DMF (94.2 µL) were prepared. Compound 23 (5.4 mg) was dissolved in a solution of compound 50 (3.6 mg) in DMF (254 µL) with stirring. To the stirred solution was added an aliquot of HATU stock solution (40 µL). The solution was cooled to 0° C. before an aliquot of NMM stock solution (10 µL) was added. After 50 min, further aliquots of HATU stock solution (6.67 µL) and NMM stock solution (1.67 µL) were added. The reaction solution was stirred at 0° C. for a further 20 minutes and purified directly by reverse phase C18-column chromatography eluting with buffer A (v/v): water:0.05% trifluoroacetic acid and buffer B (v/v): acetonitrile:0.05% trifluoroacetic acid (100:0 v/v to 0:100 v/v). The solvent was removed by lyophilisation to give reagent 51 as an off-white solid (3.8 mg, 53%) m/z [M+4H−($H_2O$)—NHCO]$^{4+}$ 1003 (100%), [M+3H−2($H_2O$)—NHCO]$^{3+}$ 1331, [M+2H−2($H_2O$)]$^{2+}$ 2017.

EXAMPLE 28

Synthesis of a Disulfide Bridging Reagent 56 Comprising the Cytotoxic Payload 47

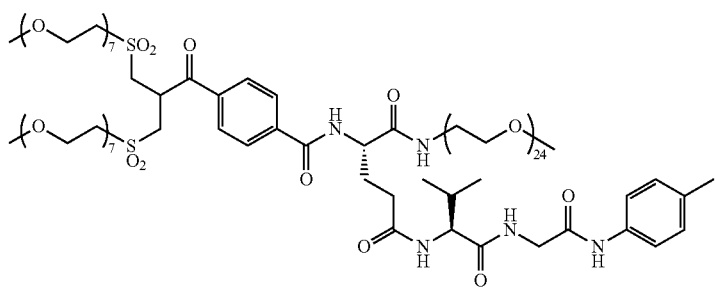

-continued

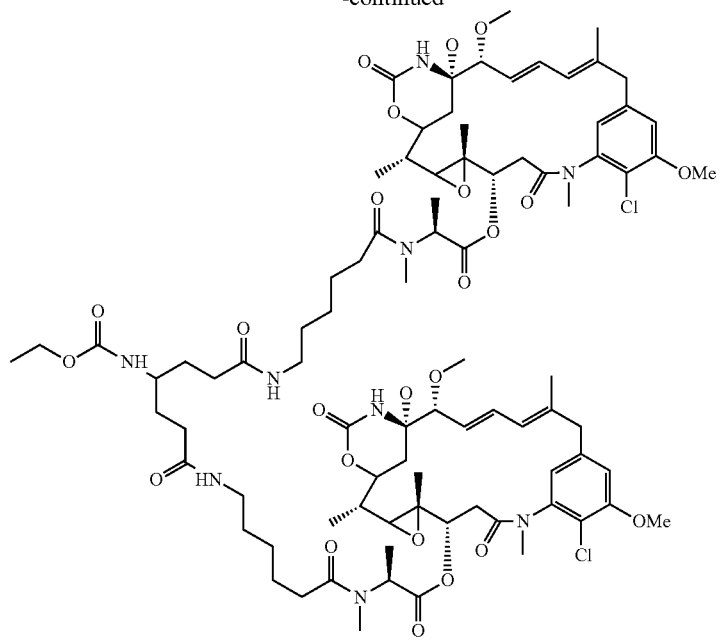

Step 1: Synthesis of Compound 57.

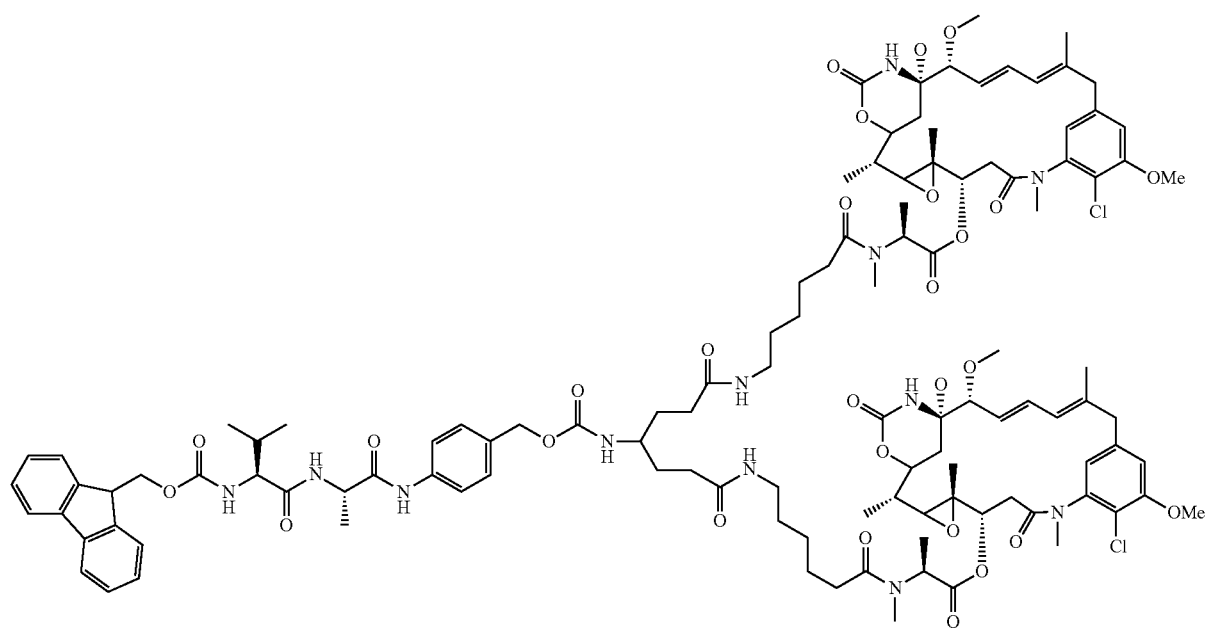

57

A stock solution of hydroxybenzotriazole (HOBt, 6.6 mg) in DMF (200 µL) was prepared. To a stirred solution of cytotoxic payload 47 (10 mg) in DMF (500 µL) was added Fmoc-val-ala-PAB-PNP (3.7 mg) and an aliquot of HOBt stock solution (2 µL). The reaction solution was cooled to 0° C. before DIPEA (2.14 µL) was added. The reaction solution was then stirred at room temperature for 18 h before purification by reverse phase C18-column chromatography, eluting with buffer A (v/v): water:0.05% trifluoroacetic acid and buffer B (v/v): acetonitrile:0.05% trifluoroacetic acid (100:0 v/v to 0:100 v/v). The solvent was removed by lyophilisation to give Fmoc-val-ala-PAB-amido-1,6-heptanediamide bis-AHX-DM1 reagent 57.

60

Step 2: Synthesis of Compound 58.

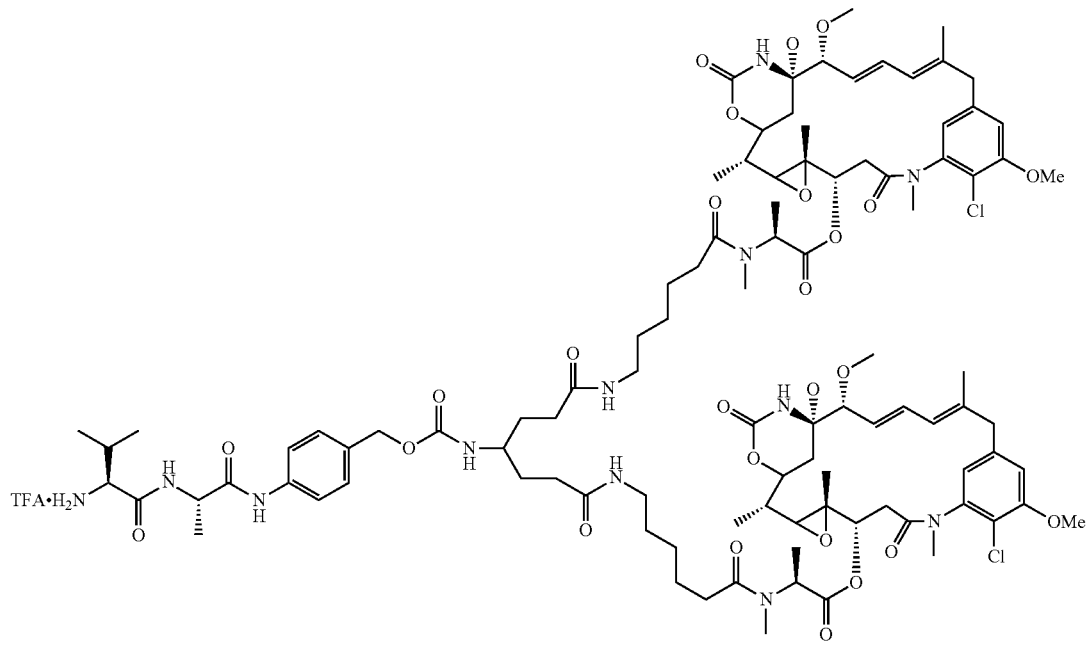

The bis-maytansinoid compound amine-val-ala-PAB-amido-1,6-heptanediamide bis-AHX-DM1 compound 58 was synthesised in an analogous way to that described for compound 50 using compound 57 instead of compound 49.

Step 3: Synthesis of Reagent 56.

The bis-maytansinoid reagent bis-mPEG(7u)sulfone-propanoyl-benzamide-Glu-[NH-PEG(24u)-OMe]-[val-ala-PAB-amido-1,6-heptanediamide bis-AHX-DM1] 56 was synthesised in an analogous way to that described for reagent 51, using compound 58 instead of compound 50.

EXAMPLE 29

Synthesis of a Disulfide Bridging Reagent 59 Comprising the Cytotoxic Payload AHX-DM1

To a stirred solution of val-cit-AHX-DM1 (5.0 mg) in anhydrous DMF (400 µL) was added reagent 8 (13 mg) and stirred for 5 min at 0° C. HATU (2.62 mg) and NMM (0.44 mg) were added in succession and the reaction mixture was allowed to stir at 0° C. After 20 min, an additional amount of HATU (2.62 mg) and NMM (0.44 mg) was added and the reaction mixture was stirred at 0° C. After 2.5 h, the reaction was cooled to −20° C. for 16 h. The reaction solution was concentrated in vacuo and then purified by reverse phase C18-column chromatography eluting with buffer A (v/v): water:5% acetonitrile: 0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give the bis-mPEG(7u)sulfone-propanoyl-benzamide-PEG(24u)-val-cit-AHX-DM1 reagent 59 as thick yellow oil (5.6 mg, 41%) m/z $[M-OH+H]^{2+}$ 1571.5.

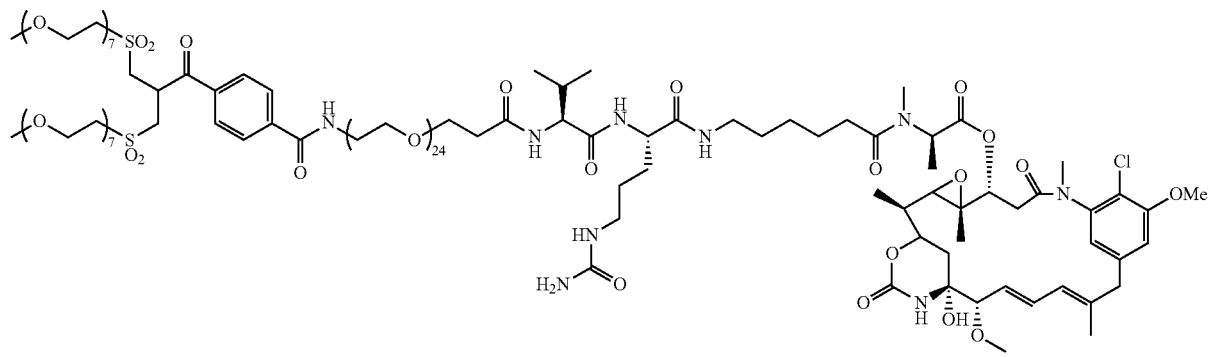

EXAMPLE 30

Production of Antibody Drug Conjugate 60 using Disulfide Bridging Reagent 45; Antibody Drug Conjugate 61 using Disulfide Bridging Reagent 51 and Antibody Drug Conjugate 62 using Disulfide Bridging Reagent 56

Antibody drug conjugates were prepared by methods analogous to those described in WO2014064423 and WO2014064424. Briefly, antibody (trastuzumab or brentuximab) was reduced using tris(2-carboxyethyl)phosphine at 40° C. for 1 h. Conjugation of the antibody with 1.5 molar equivalents of reagent (i.e., 45, 51 or 56) per inter-chain disulfide bond was then performed by dissolving reagents to a final concentration of 1.6 mM in either acetonitrile or DMF. The antibody solution was diluted to 4.21 mg/mL with 20 mM sodium phosphate buffer, 150 mM NaCl, 20 mM EDTA, pH 7.5. Reagents were added to antibody and the final antibody concentration in the reaction was adjusted to 4 mg/mL with 20 mM sodium phosphate buffer, 150 mM NaCl, 20 mM EDTA, pH 7.5. Each solution was mixed gently and incubated at 22° C. Antibody drug conjugate product was purified by hydrophobic interaction chromatography for each conjugate to give products with a defined drug to antibody ratio (DAR). The % conversion to DAR4 product for reagents 45, 41 and 56 were 30%, 65% and 40%, respectively, as determined by HIC.

EXAMPLE 31

Synthesis of a PEG Conjugation Reagent 63 Comprising 7 Repeat Unit Ethylene Glycol Leaving Groups and Fluorinated Aryl Linker

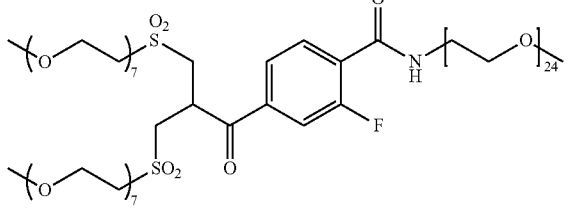

63

Step 1: Synthesis of Compound 64:

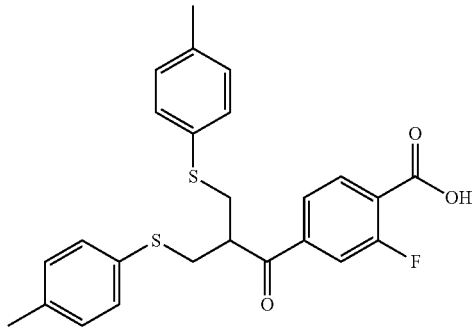

64

Formaldehyde (37% solution) (144 µL), piperidine (14.4 µL), and piperidine hydrochloride (134 mg) was added to a mixture of 4-acetyl-2-fluorobenzoic acid (200 mg) and 4-methylbenzene thiol (272 mg) in absolute ethanol (1.5 mL). The reaction mixture was heated at reflux for 2.5 h, during which time a further portion of formaldehyde (37% solution) (144 µL) was added (after 1.5 h). The reaction mixture was then cooled to room temperature and stirred overnight. Additional quantities of formaldehyde (37% solution) (288 µL) and piperidine (14.4 µL) were added and the reaction mixture was heated under reflux for a further 8 h. The reaction mixture was then cooled to room temperature and stirred overnight. Volatiles were removed in vacuo. The resulting residue was dissolved in water:acetonitrile (800 µL, 1:3 v/v) and purified by reverse phase C18-column chromatography eluting with buffer A (v/v): water: 0.05% trifluoroacetic acid and buffer B (v/v): acetonitrile:0.05% trifluoroacetic acid (98:2 v/v to 0:100 v/v). The organic solvent was removed in vacuo and the aqueous solvent was removed by lyophilisation to give bis-(methyl benzene sulfide propanoyl)-2-fluoro-benzoic acid compound 64 as pale orange crystals (196.0 mg, 39%) m/z [M+H]$^+$ 454.20 Da; $^1$H NMR (400 MHz, CDCl$_3$) 2.35 (6H, s, OMe), 3.20-3.30 (4H, m, CH$_2$), 3.70-3.80 (1H, m, CH), 7.10 (4H, d, Ar—H), 7.15 (4H, d, Ar—H), 7.20 (1H, s, Ar—H), 7.35 (1H, d, Ar—H), 7.90 (1H, t, Ar—H).

Step 2: Synthesis of Compound 65:

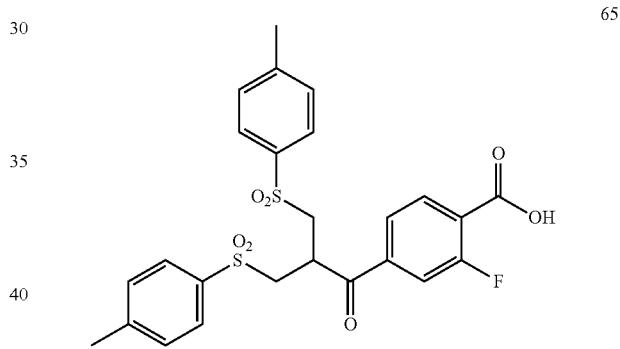

65

To a stirred solution of compound 64 (75 mg) in methanol:water (2.0 mL, 9:1 v/v) at room temperature was added Oxone® (304 mg, Sigma-Aldrich). After 2 h, the volatiles were removed in vacuo. The resulting residue was dissolved in dichloromethane (3×5.0 mL), filtered through a column of magnesium sulfate and washed with dichloromethane (2×5 mL). The eluent and washings were combined and the volatiles were removed in vacuo to give bis-(tosyl propanoyl)-2-fluoro-benzoic acid compound 65 as a white powder (84.0 mg, 98%) m/z [M–H]$^+$ 519.15 Da.

Step 3: Synthesis of Compound 66:

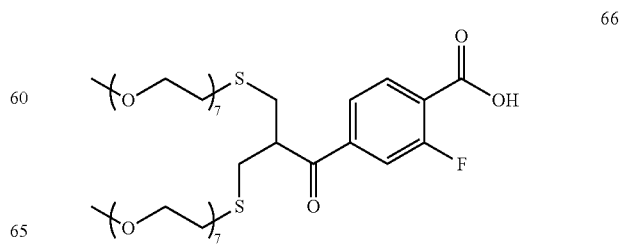

66

To a solution of compound 65 (75 mg) in DMF (2.0 mL) was added Et₃N (240 µL, Acros Organics) and MeO-PEG-(7u)-SH (154 mg, Iris Biotech). The reaction was stirred under an inert nitrogen atmosphere at room temperature. After 6 h, volatiles were removed in vacuo. The resulting residue was dissolved in water: acetonitrile (2.0 mL, 1:1 v/v) and purified by reverse phase C18-column chromatography eluting with buffer A (v/v): water: 0.05% trifluoroacetic acid and buffer B (v/v): acetonitrile:0.05% trifluoroacetic acid (98:2 v/v to 0:100 v/v). The organic solvent was removed in vacuo and the aqueous solvent was removed by lyophilisation to give bis-mPEG(7u)-sulfide-propanoyl-2-fluoro-benzoic acid compound 67 as colourless oil (101 mg, 78%) m/z [M–H]⁺ 919.45 Da.

Step 4: Synthesis of Compound 67:

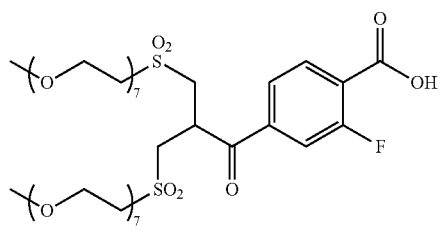

67

To a stirred solution of compound 66 (80 mg) in methanol:water (2.0 mL, 9:1 v/v) at room temperature was added Oxone® (160 mg, Sigma-Aldrich). After 3 h, the volatiles were removed in vacuo. The resulting residue was dissolved in dichloromethane (3×4 mL), filtered through a column of magnesium sulfate and washed with dichloromethane (2×5 mL). The eluent and washings were combined and the volatiles were removed in vacuo. The resulting oil was dissolved in water and lyophilised to give bis-mPEG(7u)-sulfone-propanoyl-2-fluoro-benzoic acid compound 67 as a clear colourless oil (82 mg, 95%) m/z [M+H]⁺ 983.26 Da.

Step 5: Synthesis of Compound 63:

Stock solutions of HATU (40.0 mg, Novabiochem) in DMF (200 µL) and NMM (11.8 µL, Acros Organics) in DMF (200 µL) were prepared. To a DMF (800 µL) solution of compound 67 (25.0 mg) was added H2N-PEG(24u)-OMe (23.4 mg, Iris Biotech). The resulting reaction mixture was stirred at room temperature under an inert nitrogen atmosphere. Aliquots of HATU (40.0 4) and NMM (40.0 µL) were added every 10 min for a total of 3 additions and the remaining aliquots of HATU (80.0 µL) and NMM (80.0 µL) were added at 30 min. After 60 min, volatiles were removed in vacuo. The resulting residue was dissolved in water (1.0 mL) and purified by reverse phase C18-column chromatography eluting with buffer A (v/v): water: 0.05% trifluoroacetic acid and buffer B (v/v): acetonitrile:0.05% trifluoroacetic acid (98:2 v/v to 0:100 v/v). The organic solvent was removed in vacuo and the aqueous solvent was removed by lyophilisation to give bis-mPEG(7u)-sulfone-propanoyl-2-fluoro-benzamide-PEG(24u) reagent 63 as a clear colourless oil (17.5 mg, 40%) m/z [M+3H]³⁺ 684.94 Da.

EXAMPLE 32

Synthesis of a PEG Conjugation Reagent 68 Comprising 7 Repeat Unit Ethylene Glycol Amino Leaving Groups

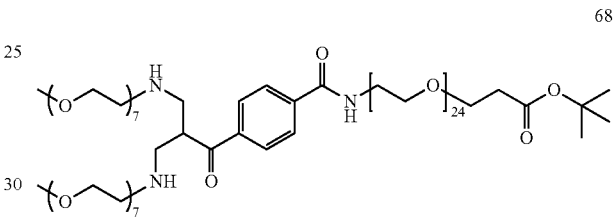

68

Step 1: Synthesis of Compound 69.

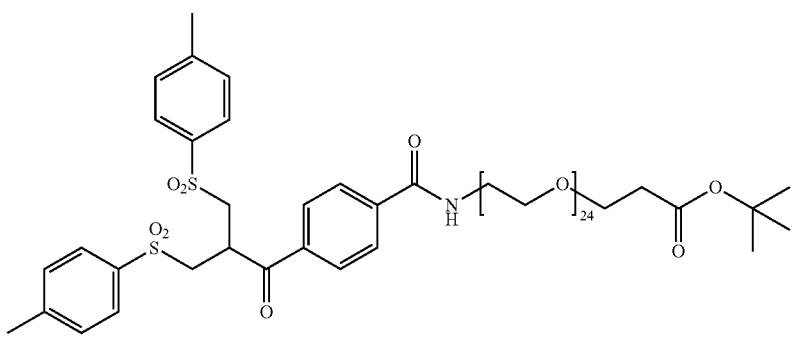

69

Stock solutions of HATU (632 mg, Novabiochem) in DMF (1.6 mL) and NMM (183 µL, Acros Organics) in DMF (1.6 mL) were prepared. To a DMF (4.0 mL) solution of 4-(3-tosyl-2-(tosylmethyl)propanoyl)benzoic acid (199 mg, BioVectra) was added H2N-PEG(24u)-CO₂ᵗBu (400.0 mg, Iris Biotech). The resulting reaction mixture was stirred at room temperature under an inert nitrogen atmosphere. Aliquots of HATU (320 µL) and NMM (320 µL) were added every 10 min for a total of 5 additions. After 120 min, volatiles were removed in vacuo. The resulting residue was dissolved in water:acetonitrile (2.0 mL, 1:3 v/v) and purified by reverse phase C18-column chromatography eluting with buffer A (v/v): water: 0.05% trifluoroacetic acid and buffer B (v/v): acetonitrile:0.05% trifluoroacetic acid (98:2 v/v to 0:100 v/v). The organic solvent was removed in vacuo and the aqueous solvent was removed by lyophilisation to give bis-(tosyl propanoyl)-benzamide-PEG(24u)-$^t$Butyl ester compound 69 as a clear orange oil (184 mg, 33%) m/z [M+Na+H]$^{2+}$ 853.43 Da, [M−(tBu)+2H]$^{2+}$ 814.83 Da.

Step 2: Synthesis of Compound 68.

To a solution of 69 (32 mg) in DMF (500 µL) was added anhydrous sodium carbonate (24.1 mg, Fisher Scientific) and MeO-PEG-(7u)-NH$_2$ (19 mg, Iris Biotech). The reaction was stirred at room temperature under an inert nitrogen atmosphere. After 18 h, volatiles were removed in vacuo. The resulting residue was dissolved in water (1.0 mL) and purified by reverse phase C18-column chromatography eluting with buffer A (v/v): water: 0.05% trifluoroacetic acid and buffer B (v/v): acetonitrile:0.05% trifluoroacetic acid (98:2 v/v to 0:100 v/v). The organic solvent was removed in vacuo and the aqueous solvent was removed by lyophilisation to give bis-mPEG(7u)-amino-propanoyl-benzamide-PEG(24u)-$^t$Butyl ester reagent 68 as a clear colourless oil (15.0 mg, 38%) m/z [M+2H]$^{2+}$ 1026.09 Da, [M+3H]$^{3+}$ 665.45 Da.

EXAMPLE 33

Synthesis of a Conjugation Reagent 70 Comprising Maleimide Unit, 7 Repeat Unit Ethylene Glycol Leaving Groups

70

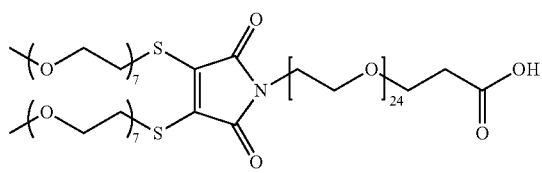

Step 1: Synthesis of Compound 71.

71

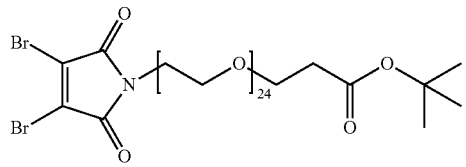

3,4-dibromofuran-2,5-dione (300 mg, Sigma Aldrich) was dissolved in acetic acid (4.0 mL, Fisher Scientific) and to this was added CO$_2$$^t$Bu-PEG-(24u)-NH$_2$ (705 mg, Iris Biotech). The reaction was stirred at 75° C. under an inert nitrogen atmosphere. After 3 h the reaction was stirred at room temperature and after 21 h, volatiles were removed in vacuo. The resulting residue was dissolved in water and acetonitrile (v/v; 1/1, 4.0 mL) and purified by reverse phase C18-column chromatography eluting with buffer A (v/v): water: 0.05% trifluoroacetic acid and buffer B (v/v): acetonitrile:0.05% trifluoroacetic acid (98:2 v/v to 0:100 v/v). The organic solvent was removed in vacuo and the aqueous solvent was removed by lyophilisation to give dibromo-maleimide-PEG(24u)-$^t$Butyl ester compound 71 as an off white opaque solid (427 mg, 51%) m/z [MH−($^t$Bu)]$^{2+}$ 692.68 Da.

Step 2: Synthesis of Compound 70.

To a solution of 71 (250 mg) in DMF (1.5 mL) was added alpha-methoxy-omega-mercapto hepta(ethylene glycol) (186 mg, Iris Biotech) and triethylamine (145 µL). The resulting reaction mixture was stirred under an inert nitrogen atmosphere at room temperature. Rapidly precipitated triethylamine hydrobromide was redissolved into the reaction mixture with DMF (1.0 mL) and after 30 min volatiles were removed in vacuo. The resulting residue was dissolved in formic acid (3 mL, Sigma Aldrich) and the reaction mixture was stirred under an inert nitrogen atmosphere at room temperature. After 30 min trifluoroacetic acid (50 µL, Acros Organics) was added and after 60 min more trifluoroacetic acid (300 µL) was added. After 100 min, volatiles were removed in vacuo. The resulting residue was dissolved in water (1.5 mL) and purified by reverse phase C18-column chromatography eluting with buffer A (v/v): water: 0.05% trifluoroacetic acid and buffer B (v/v): acetonitrile:0.05% trifluoroacetic acid (98:2 v/v to 0:100 v/v). The organic solvent was removed in vacuo and the aqueous solvent was removed by lyophilisation to give bis-mPEG(7u)-maleimide-PEG(24u)-acid reagent 70 as a waxy yellow solid (146 mg, 43%) m/z [MH$_3$]$^{3+}$ 646.28 Da.

EXAMPLE 34

Synthesis of a Conjugation Reagent 72 Comprising 7 Repeat Unit Ethylene Glycol Leaving Group and an Auristatin Cytotoxic Payload

72

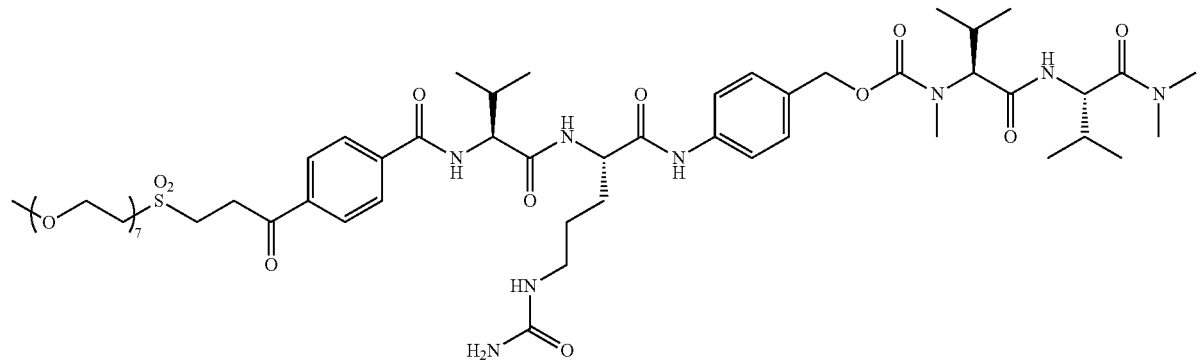

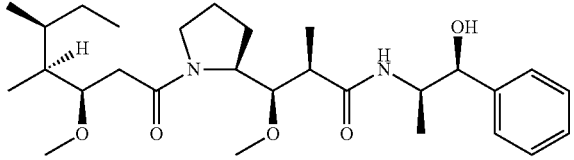

Step 1: Synthesis of Compound 73.

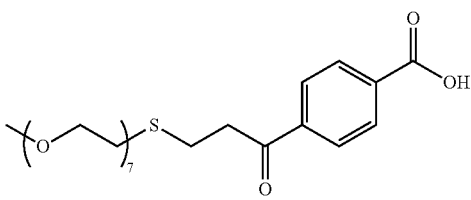

To a stirred solution of 4-(3-tosylpropanoyl)benzoic acid (99 mg, *Bioconjugate Chem.* 2014, (25) 460-469) in dimethylformamide (DMF, 5.0 mL) was added alpha-methoxy-omega-mercapto hepta(ethylene glycol) (170 mg, Iris Biotech) and triethylamine (250 µL). The resulting reaction mixture was stirred under an inert nitrogen atmosphere at room temperature. A further portion of triethylamine (120 µL) was added to the reaction mixture after 4 h. Volatiles were removed in vacuo after 95.0 h and the resulting residue was dissolved in water/acetonitrile (2 mL, 1:1 v/v) and purified by reverse phase C18-column chromatography eluting with buffer A (v/v): water:5% acetonitrile: 0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give mPEG(7u)-sulfide-propanoyl-benzoic acid compound 73 as a white solid (200 mg, 126%, with residual solvent) m/z [M+H]$^+$ (533).

Step 2: Synthesis of Compound 74.

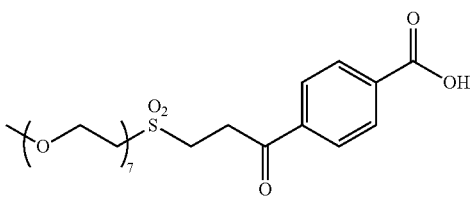

To a stirred solution of 73 (200 mg) in methanol:water (5.5 mL, 9:1 v/v) at room temperature was added Oxone® (320 mg). After 4.5 h, the volatiles were removed in vacuo. The resulting residue was dissolved in dichloromethane (4×3 mL), filtered through a column of magnesium sulfate and washed with dichloromethane (2×3 mL). The eluent and washings were combined and the volatiles were removed in vacuo to give a thick clear oil. The residue was dissolved in water:acetonitrile (1.0 mL, 4:1 v/v), and purified by reverse phase C18-column chromatography eluting with buffer A (v/v): water:5% acetonitrile:0.05% trifluoroacetic acid and buffer B (v/v): acetonitrile:0.05% trifluoroacetic acid (100:0 v/v to 0:100 v/v). The organic solvent was removed in vacuo and the aqueous solvent was removed by lyophilisation to give mPEG(7u)-sulfone-propanoyl-benzoic acid reagent 74 as a white solid (90 mg, 60%) m/z [M+H]$^+$ (565).

Step 3: Synthesis of Compound 72.

To a stirred solution of val-cit-PAB-MMAE (30 mg) in anhydrous DMF (500 µL) was added compound 73 (11 mg) and stirred for 5 min at 0° C. HATU (9.95 mg) and NMM (4.26 µL) were added in succession and the reaction mixture was allowed to stir at 0° C. After 0.5 h, and 2 h an additional amount of HATU and NMM was added and after a further 2.0 h the reaction solution was then concentrated in vacuo and then purified by reverse phase C18-column chromatography eluting with buffer A (v/v): water:5% acetonitrile: 0.05% trifluoroacetic acid and buffer B (v/v): acetonitrile: 0.05% trifluoroacetic acid (100:0 v/v to 0:100 v/v). The organic solvent was removed in vacuo and the aqueous solvent was removed by lyophilisation to give the mPEG(7u)-sulfone-propanoyl-benzamide-val-cit-PAB-MMAE reagent 72 as off-white solid (15.0 mg, 46%) m/z [M+H]$^+$ (1671).

EXAMPLE 35

Synthesis of a Conjugation Reagent 75 Comprising 7 Repeat Unit Ethylene Glycol Leaving Groups and a Furan Linker

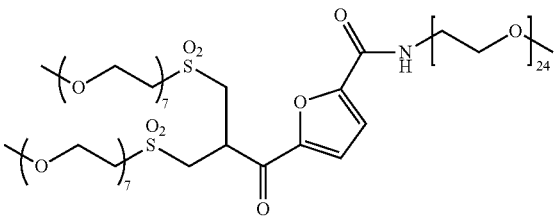

Step 1: Synthesis of Reagent 76

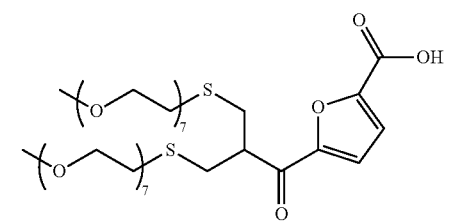

To a suspension of N,N-dimethylmethyleneiminium iodide (407 mg) in DMF (3.0 mL) was added 5-acetylfuran-2-carboxylic acid (169 mg). The reaction mixture was heated to 125° C. and stirred under an inert atmosphere for 90 min. To a portion of the reaction mixture (1.0 mL) was added mPEG-(7u)-SH (325 mg) and Et₃N (363 μL). The reaction mixture was stirred at room temperature under an inert atmosphere for 90 min. Volatiles were removed in vacuo. The resulting residue was dissolved in water (1.0 mL) and purified by reverse phase C18-column chromatography eluting with buffer A (v/v): water: 0.05% trifluoroacetic acid and buffer B (v/v): acetonitrile:0.05% trifluoroacetic acid (98:2 v/v to 0:100 v/v). The organic solvent was removed in vacuo and the aqueous solvent was removed by lyophilisation to give bis-mPEG(7u)-sulfide-propanoyl-furan-2-carboxylic acid reagent 76 as pale yellow oil (119 mg, 36%). Yield calculation based on a $\frac{1}{3}^{rd}$ portion of the initial reaction mixture used. ¹H NMR (400 MHz, DMSO) 2.60-2.70 (4H, m, $CH_2$), 2.80-2.90 (4H, m, $CH_2$), 3.24 (6H, s, OMe), 3.40-3.60 (m, PEG), 3.90-3.95 (1H, m, CH), 7.36 (1H, d, Ar—H), 7.69 (1H, d, Ar—H).

Step 2: Synthesis of Reagent 77

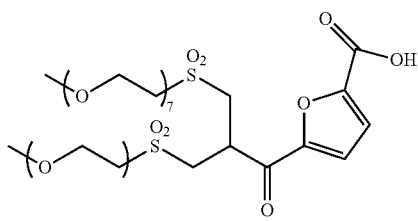

77

To a solution of 76 (30.0 mg) in methanol:water (1.0 mL, 9:1 v/v) was added Oxone® (62.1 mg, Sigma-Aldrich). The reaction mixture was stirred at room temperature under an inert atmosphere for 120 min. The crude reaction mixture was concentrated in vacuo. The resulting residue was dissolved in dichloromethane (3×5.0 mL), filtered through a column of magnesium sulfate and washed with dichloromethane (2×5.0 mL). The eluent and washings were combined and the volatiles were removed in vacuo to give bis-mPEG(7u)-sulfone-propanoyl-furan-2-carboxylic acid reagent 77 as a cicar colourless oil (31.0 mg, 97%). m/z $[M+H]^+$ 955.28 Da.

Step 3: Synthesis of Reagent 75

Stock solutions of HATU (51.5 mg) in DMF (200 μL) and NMM (15.0 μL) in DMF (200 μL) were prepared. A DMF (500 μL) solution of bis-mPEG(7u)-sulfone-propanoyl-furan-2-carboxylic acid 77 (31.0 mg) was added to a DMF (500 μL) solution of H2N-PEG(24u)-OMe (29.5 mg, Iris Biotech). The resulting reaction mixture was stirred at room temperature under an inert nitrogen atmosphere. Aliquots of HATU (40 μL) and NMM (40 μL) were added at time 0 min, 10 min, 30 min and an aliquot of HATU (80 μL) and NMM (80 μL) was added at 90 min. After 120 min, volatiles were removed in vacuo. The resulting residue was dissolved in water:acetonitrile (1.0 mL, 1:1 v/v) and purified by reverse phase C18-column chromatography eluting with buffer A (v/v): water: 0.05% trifluoroacetic acid and buffer B (v/v): acetonitrile:0.05% trifluoroacetic acid (98:2 v/v to 0:100 v/v). The organic solvent was removed in vacuo and the aqueous solvent was removed by lyophilisation to give bis-mPEG(7u)-sulfone-propanoyl-furan-2 amide-PEG (24u)-OMe reagent 75 as clear colourless oil (9.6 mg, 18%). m/z $[M+2H]^{2+}$ 1012.76 Da.

EXAMPLE 36

Synthesis of a Conjugation Reagent 78 Comprising 7 Repeat Unit Ethylene Glycol Sulfide Leaving Groups

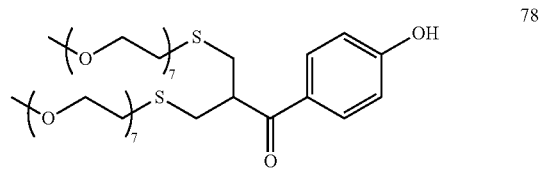

78

To a solution of 1-(4-hydroxyphenyl)-3-tosyl-2-(tosylmethyl)propan-1-one (400 mg) in DMF (8.0 mL) was added Et₃N (708 μL, Acros Organics) and MeO-PEG-(7u)-SH (905 mg, Iris Biotech). The reaction was stirred under an inert nitrogen atmosphere at room temperature. After 48 h, volatiles were removed in vacuo. The resulting residue was dissolved in water: acetonitrile (2.0 mL, 1:1 v/v) and purified by reverse phase C18-column chromatography eluting with buffer A (v/v): water: 0.05% trifluoroacetic acid and buffer B (v/v): acetonitrile:0.05% trifluoroacetic acid (98:2 v/v to 0:100 v/v). The organic solvent was removed in vacuo and the aqueous solvent was removed by lyophilisation to give compound 79 as clear colourless oil (322 mg, 43%) m/z $[M+H]^+$ 873.49 Da.

EXAMPLE 37

Synthesis of a Conjugation Reagent 79 Comprising 7 Repeat Unit Ethylene Glycol Sulfone Leaving Groups

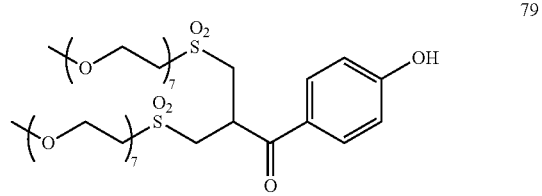

79

To a stirred solution of compound 78 (20.0 mg) in methanol:water (500 μL, 9:1 v/v) at room temperature was added Oxone® (42.2 mg. Sigma-Aldrich). After 3 h, the volatiles were removed in vacuo. The resulting residue was dissolved in water:acetonitrile (800 μL, 1:1 v/v) and purified by reverse phase C18-column chromatography eluting with buffer A (v/v): water: 0.05% trifluoroacetic acid and buffer B (v/v): acetonitrile:0.05% trifluoroacetic acid (98:2 v/v to 0:100 v/v). The organic solvent was removed in vacuo and the aqueous solvent was removed by lyophilisation to give compound 79 as clear colourless oil (19.5 mg, 91%) m/z $[M+H]^+$ 936.86 Da.

EXAMPLE 38

Synthesis of a Conjugation Reagent 80 Comprising 7 Repeat Unit Ethylene Glycol Sulfone Leaving Groups and a Phenol Ester Linker

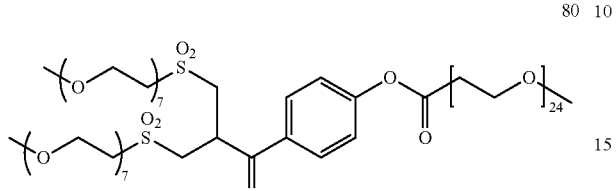

phase C18-column chromatography eluting with buffer A (v/v): water: 0.05% trifluoroacetic acid and buffer B (v/v): acetonitrile:0.05% trifluoroacetic acid (98:2 v/v to 0:100 v/v). The organic solvent was removed in vacuo and the aqueous solvent was removed by lyophilisation to give compound 80 as clear colourless oil (12.7 mg, 88%) m/z $[M+3H]^{3+}$ 679.16 Da.

EXAMPLE 39

Synthesis of a Conjugation Reagent 82 Comprising 7 Repeat Unit Ethylene Glycol Sulfone Leaving Groups, Non-Aromatic Linker and an Auristatin Cytotoxic Payload

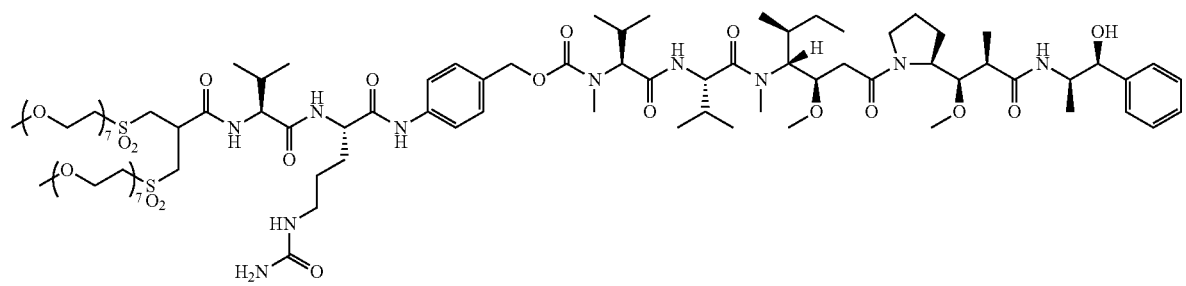

Step 1: Synthesis of Compound 81:

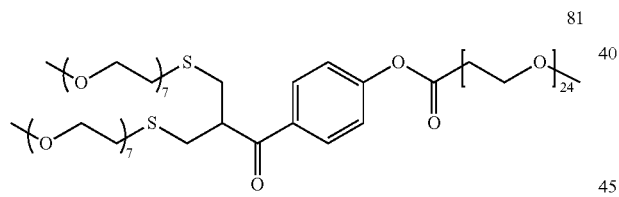

To a solution of mPEG(24u)-COOH (38.4 mg, Iris Biotech) in DMF (400 µL) was added HATU (26.1 mg) and DIPEA (12.0 µL). The reaction was stirred under an inert nitrogen atmosphere at room temperature for 5.0 min. To this mixture was added compound 79 (20.0 mg) dissolved in DMF (100 µL). The reaction was stirred under an inert nitrogen atmosphere at room temperature for a further 42 h. After 42 h, volatiles were removed in vacuo. The resulting residue was dissolved in water (800 µL) and purified by reverse phase C18-column chromatography eluting with buffer A (v/v): water: 0.05% trifluoroacetic acid and buffer B (v/v): acetonitrile:0.05% trifluoroacetic acid (98:2 v/v to 0:100 v/v). The organic solvent was removed in vacuo and the aqueous solvent was removed by lyophilisation to give compound 81 as clear colourless oil (15.4 mg, 34%) m/z $[M+2H-mPEG(7u) \text{ fragment}]^{2+}$ 824.34 Da.

Step 2: Synthesis of Compound 80:

To a stirred solution of compound 81 (14.0 mg) in methanol:water (500 µL, 9:1 v/v) at room temperature was added Oxone® (13.1 mg, Sigma-Aldrich). After 230 min, the volatiles were removed in vacuo. The resulting residue was dissolved in water (1.0 mL) and purified by reverse Step 1: Synthesis of Compound 83:

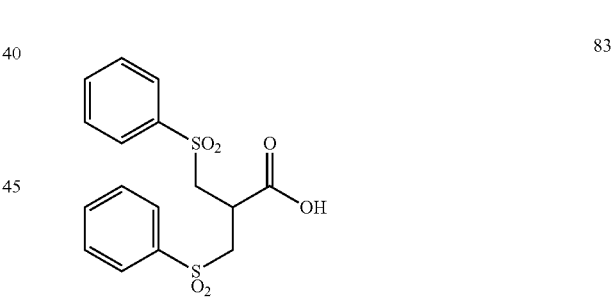

To a stirred solution of 3-bromo-2-(bromomethyl) propionic acid (1.32 g, Alfa Aesar) in methanol (50.0 mL) at room temperature was added crushed sodium hydroxide pellets (428 mg, Fisher Scientific). The mixture was heated until the solids dissolved. The sodium salt of benzenesulfinic acid (1.76 g, Sigma Aldrich) was added and the reaction mixture was refluxed under an inert nitrogen atmosphere. After 4.0 h, the reaction mixture was cooled to room temperature and was stirred overnight under an inert nitrogen atmosphere. After 20 h, the volatiles were removed in vacuo. The resulting residue was dissolved in 0.5 M sodium hydroxide (30 mL) and was washed with diethyl ether (3×10.0 mL). The aqueous fraction was made acidic with 37% hydrochloric acid and gave a white precipitate. The precipitate was collected by Buchner filtration, the retentate was washed with distilled water (3×20.0 mL) and aqueous solvent was removed by lyophilisation to give compound 83 as a white powder (632 mg, 32%) m/z [M+H]$^+$ 369.08 Da; [M+Na]$^+$ 391.04 Da.

Step 2: Synthesis of Compound 84:

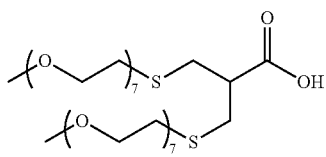

84

To a stirred solution of compound 83 (111 mg) in dimethylformamide (2.0 mL) at room temperature was added alpha-methoxy-omega-mercapto hepta(ethylene glycol) (428 mg, Iris Biotech) and triethylamine (251 μL). The resulting reaction mixture was stirred under an inert nitrogen atmosphere at room temperature. After 20 h, the crude reaction mixture was diluted with water (1.0 mL) and purified by reverse phase C18-column chromatography eluting with buffer A (v/v): water: 0.05% trifluoroacetic acid and buffer B (v/v): acetonitrile:0.05% trifluoroacetic acid (98:2 v/v to 0:100 v/v). The organic solvent was removed in vacuo and the aqueous solvent was removed by lyophilisation to give compound 84 as clear colourless oil (154 mg, 64%) m/z [M-PEG-(7u)]$^+$ 473.05 Da.

Step 3: Synthesis of Compound 85:

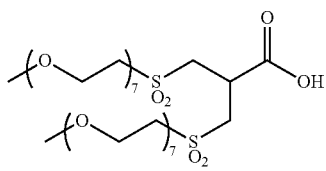

85

To a stirred solution of bis-mPEG(7u)-sulfide-propanoic acid (65.0 mg) in methanol:water (1.5 mL, 9:1 v/v) at room temperature was added Oxone® (151 mg, Sigma-Aldrich). After 3.0 h, the volatiles were removed in vacuo. The resulting residue was dissolved in water (800 μL) and purified by reverse phase C18-column chromatography eluting with buffer A (v/v): water: 0.05% trifluoroacetic acid and buffer B (v/v): acetonitrile:0.05% trifluoroacetic acid (98:2 v/v to 0:100 v/v). The organic solvent was removed in vacuo and the aqueous solvent was removed by lyophilisation to give compound 85 as clear colourless oil (41.7 mg, 59%) m/z [M+H]$^+$ 860.91 Da.

Step 4: Synthesis of Compound 82:

Stock solutions of HATU (26.4 mg) in DMF (200 μL) and NMM (7.6 μL) in DMF (200 μL) were prepared. A DMF (200 μL) solution of compound 83 (12.0 mg) was added to a DMF (400 μL) solution of NH2-Val-Cit-PAB-MMAE (21.5 mg, Concortis). The resulting reaction mixture was stirred at room temperature under an inert nitrogen atmosphere. Aliquots of HATU (80 μL) and NMM (80 μL) were added at time 0 min and 40 min for a total of 2 additions. After 180 min, volatiles were removed in vacuo. The resulting residue was dissolved in water:acetonitrile (1.0 mL, 1:1 v/v) and purified by reverse phase C18-column chromatography eluting with buffer A (v/v): water: 0.05% trifluoroacetic acid and buffer B (v/v): acetonitrile:0.05% trifluoroacetic acid (98:2 v/v to 0:100 v/v). The organic solvent was removed in vacuo and the aqueous solvent was removed by lyophilisation to give reagent 82 as a white powder (13.6 mg, 50%). m/z [M+2H]$^{2+}$ 983.45 Da.

EXAMPLE 40

Synthesis of a Conjugation Reagent 86 Comprising 7 Repeat Unit Ethylene Glycol Sulfone Leaving Groups and Non-Aromatic Linker

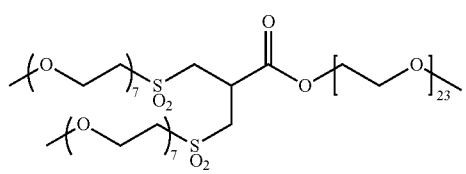

86

Step 1: Synthesis of Compound 87.

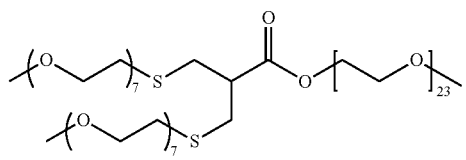

87

To a stirred solution of compound 84 (15.0 mg) in toluene (250 μL) at room temperature was added mPEG-(23u)-OH (19.7 mg, Iris Biotech), triphenylphosphine (5.43 mg, Sigma Aldrich) and diisopropyl azodicarboxylate (4.1 μL, Sigma Aldrich). The resulting reaction mixture was stirred under an inert nitrogen atmosphere at room temperature. After 30 min, additional triphenylphosphine (5.43 mg, Sigma Aldrich) and diisopropyl azodicarboxylate (4.10 Sigma Aldrich) were added. The reaction mixture was stirred under an inert nitrogen atmosphere at room temperature. After 1.0 h, the volatiles were removed in vacuo. The resulting residue was dissolved in water (700 μL) and purified by reverse phase C18-column chromatography eluting with buffer A (v/v): water: 0.05% trifluoroacetic acid and buffer B (v/v): acetonitrile:0.05% trifluoroacetic acid (98:2 v/v to 0:100 v/v). The organic solvent was removed in vacuo and the aqueous solvent was removed by lyophilisation to give compound 87 as clear colourless wax (18.5 mg, 54%) m/z [M-PEG-(7u)]$^+$ 750.19 Da.

Step 2: Synthesis of Compound 86.

To a stirred solution of compound 87 (14.5 mg) in methanol:water (1.0 mL, 9:1 v/v) at room temperature was added Oxone® (14.7 mg, Sigma-Aldrich). After 3.0 h, the reaction mixture was filtered through cotton wool (1.5 cm plug). The crude product was purified by reverse phase C18-column chromatography eluting with buffer A (v/v): water: 0.05% trifluoroacetic acid and buffer B (v/v): acetonitrile:0.05% trifluoroacetic acid (98:2 v/v to 0:100 v/v). The organic solvent was removed in vacuo and the aqueous solvent was removed by lyophilisation to give compound 86 as clear colourless wax (7.1 mg, 47%) m/z [M+3H]$^{3+}$ 629.91 Da.

EXAMPLE 41

Synthesis of a Bifunctional Conjugation Reagent 88 Comprising 7 Repeat Unit Ethylene Glycol Sulfone Leaving Groups and Poly Ethylene Glycol Spacer

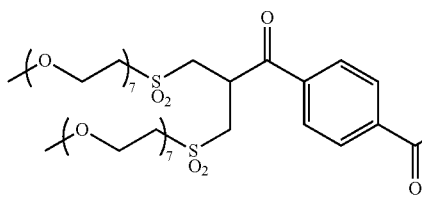
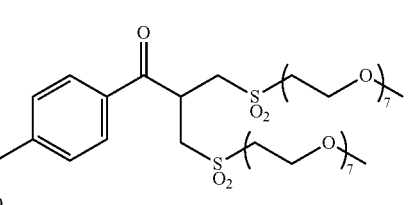

88

Stock solutions of HATU (448 mg) in DMF (2.0 mL) and NMM (129 µL) in DMF (2.0 mL) were prepared. A DMF (500 µL) solution of amino-PEG-(11u)-amine (64.1 mg, Iris Biotech) was added to a DMF (2.0 mL) solution of 4-[2,2-bis[alpha-methoxy-omega-sulfonyl hepta(ethylene glycol)] acetyl]benzoic acid (250 mg). The resulting reaction mixture was stirred at room temperature under an inert nitrogen atmosphere. Aliquots of HATU (800 µL) and NMM (800 µL) were added at time 0 min and aliquots of HATU (200 µL) and NMM (200 µL) were added at time 50 min for a total of 2 additions. After 2.0 h, volatiles were removed in vacuo. The resulting residue was dissolved in water (1.0 mL) and purified by reverse phase C18-column chromatography eluting with buffer A (v/v): water: 0.05% trifluoroacetic acid and buffer B (v/v): acetonitrile:0.05% trifluoroacetic acid (98:2 v/v to 0:100 v/v). The organic solvent was removed in vacuo and the aqueous solvent was removed by lyophilisation to give reagent 88 as a clear colourless oil (200 mg, 69%). m/z $[M+H]^{2+}$ 1219.5 Da $[M+2H]^{3+}$ 813.35 Da, $[M+3H]^{4+}$ 610.28 Da.

EXAMPLE 42

Synthesis of a Conjugation Reagent 89 Comprising 7 Repeat Unit Ethylene Glycol Sulfone Leaving Groups and a Sulfonic Acid Side Chain

89

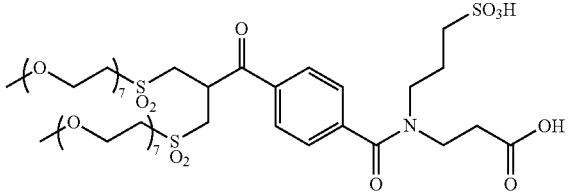

To a stirred solution of 3-(N-(3-sulfopropyl)-4-(3-tosyl-2-(tosylmethyl)propanoyl)benzamido) propanoic acid (Click Chemistry Tools LLC, 20.0 mg) in dimethylformamide (500 µL) at room temperature was added alpha-methoxy-omega-mercapto hepta(ethylene glycol) (30.2 mg, Iris Biotech) and triethylamine (23.6 µL). The resulting reaction mixture was stirred under an inert nitrogen atmosphere at room temperature. After 3.5 h, the crude intermediate product was purified by reverse phase C18-column chromatography eluting with buffer A (v/v): water: 0.05% trifluoroacetic acid and buffer B (v/v): acetonitrile:0.05% trifluoroacetic acid (98:2 v/v to 0:100 v/v). The organic solvent was removed in vacuo and the aqueous solvent was removed by lyophilisation. The resulting clear colourless residue was dissolved in methanol:water (750 µL, 9:1 v/v) and the solution was added to Oxone® (52.1 mg, Sigma-Aldrich). The resulting reaction mixture was stirred under an inert nitrogen atmosphere at room temperature. After 4.5 h the crude product was purified by reverse phase C18-column chromatography eluting with buffer A (v/v): water: 0.05% trifluoroacetic acid and buffer B (v/v): acetonitrile:0.05% trifluoroacetic acid (98:2 v/v to 0:100 v/v). The organic solvent was removed in vacuo and the aqueous solvent was removed by lyophilisation to give compound 89 as a clear colourless oil (4.71 mg, 14%) m/z $[M+H]^{2+}$ 579.67 Da, $[M+H_2O]^{2+}$ 588.17 Da.

EXAMPLE 43

PEGylation at a Reduced Fab Disulfide Bond Using Conjugation Reagents 63, 68 and 70

To the Fab of trastuzumab produced by papain digestion was added 1 M DTT stock solution (25 µL, final concentration 10 mM), the reduction mixture was briefly mixed using a vortex and incubated at 22° C. for 1 h. The reductant was then removed using a PD10 column (GE Healthcare) equilibrated with 20 mM sodium phosphate buffer pH 7.5, 150 mM NaCl, 20 mM EDTA. The reduced Fab was further diluted to 1.2 mg/mL with the same buffer. Reagents 63, 68 and 70 were dissolved independently in acetonitrile at 0.719 mM and added to separate solutions of reduced Fab (1.5 eq. reagent per Fab). The PEGylation reactions were allowed to progress at 22° C., whereupon samples were taken for HIC HPLC analysis after 22 h. HIC HPLC analysis of each reaction mixture showed that the % conversion to PEGylated Fab for reagents 63, 68 and 70 were 95%, 90% and 90% respectively.

EXAMPLE 44

Conjugation of Reagent 72, to Partially Reduced Trastuzumab

Trastuzumab (3.5 mg, 5.2 mg/mL) in 20 mM sodium phosphate, pH 7.5 (20 mM EDTA; 150 mM NaCl) was warmed to 40° C. for 15 min. To the trastuzumab, was added 2.08 mM TCEP (28 µL) and the resulting mixture was incubated at 40° C. for 1 h. After 1 h, the TCEP treated trastuzumab was cooled to 22° C. A portion of the trastuzumab solution (3.2 mg, 0.64 mL, 5.0 mg/mL) was diluted with 20 mM sodium phosphate, pH 7.5 (20 mM EDTA; 150 mM NaCl) (0.12 mL). Three vials were charged with the diluted mAb solution (1 mg, 238 µL). Solutions of reagent 72, (3.2 mM) were prepared in DMF. The reagent solutions (12.5 μL, 6.0 eq. per mAb) were added to separate vials, the reactions were mixed and then incubated at 22° C. At 22 h the reaction samples were quenched with N-acetyl-L-cysteine (20 eq. over reagent) prior to HIC analysis. HIC HPLC analysis showed that the average DAR of Trastuzumab conjugated with reagent 72 was 4.5.

EXAMPLE 45

Conjugation of Reagents 82 and 86 to Trastuzumab

Both reagents 82 and 86 were conjugated to the antibody trastuzumab using identical protocols. Briefly, trastuzumab (5.2 mg/mL) in buffer (20 mM sodium phosphate buffer, 150 mM NaCl, 20 mM EDTA, pH 8.4) was reduced with TCEP (6 eq.) at 40° C. for 1 h. Conjugation of the antibody with 1.5 molar equivalents of either reagent 82 or 86 per interchain disulfide bond was then performed at 40° C. This was achieved by addition either reagent 82 or reagent 86 in acetonitrile (5% v/v acetonitrile in each reaction). The antibody solution was diluted to 4.0 mg/mL with 20 mM sodium phosphate buffer, 150 mM NaCl, 20 mM EDTA, pH

EXAMPLE 46

PEGylation at a Reduced Fab Disulfide Bond Using Conjugation Reagents 75, 79 and 80 and Reagent 89

Reagents 75, 79, 80 and 89 were conjugated to $Fab_{trast}$ in a similar manner to that described for conjugation reagents 63, 68 and 70 within example 43. Following 22 h conjugation reaction, samples were analysed by SDS-PAGE under reducing and non-reducing conditions. The % conversion of PEGylated $Fab_{trast}$ with each of the reagents was estimated from the band density measurements using an ImageQuant™ LAS 4010 system (GE Healthcare) using gels stained with InstantBlue™. For reagents 75, 79, 80 and 89, the % conversion values were 90%, 20%, 75% and 40% respectively.

EXAMPLE 47

Synthesis of Conjugation Reagents 90 (Comparative) and 91 (Comparative) Comprising Either 3 or 5 Repeat Unit Polymeric Ethylene Glycol Leaving Groups Respectively and an Auristatin Cytotoxic Payload

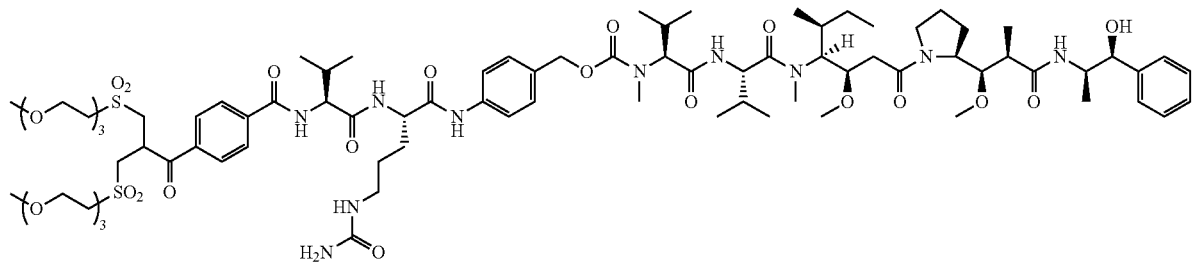

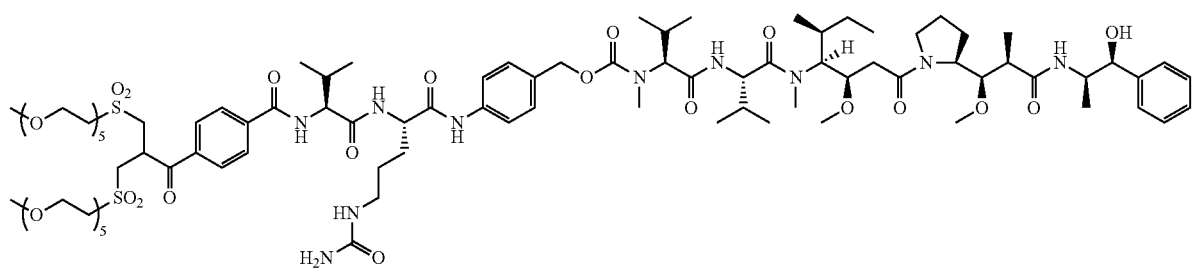

8.4. Each solution was the mixed gently and incubated at 40° C. for 22 h. At 22 h the reactions were treated with N-acetyl-L-cysteine (20 eq. over reagent) for 1 h at 22° C. The reactions were subsequently analysed by analytical HIC. The % conversion to product utilising reagents 82 and 86 were determined based on the % area of the absorbance peaks measured at 280 nm from the HIC chromatograms. For reagents 82 and 86, the % conversion to product values were 100% and 50% respectively.

Auristatin reagents bis-mPEG(3u)sulfone-propanoyl-benzamide-val-cit-PAB-MMAE 90 and bis-mPEG(5u)sulfone-propanoyl-benzamide-val-cit-PAB-MMAE 91 were synthesised in an analogous way as that described for reagent 5 in Example 4, using the thiols 2-[2-(2-methoxyethoxy)ethoxy]-ethanethiol and 2,5,8,11,14-pentaoxahexadecane-16-thiol respectively instead of alpha-methoxy-omega-mercapto hepta(ethylene glycol) for the synthesis of compound 1 in Example 1.

EXAMPLE 48

Synthesis of a PEGylation Reagent 92 Comprising a Single 7 Repeat Unit Ethylene Glycol Leaving Group and a 24 Unit PEG

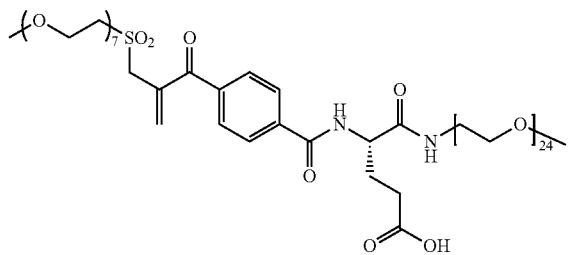

92

The synthesis of mono-mPEG(7u)sulfone-(methyl-acryloyl)-benzamide-L-Glu-[OH]-[PEG(24u)-OMe] reagent 92 was carried out according to Nature Protocols (2006, 1, 2241-2252) using compound 23 in Example 10.

EXAMPLE 49

Figure 10:
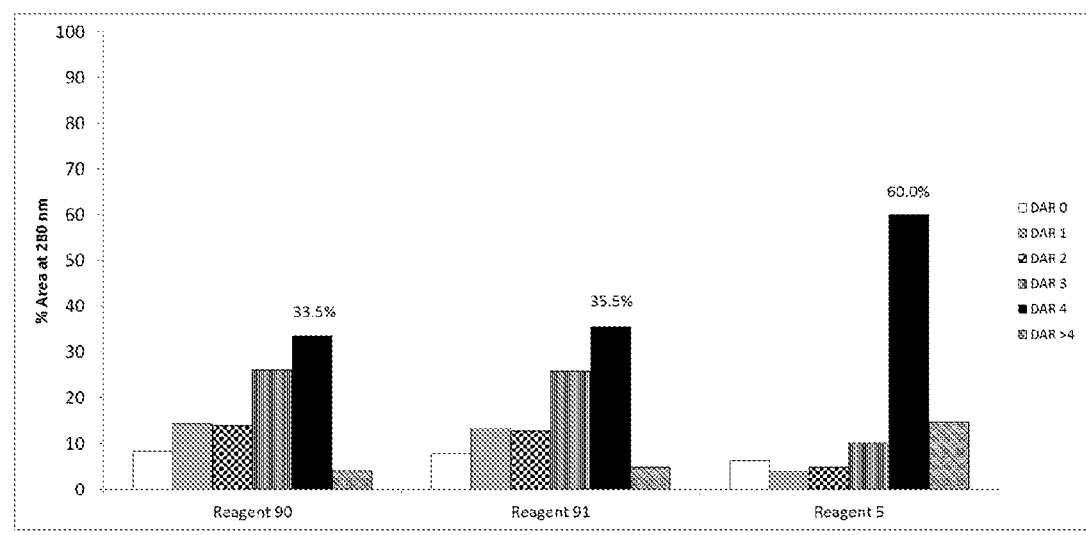
FIG. 10 shows the results of Example 49 obtained after 2 hours reaction time.
Figure 11:
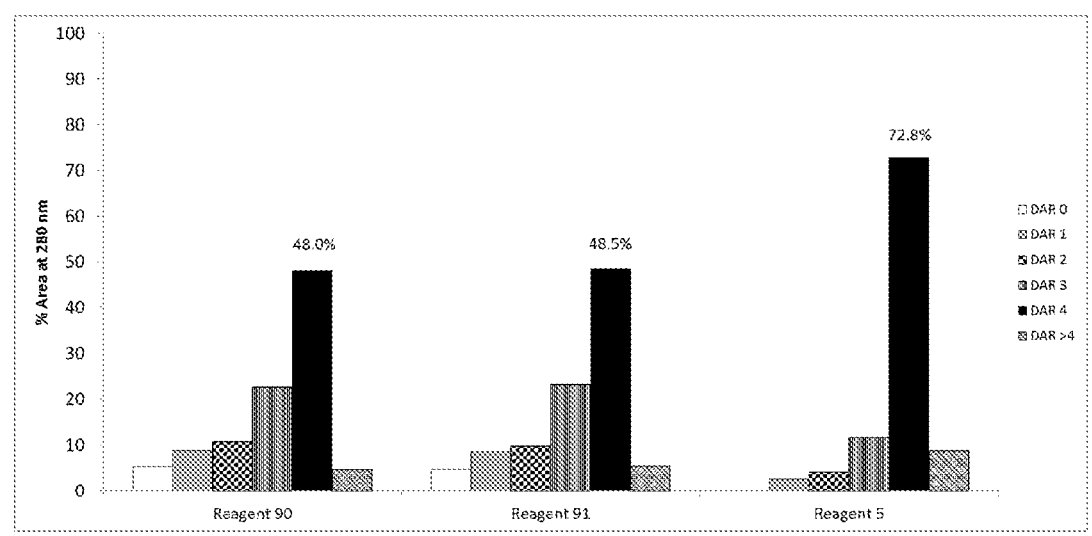
FIG. 11 shows the results of Example 49 obtained after 4 hours reaction time.

Comparison of the Antibody Conjugation of Cytotoxic Reagents 90 (Comparative), 91 (Comparative) and 5 Possessing Polymeric Ethylene Glycol Leaving Groups The reaction conditions used for conjugation of cytotoxic reagents 90, 91 and 5 with trastuzumab (1 mg scale) were the same as those described above for Example 20, using 1.25% v/v MeCN as solvent in the conjugation reaction in place of DMF. Aliquots of reaction solution were taken after 2 and 4 h and each were quenched by treatment with N-acetyl-L-cysteine. Each aliquot was analysed by HIC and the % DAR product profile determined. Results for conjugation with reagents 90, 91 and 5 are displayed in Table 3 and FIGS. 10 (2 hours) and 11 (4 hours). It can be seen that the results obtained when using the reagent according to the present invention are significantly improved compared to the results obtained using the comparison reagents, in that the homogeneity of the product is much higher, the product being predominantly the desired DAR4 conjugate.

TABLE 3

Comparison of conjugation of reagents 90, 91 and 5 to an antibody after 2 h and 4 h reaction.

| Reagent used for conjugation to an antibody | % DAR product after 2 h | | | | | | % DAR product after 4 h | | | | | |
|---|---|---|---|---|---|---|---|---|---|---|---|---|
| | 0 | 1 | 2 | 3 | 4 | >4 | 0 | 1 | 2 | 3 | 4 | >4 |
| 90 | 8.3 | 14.4 | 13.9 | 26.0 | 33.5 | 4.0 | 5.2 | 8.9 | 10.8 | 22.6 | 48.0 | 4.6 |
| 91 | 7.9 | 13.3 | 12.7 | 25.8 | 35.5 | 4.8 | 4.7 | 8.6 | 9.7 | 23.2 | 48.5 | 5.4 |
| 5 | 6.3 | 4.0 | 4.8 | 10.2 | 60.0 | 14.7 | 0.0 | 2.6 | 4.2 | 11.6 | 72.8 | 8.8 |

EXAMPLE 50

Pegylation at a Reduced Fab Disulfide Bond Using Reagent 92

Reagent 92 was conjugated to a reduced Fab using the same conditions as those described in Example 17. The reactions were subsequently analysed by SDS-PAGE and the major product, PEGylated Fab, was observed at 49 kDa against the molecular weight protein standards.

EXAMPLE 51

Synthesis of Conjugation Reagent 93 Comprising an Auristatin Cytotoxic Payload

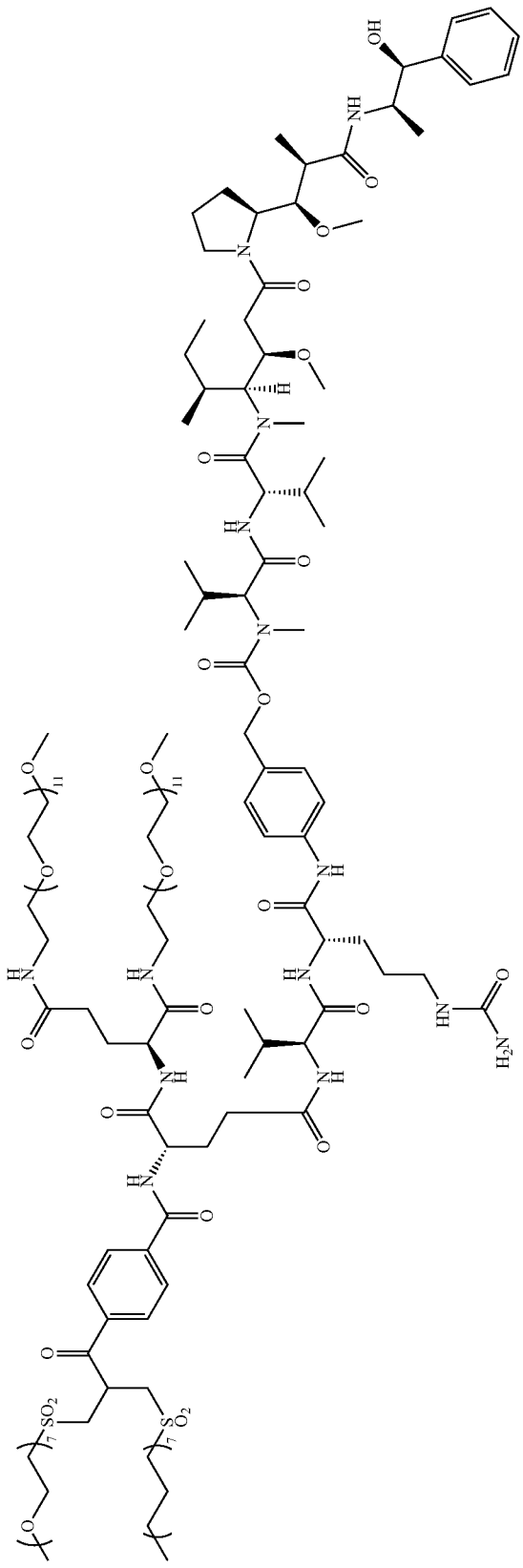

Step 1: Synthesis of Compound 94.

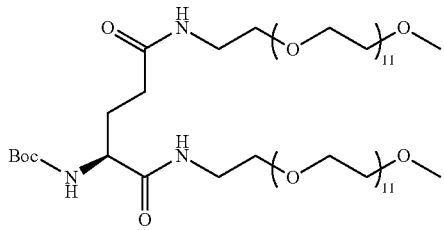

94

Boc-L-Glu (135 mg) and (benzotriazol-1-yloxy)tris-(dimethylamino) phosphonium hexafluorophosphate (BOP) (724 mg) were dissolved in anhydrous DMF (4 mL) and were stirred at 0° C. under a nitrogen atmosphere for 1.25 h. This solution was then added to a solution of $H_2N$-PEG (12u)-Me (685 mg) and NMM (180 µL) in DMF (3 mL). The solution was then stirred under $N_2$ for 4 h. The solution was then stirred 0-4° C. under a nitrogen atmosphere for 4.5 h. Further BOP (241 mg) and NMM (60 µL) were added, reaction mixture left for 24 h at 4° C. The volatiles were removed in vacuo and the resulting residue was purified by reverse phase C18-flash chromatography eluting with eluting with buffer A (v/v): water:5% acetonitrile:0.1% formic acid and buffer B (v/v): acetonitrile:0.1% formic acid (100:0 v/v to 65:35 v/v). The organic solvent was removed in vacuo and the aqueous solvent was removed by lyophilisation. The material was repurified by normal phase flash chromatography eluting with ethyl acetate:methanol (100:0 v/v to 0:100 v/v). The organic solvent was removed in vacuo and the aqueous solvent was removed by lyophilisation to give Boc-Glu-[PEG(12u)-Me]$_2$ compound 94 as a colourless oil (450 mg). m/z $[M+H]^+$ (1331, 100%), $[M+2H]^{2+}$ (665, 100%).

Step 2: Synthesis of Compound 95.

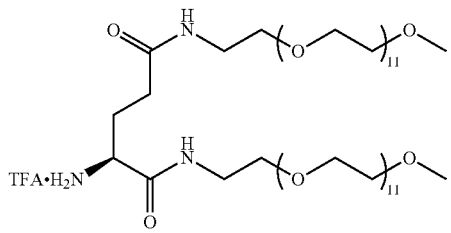

95

Compound 94 (450 mg) was dissolved in DCM (25 mL) to which was added TFA (2.5 mL). The solution stirred at room temperature for 5 h. After which the volatiles were removed in vacuo. The resulting residue was purified by reverse phase C18-flash chromatography eluting with buffer A (v/v): water:5% acetonitrile:0.05% trifluoroacetic acid and buffer B (v/v): acetonitrile:0.05% trifluoroacetic acid (100:0 v/v to 60:40 v/v). The organic solvent was removed in vacuo and the aqueous solvent was removed by lyophilisation to give Glu-[HN-PEG(12u)-Me]$_2$ TFA compound 95 as a clear colourless gum (320 mg) m/z $[M+Na]^{1+}$ (1253.0, 10%) $[M+H]^{2+}$ (616.8, 100%).

Step 3: Synthesis of Compound 96

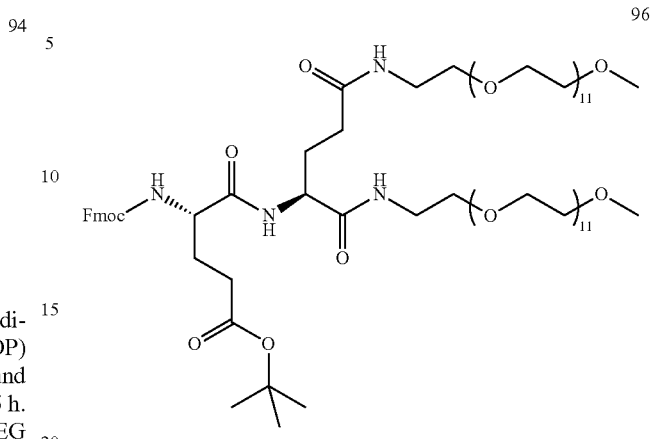

96

To a stirred solution of Fmoc-L-Glu-(OtBu)-OH (36 mg) in anhydrous DMF (2 mL) was added HATU (37 mg). The reaction mixture was stirred at 0° C. under a nitrogen atmosphere for 1 h and then added to a solution of compound 95 (103.5 mg) and NMM (19 µL) in DMF (1 mL). Additional DMF (1 mL) was added. The stirred reaction was left to warm to room temperature over 5 h. The volatiles were removed in vacuo. The resulting pale yellow oil was purified by reverse phase C18-flash chromatography eluting with buffer A (v/v): water:5% acetonitrile:0.1% formic acid and buffer B (v/v): acetonitrile:0.1% formic acid (100:0 v/v to 50:50 v/v). The organic solvent was removed in vacuo and the aqueous solvent was removed by lyophilisation to give Fmoc-L-Glu-(O$^t$Bu)-Glu-[HN-PEG(12u)-Me]$_2$ compound 96 (173 mg) as a white paste. m/z $[M+1]^+$ (1638, 100%) & $[M+Na]^+$ (1660, 57%).

Step 4: Synthesis of Compound 97

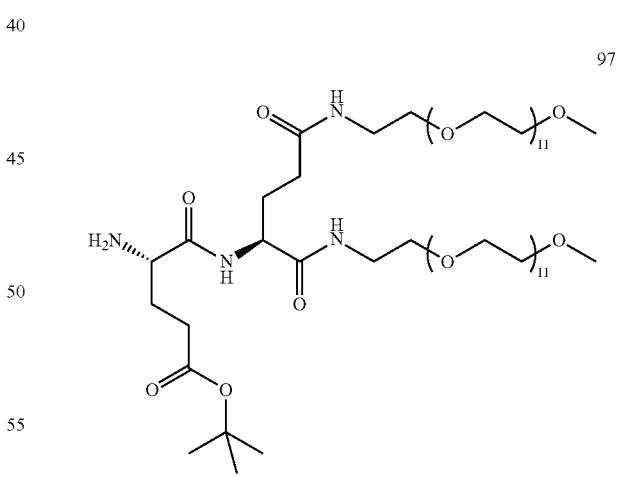

97

To a stirred solution of compound 96 (173 mg) in anhydrous DMF (3.2 mL) was added piperidine (104 µL). The solution was stirred at room temperature under argon for 1.5 h. The volatiles were removed in vacuo and the residue triturated repeatedly with hexane. The product was dried in vacuo to give L-Glu-(O$^t$Bu)-L-Glu-[HN-PEG(12u)-Me]$_2$ compound 97 (152 mg) as a clear colourless oil. m/z $[M+H]^{1+}$ (1416.7, 85%), $[M+2H]^{2+}$ (708.5, 100%), $[M+Na]^{1+}$ (1438.7, 30%).

Step 5: Synthesis of Compound 98

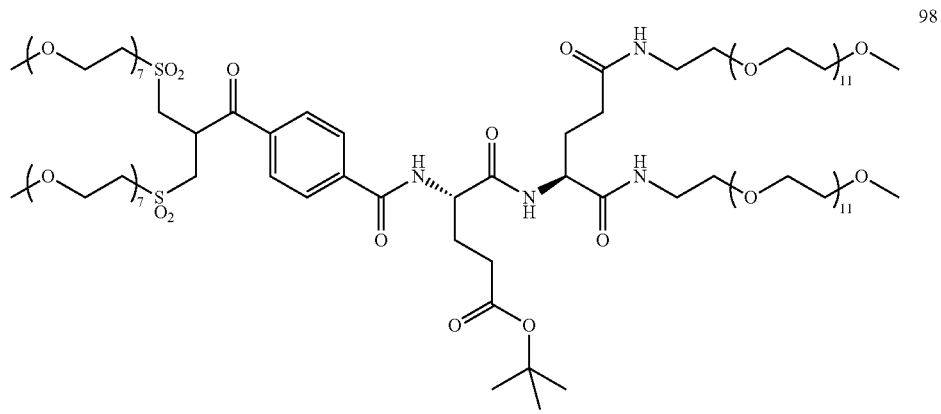

To a stirred solution of 4-[2,2-bis[alpha-methoxy-omega-sulfonyl hepta(ethylene glycol)]acetyl]benzoic acid (114 mg) in anhydrous DMF (3 mL) was added HATU (51 mg). Reaction mixture was stirred at 0° C. for 0.5 h then added to a solution of L-Glu(OtBu)-Glu-[HN-PEG(12u)-OMe]$_2$. (152 mg) in DMF (2 mL) and washed in with further DMF (1 mL), followed by NMM (15 µL). The reaction mixture was stirred at 0-15° C. for 3.5 h after which the volatiles were removed in vacuo. The resulting residue was purified by reverse phase C18-flash chromatography eluting with buffer A (v/v): water:5% acetonitrile:0.1% formic acid and buffer B (v/v): acetonitrile:0.1% formic acid (100:0 v/v to 55:45 v/v). The organic solvent was removed in vacuo and the aqueous solvent was removed by lyophilisation to give Bis-mPEG(7u)sulfone-propanoyl-benzamide -L-Glu-(O$^t$Bu)-Glu-[HN-PEG(12u)-Me]$_2$ compound 98 (161 mg) as a clear colourless oil. m/z [M+H]$^{1+}$ (2366.7, 100%), [M+2H]$^{2+}$ (1184.0, 80%) [M+H$_2$O]$^{3+}$ (795.5, 100%).

Step 6: Synthesis of Compound 99

To the stirred solution of compound 98 (58 mg) in anhydrous DCM (6 mL) was added TFA (6 mL). Reaction mixture was stirred at room temperature for 2 h. after which the volatiles were removed in vacuo, dissolved in water (25 mL) and lyophilised to give Bis-mPEG(7u)sulfone-propanoyl-benzamide-L-Glu-(OH)-Glu-[HN-PEG(12u)-OMe]$_2$ compound 99 (160.6 mg) as a clear colourless oil. m/z [M+H]$^{1+}$ (2306.8, 90%), [M+2H]$^{2+}$ (1153.0, 100%).

Step 7: Synthesis of Reagent 93

Reagent 93 was synthesised in analogous way to reagent 24 of Example 11A from compound 99 and val-cit-PAB-MMAE TFA salt. Bis-mPEG(7u)sulfone-propanoyl-benzamide-L-Glu-(val-cit-PAB-MMAE)-Glu-[HN-PEG(12u)-Me]$_2$ 93 was isolated as a colourless oil (69%). m/z [M+H]$^{1+}$ (3410.4, 90%), [M+2H]$^{2+}$ (1706.2, 60%), [M+3H]$^{3+}$ (1137.2, 85%), [M+4H]$^{4+}$ (852.8, 70%).

Conjugation of Brentuximab with conjugation reagent 93 was carried out as described within Example 21 for 16 h. Results from analytical HIC show that the conversion to DAR4 product was 67%.

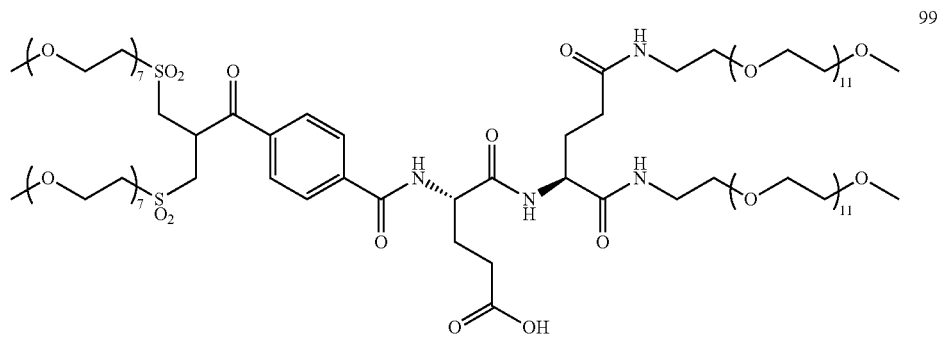

EXAMPLE 52

Synthesis of Conjugation Reagent 100 Comprising an Auristatin Cytotoxic Payload

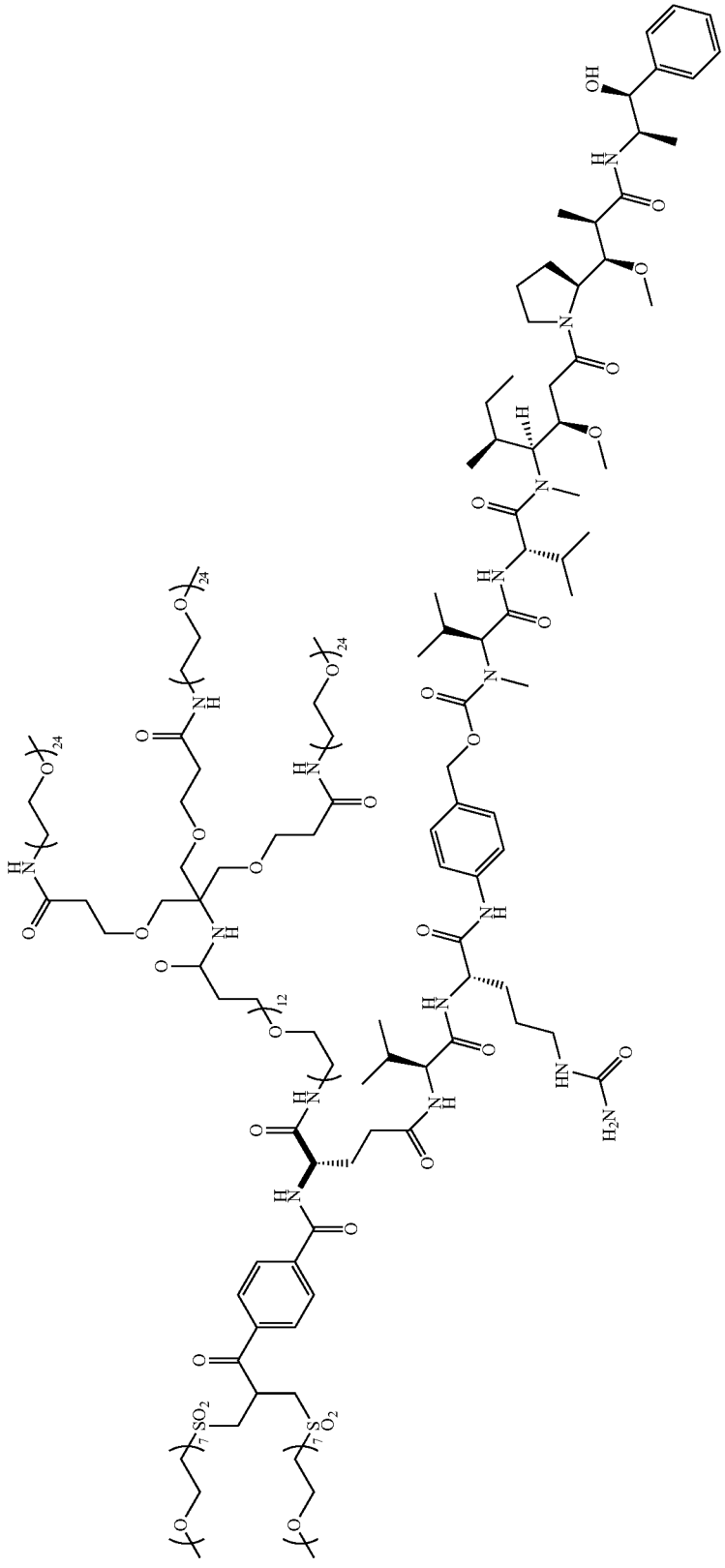

Reagent 100 was synthesised in analogous way to reagent 24 of Example 11A using compound 20B instead of compound 23 and val-cit-PAB-MMAE TFA salt instead of val-cit-AHX-DM1.

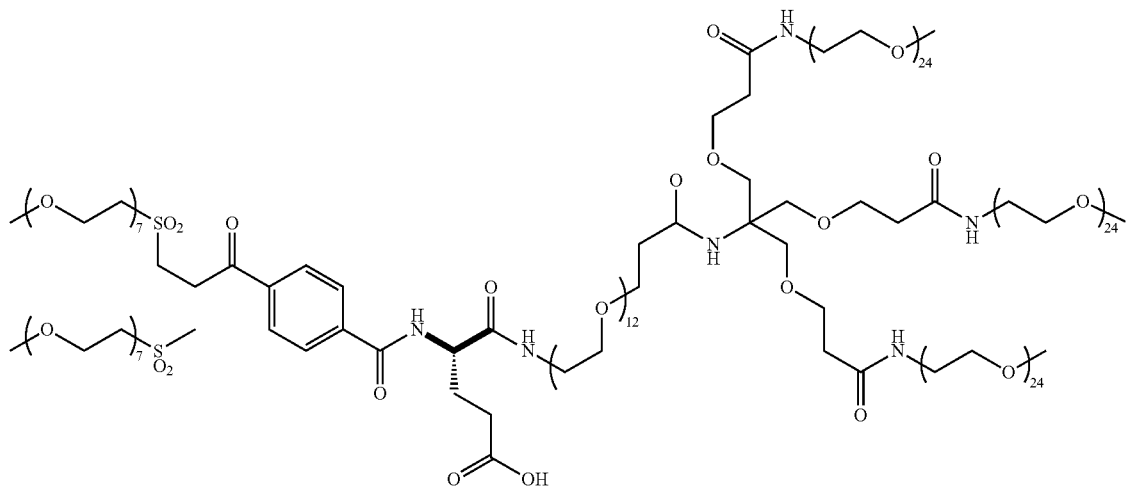

20B

Compound 20B was made in an analogous way to compound 23 in Example 10, using H$_2$N-PEG(12u)-tri(m-dPEG (24u) instead of H$_2$N-PEG(24u). Bis-mPEG(7u)sulfone-propanoyl-benzamide-L-Glu-[val-cit-PAB-MMAE]-[PEG(12u)-tri(m-dPEG(24u))] 100 was isolated as a colourless oil. m/z [M+2H]$^{2+}$ (3166, 20%), [M+3H]$^{3+}$ (2111, 50%), [M+4H]$^{4+}$ (1583, 100%).

Conjugation of Brentuximab with conjugation reagent 100 was carried out as described within Example 21 for 16 h. Results from analytical HIC show that the conversion to DAR4 product was 65%.

EXAMPLE 53

Synthesis of Conjugation Reagent 101 Comprising two Auristatin Cytotoxic Payloads

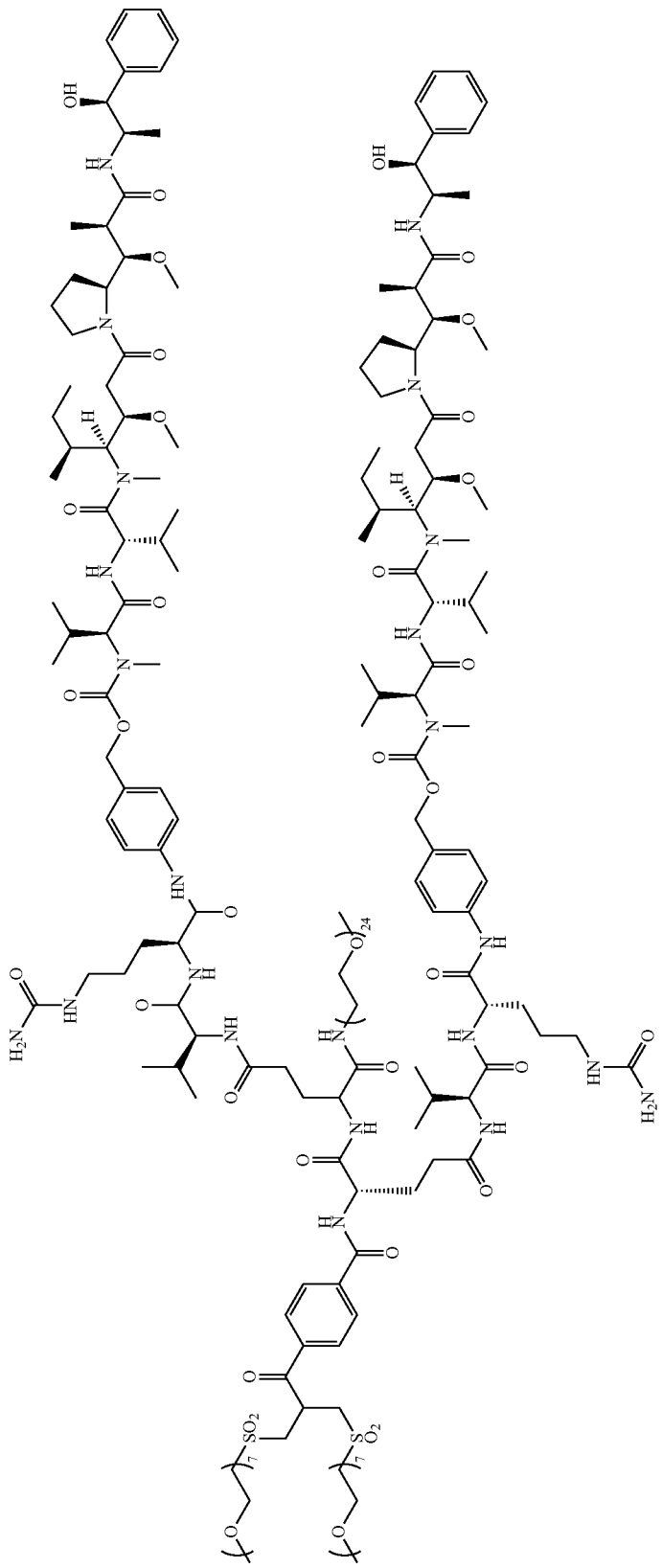

Step 1: Synthesis of Compound 102.

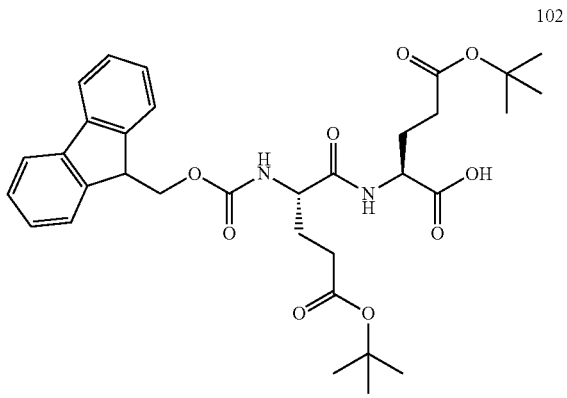 [SMILES: CC(C)(C)OC(=O)CC[C@H](NC(=O)[C@H](CCC(=O)OC(C)(C)C)NC(=O)OCC1c2ccccc2-c2ccccc21)C(=O)O]

102

To a stirred solution of Fmoc-L-Glu-(O^tBu)-OH (2 g) in anhydrous DMF (18 mL) was added HOBt (666 mg) and DIC (768 µL). The reaction mixture was stirred at 0° C. for 10 min and then 2.5 h at room temperature. H-L-Glu-(OtBu)-OH (1.19 g) and DIPEA (2.46 mL) were added and the reaction mixture was stirred for 18 h at room temperature. The reaction mixture was diluted with water (100 mL) and acidified to pH 2.0 by adding diluted HCl. The aqueous layer was extracted with EtOAc (3×100 mL), and the organic phases combined and washed with water (2×50 mL) and saturated brine solution (1×50 mL). The EtOAc layer was dried over $Na_2SO_4$ for 2 h and then concentrated on a rotary evaporator. The product was isolated by reverse phase C18-flash chromatography eluting with buffer A (v/v): water: 5% acetonitrile: 0.1% formic acid and buffer B (v/v): acetonitrile: 0.1% formic acid (100:0 v/v to 80:20 v/v). The organic solvent was removed in vacuo and the aqueous solvent was removed by lyophilisation to give compound Fmoc-L-Glu-(OtBu)-L-Glu-(OtBu)-OH 102 (875 mg) as a white solid. m/z $[M+H]^{1+}$ (610.8, 85%), $[M+Na]^{1+}$ (633.1, 55%), $[2M+Na]^+$ (1243.2, 55%).

Step 2: Synthesis of Compound 103.

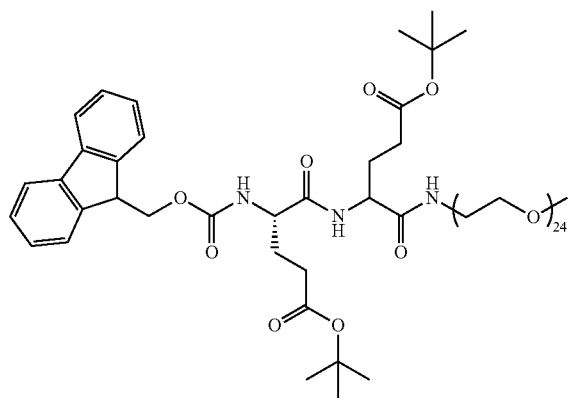

103

To a stirred solution of Fmoc-L-Glu-(OtBu)-L-Glu-(OtBu)-OH (510 mg) and $NH_2$-PEG(24u)-OMe (1 g) in anhydrous DMF (5 mL) was added and N,N-diisopropyl-ethylamine (44 µL) and HATU (48 mg). The reaction mixture was stirred at 0° C. for 10 min and then 16 h at room temperature. The solution was concentrated in vacuo to 2 mL and the residue was purified by reverse phase C18-flash chromatography eluting with buffer A (v/v): water:5% acetonitrile:0.1% formic acid and buffer B (v/v): acetonitrile:0.1% formic acid (100:0 v/v to 83:17 v/v). The organic solvent was removed in vacuo and the aqueous solvent was removed by lyophilisation to give Fmoc-Glu-(OtBu)-Glu-(OtBu)-PEG(24u)-OMe compound 103 644 mg) as a white paste. m/z $[M+H]^{1+}$ (1681.0, 40%), $[M+Na]^{1+}$ (1704.0, 30%) and $[M+2H]^{2+}$ (841.4, 55%).

Step 3: Synthesis of Compound 104.

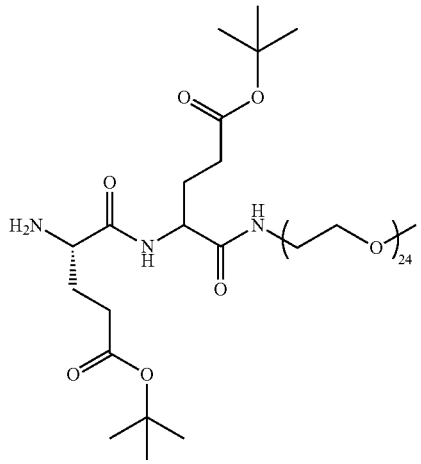

104

To a stirred solution of Fmoc-Glu-(OtBu)-Glu-(OtBu)-PEG(24u)-OMe (193 mg) in anhydrous DMF (900 µL) was added piperidine (34 µL) and the reaction mixture was stirred 1 h at room temperature. The solution was concentrated in vacuo to dryness and the residue triturated with $Et_2O$ (2×2.5 mL). The product was dried in vacuo to give H-L-Glu-(OtBu)-Glu-(OtBu)-PEG(24u)-OMe compound 104 (166 mg) as an off-white solid.

Step 4: Synthesis of Compound 105.

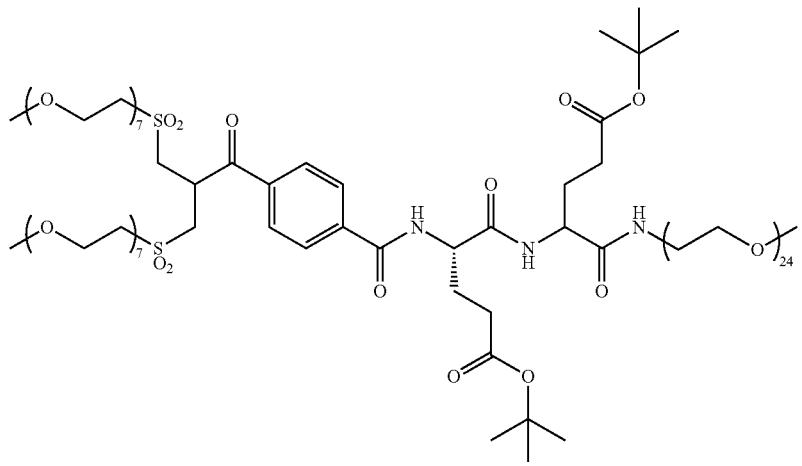

Reagent 105 was synthesised in analogous way to compound 23 of Example 10 from compound 104 and 4-[2,2-bis[alpha-methoxy-omega-sulfonyl hepta(ethylene glycol)]acetyl]benzoic acid. Bis-mPEG(7u)sulfone-propanoyl-benzamide-Glu-(OtBu)-Glu-(OtBu)-PEG(24u)-OMe 105 was isolated as a colourless oil. m/z [M+H]$^{1+}$ (2407.2, 25%), [M+Na]$^{1+}$ (2429.4, 70%).

Step 5: Synthesis of Compound 106.

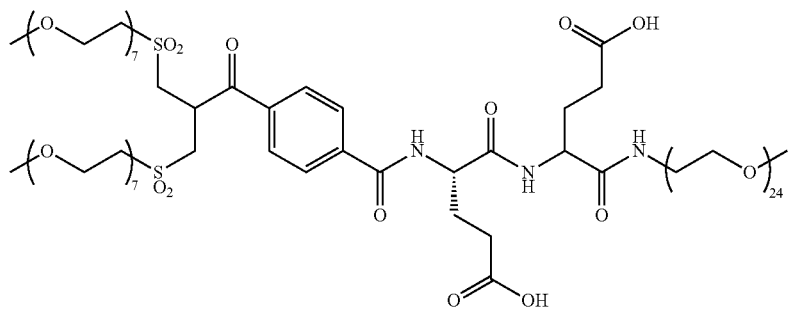

Reagent 106 was synthesised in analogous way to reagent 23 of Example 10 from compound 105. Bis-mPEG(7u) sulfone-propanoyl-benzamide-Glu-(OH)-Glu-(OH)-PEG (24u)-OMe 106 was isolated as a colourless oil. m/z [M+H]$^{1+}$ (2294.2, 20%), [M+Na]$^{1+}$ (2317.4, 10%) and [M+2Na]$^{2+}$ (1217.4, 100%).

Step 6: Synthesis of Reagent 101.

To a stirred solution of compound 106 (28 mg), val-cit-PAB-MMAE TFA salt (31 mg) and HATU (14 mg) in anhydrous DMF (1.5 mL) was added N-methylmorpholine (7 µL) and the reaction mixture was stirred at 0° C. for 5 h. The solution was diluted with water (1 mL) and purified by reverse phase C18-flash chromatography eluting with buffer A (v/v): water:5% acetonitrile:0.1% TFA and buffer B (v/v): acetonitrile:0.1% TFA (100:0 v/v to 60:40 v/v).

The organic solvent was removed in vacuo and the aqueous solvent was removed by lyophilisation to give bis-mPEG(7u)sulfone-propanoyl-benzamide-bis-[Glu-(val-cit-PAB-MMAE)]-PEG(24u)-OMe compound 101 (36 mg) as a white solid. m/z [M+2H]$^{2+}$ (2252.7, 20%), [M+3H]$^{3+}$ (1501.6.7, 40%) and [M+4H]$^{4+}$ (1126.6, 100%).

Conjugation of Brentuximab with conjugation reagent 101 was carried out as described within Example 21 for 16 h. Results from analytical HIC show that the conversion to DAR4 product was 56%.

EXAMPLE 54

Synthesis of Conjugation Reagent 107 Comprising Two Auristatin Cytotoxic Payloads

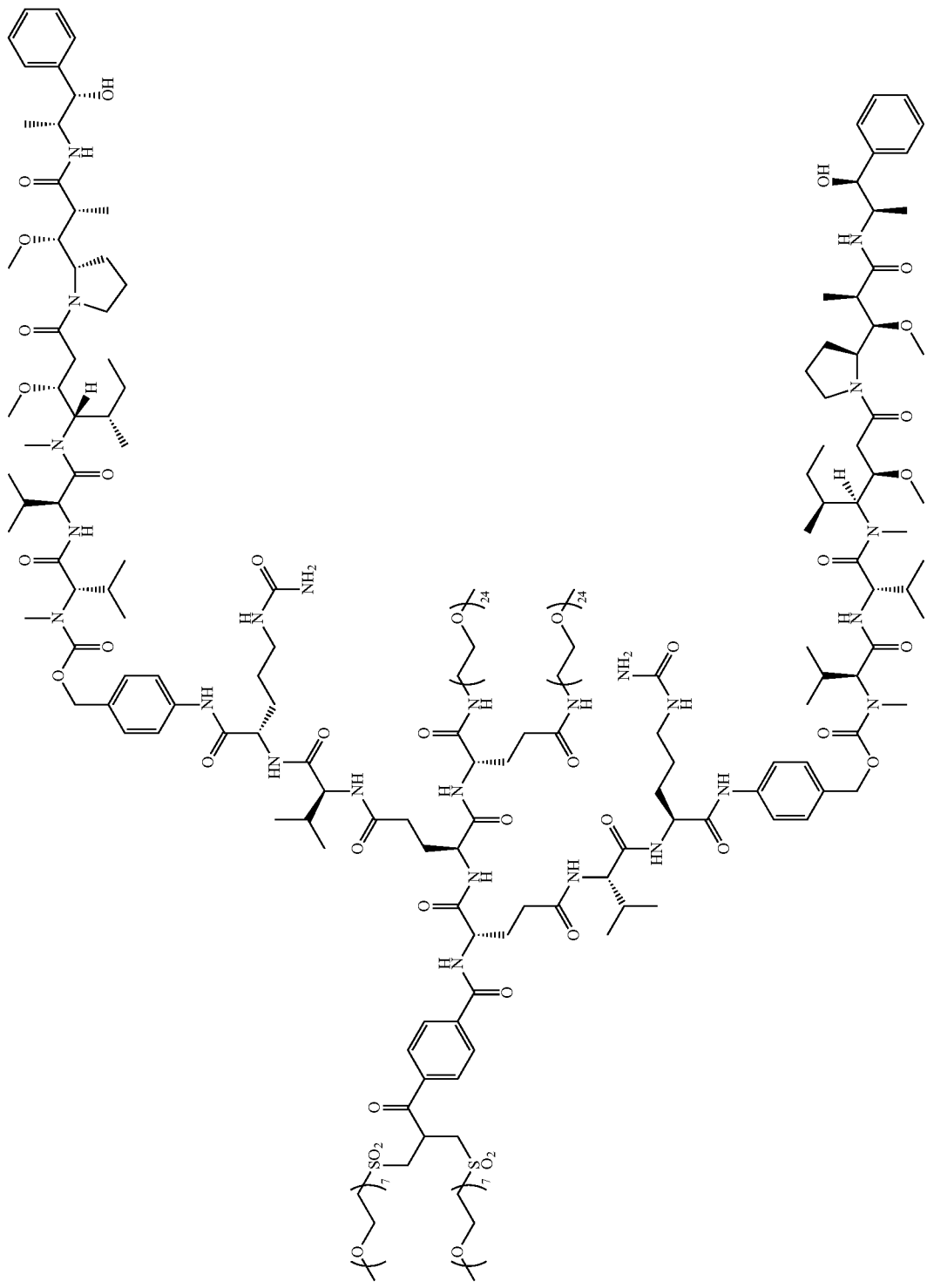

Step 1: Synthesis of Compound 108.

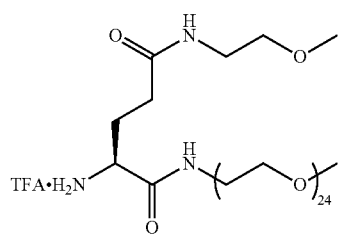

108

To a stirred solution of Boc-L-Glu(OH)—OH (51.6 mg) in anhydrous DMF (6 mL) was added BOP (277 mg). The solution was stirred at 0° C. for 20 min before MeO-PEG(24)-NH$_2$ (500 mg) was added followed by NMM (69 μL). After 4 h, additional amounts of BOP (92 mg) and NMM (23 μL) were added. After a further 2.5 h, the reaction mixture was stored at −20° C. for 18 h before being concentrated in vacuo and purified by reverse phase column C18-column chromatography, eluting with buffer A (v/v): water:0.05% trifluoroacetic acid and buffer B (v/v): acetonitrile:0.05% trifluoroacetic acid (100:0 v/v to 0:100 v/v). The organic solvent was removed in vacuo and the aqueous solvent removed by lyophilisation to give a white solid (373 mg). Formic acid (6 mL) was added to the solid and the resulting mixture stirred under an inert atmosphere for 60 min before being concentrated in vacuo. The residue was dissolved in 95% water:5% acetonitrile:0.05% trifluoroacetic acid (~6 mL) and lyophilisation overnight to give TFA.H$_2$N-Glu(PEG(24)-OMe)-PEG(24)-OMe, compound 108 as an off-white solid (330 mg). m/z [M+2H]$^{2+}$ (1144, 5%), [M+3H]$^{3+}$ (763, 35%), [M+4H]$^+$ (573, 100%).

Step 2: Synthesis of Compound 109.

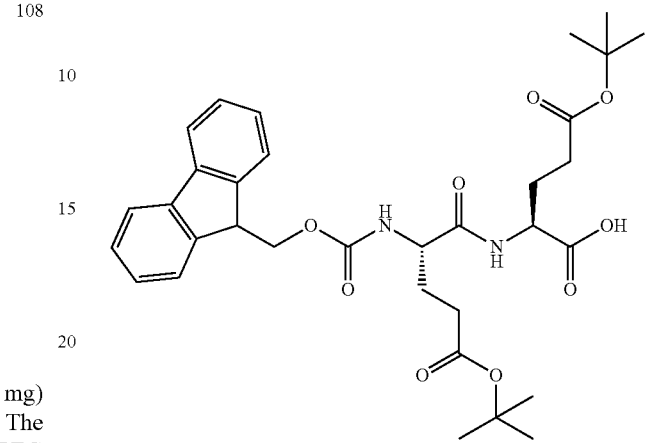

109

To a stirred solution of Fmoc-Glu(OtBu)-OH (2 g) in anhydrous DMF (18 mL) at 0° C. was added HOBt (666 mg) and DIC (768 μL). The reaction mixture was allowed to warm to RT and after 2 h, Glu(O$^t$Bu)-OH (1.19 g) and DIPEA (2.46 mL) were added. After stirring for 20 h, the reaction mixture was concentrated in vacuo and purified by reverse phase column C18-column chromatography, eluting with buffer A (v/v): water:0.05% trifluoroacetic acid and buffer B (v/v): acetonitrile:0.05% trifluoroacetic acid (100:0 v/v to 0:100 v/v) The organic solvent was removed in vacuo and the aqueous solvent removed by lyophilisation to give Fmoc-(L-Glu(O$^t$Bu))$_2$-OH, compound 109, as a white solid (1.03 g). m/z [2M+H]$^+$ (1221, 15%), [M+H]$^+$ (611, 60%), [M−$^t$Bu+H]$^+$ (554, 65%), [M−2$^t$Bu+H]$^+$ (499, 100%)).

Step 4: Synthesis of Compound 110.

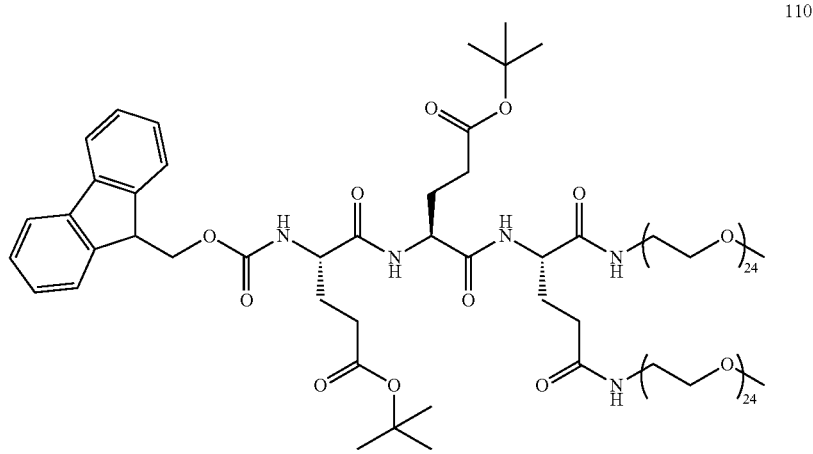

110

To a stirred solution of compound 108 (330 mg) in anhydrous DMF (10 mL) was added compound 109 (100 mg). At 0° C., HATU (156 mg) and NMM (45 μL) were then added and the resulting solution stirred for 5 min before further addition of NMM (3 μL) and HATU (11 mg). The reaction solution was allowed to stir for another 20 min before being warmed to room temperature whereupon stirring was continued for a further 4 h. After this time, additional amounts of HATU (51 mg) and NMM (15 μL) were added. After a further 1.5 h, the mixture was stored at −20° C. for 18 h before being purified by reverse phase C18-column chromatography, eluting with buffer A (v/v): water:0.05% trifluoroacetic acid and buffer B (v/v): acetonitrile:0.05% trifluoroacetic acid (100:0 v/v to 0:100 v/v). The organic solvent was removed in vacuo and the aqueous solvent removed by lyophilisation to give Fmoc-(L-Glu(O$^t$Bu))$_2$-L-Glu(PEG(24)-OMe)-PEG(24)-OMe, compound 110, as a white solid (193 mg). m/z [M+3H]$^{3+}$ (961, 20%), [M-$^t$Bu+4H]$^{4+}$ (707, 100%), [M−2$^t$Bu+4H]$^{4+}$ (693, 85%), [M+5H]$^{5+}$ (577, 75%).

Step 5: Synthesis of Compound 111.

1p;2p

111

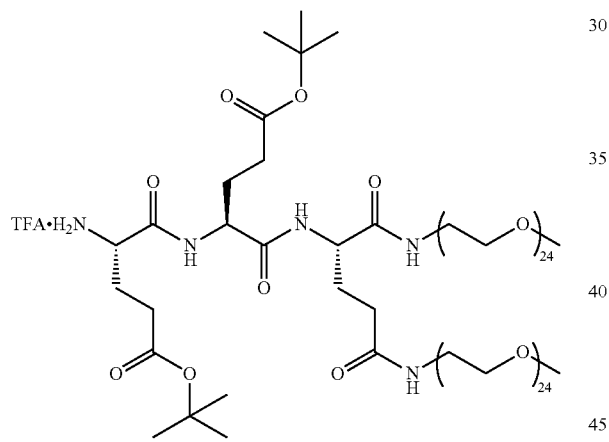

To a stirred solution of 111 (193 mg) in anhydrous DMF (1.5 mL) was added piperidine (20 μL). After 90 min, a further amount of piperidine (13 μL) was added and the reaction stirred for another 90 min before being stored at −20° C. for 18 h. The solvent was removed under high vacuum and the resulting residue triturated in hexane. The residue was further dried under high vacuum for 30 min before being dissolved in a 50:50 mixture of buffer A:buffer B (2 mL, buffer A (v/v): water:0.05% trifluoroacetic acid and buffer B (v/v): acetonitrile:0.05% trifluoroacetic acid) and lyophilised overnight to give TFA.H2N-(L-Glu(OtBu))$_2$-L-Glu(PEG(24)-OMe)-PEG(24)-OMe, compound 111, as a pale blue solid (186 mg). m/z [M+3H]$^{3+}$ (887, 20%), [M+4H]$^{4+}$ (666, 100%), [M+5H]$^{5+}$ (533, 30%).

Step 6: Synthesis of Compound 112.

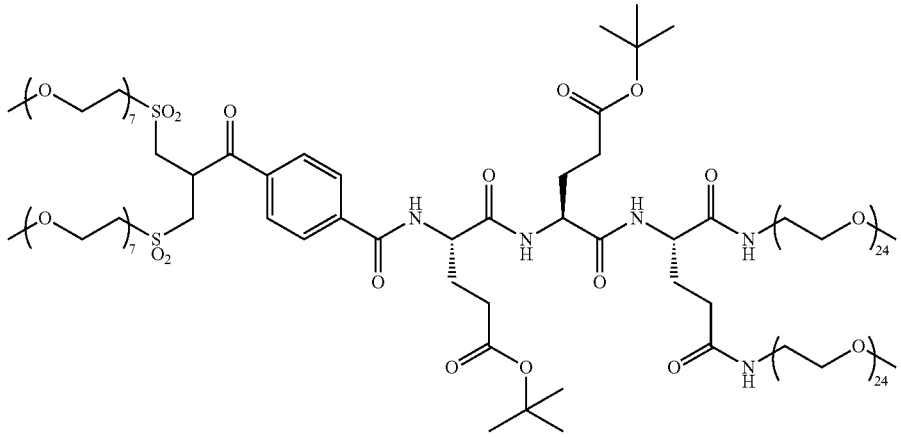

112

To a stirred solution of 4-[2,2-bis[alpha-methoxy-omega-sulfonyl hepta(ethylene glycol)]acetyl]benzoic acid (71 mg) in anhydrous DMF (1.5 mL) was added to HATU (28 mg). The mixture was cooled to 0° C. and stirred under an inert atmosphere for 30 min. A solution of 111 (186 mg) in anhydrous DMF (2.5 mL) was added, followed by HATU (22.9 mg) and NMM (14.7 µL), and the mixture allowed to warm to RT.

After 3 h, additional amounts of 4-[2,2-bis[alpha-methoxy-omega-sulfonyl hepta(ethylene glycol)]acetyl] benzoic acid (18 mg), HATU (50.8 mg) and NMM (15 µL) were added. After a further 1.5 h, further amounts of 4-[2,2-bis[alpha-methoxy-omega-sulfonyl hepta(ethylene glycol)]acetyl]benzoic acid (9 mg), HATU (51 mg) and NMM (15 µL) were added. The reaction mixture was stirred for a further 8 h and purified twice by reverse phase C18-column chromatography, eluting with buffer A (v/v): water:0.05% trifluoroacetic acid and buffer B (v/v): acetonitrile:0.05% trifluoroacetic acid (100:0 v/v to 0:100 v/v). The organic solvent was removed in vacuo and the aqueous solvent removed by lyophilisation to give 112, as a pale yellow oil (assumed quantitative). m/z [M+4H]$^{4+}$ (902, 60%), [M-$^t$Bu+4H]$^{4+}$ (888, 60%), [M-2$^t$Bu+4H]$^{4+}$ (874, 45%), [M-$^t$Bu+5H]$^{5+}$ (711, 100%).

Step 7: Synthesis of Compound 113.

Formic acid (2 mL) was added to 112 under an inert atmosphere. The reaction mixture was stirred for 60 min before being concentrated in vacuo. The material was purified by reverse phase C18-column chromatography, eluting with buffer A (v/v): water:0.05% trifluoroacetic acid and buffer B (v/v): acetonitrile:0.05% trifluoroacetic acid (100:0 v/v to 0:100 v/v). The organic solvent was removed in vacuo and the aqueous solvent removed by lyophilisation to give 113, as a colourless oil (28.1 mg). m/z [M+3H]$^{3+}$ (1165, 5%), [M+4H]$^{4+}$ (874, 65%), [M+5H]$^{5+}$ (699, 100%).

Step 7: Synthesis of Reagent 107.

To a stirred solution of 113 (15 mg) in anhydrous DMF (270 µL) was added HATU (4 mg). The mixture was cooled to 0° C. and stirred under an inert atmosphere for 20 min. A solution of val-Cit-PAB-MMAE (12 mg) in anhydrous DMF (300 µL) was added, followed by HATU (2.5 mg) and NMM (2 µL), and the mixture allowed to warm to RT. After 4 h 20 min, additional amounts of HATU (3.3 mg) and NMM (0.9 µL) were added. The reaction mixture was stirred for a further 2 h before being stored at −20° C. for 18 h. Upon warming to RT, HATU (3.3 mg) and NMM (0.9 µL) were added to the stirred solution. After a 4.5 h, additional amounts of HATU (1.6 mg) and NMM (0.5 µL) were added and the reaction allowed to stir for a further 2.5 h before being stored at −20° C. for 18 h. The material was purified by reverse phase C18-column chromatography, eluting with buffer A (v/v): water:0.05% trifluoroacetic acid and buffer B

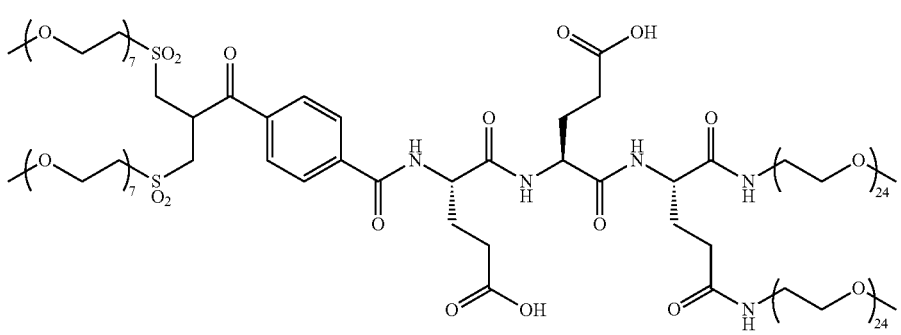

113 as a white solid (13.8 mg). m/z [M+4H]$^{4+}$ (1426, 5%), [M+5H]$^{5+}$ (1141, 70%), [M+6H]$^{6+}$ (951, 100%), [M+7H]$^{7+}$ (815, 20%).

Conjugation of Brentuximab with conjugation reagent 107 was carried out as described within Example 21 for 17 h. Results from analytical HIC show that the conversion to DAR4 product was 61%.

The invention claimed is:

1. A conjugating reagent, wherein the conjugating reagent is of the formula (Ic), (Ic'), (Id), (Id'), (Ie), (Ie'), (IIa), (IIIa) or (IIIb):

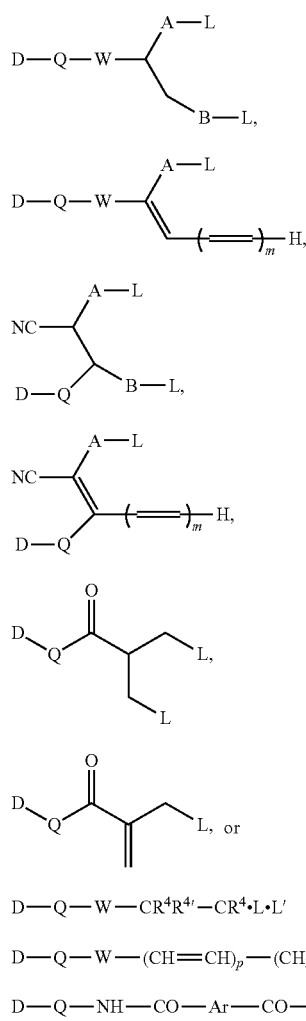

wherein:
D represents a payload which is a diagnostic, therapeutic or labelling agent or a binding agent for a diagnostic, therapeutic or labelling agent;
Q represents a linking group;
W represents an electron-withdrawing group;
A represents a $C_{1-5}$ alkylene or alkenylene chain;
B represents a bond or a $C_{1-4}$ alkylene or alkenylene chain;
Ar represents an optionally substituted aryl;
R$^4$ represents a hydrogen atom or a $C_{1-4}$alkyl group;
R$^{4'}$ represents a hydrogen atom;
p represents 0 or an integer of from 1 to 4;

each L independently represents a leaving group, at least one of which, and in cases where there are two, both include a —(CH$_2$CH$_2$O)$_n$— in which n is a number of six or more; and
L' is a leaving group which includes a —(CH$_2$CH$_2$O)$_n$— in which n is a number of six or more or is a leaving group of another structure; or
the two Ls together, or the L and L' together, represent a leaving group which includes a —(CH$_2$CH$_2$O)$_{n1}$— in which n1 is a number of two or more;
and wherein the portion —(CH$_2$CH$_2$O)$_n$— has a molecular weight of up to 5 kDa.

2. A conjugating reagent as claimed in claim 1, in which n is from 6 to 9.

3. A reagent as claimed in claim 1, in which said leaving group is of the formula —SP, —OP, —SO$_2$P, —OSO$_2$P, —N$^+$PR$^2$R$^3$, or is a group of formula —S—P—S—, —O—P—O—, —SO$_2$—P—SO$_2$—, —OSO$_2$—P—OSO$_2$—, or —N$^+$R$^2$R$^3$—P—N$^+$R$^2$R$^3$—, in which P is a group which includes a portion —(CH$_2$CH$_2$O)$_n$— and each of R$^2$ and R$^3$ independently represents a hydrogen atom or a 4alkyl group or a group P.

4. A reagent as claimed in claim 3, in which said leaving group is of the formula —SO$_2$P.

5. A reagent as claimed in claim 1, in which said leaving group includes —(CH$_2$CH$_2$O)$_n$—R$^1$ where R$^1$ is a capping group; or in which said —(CH$_2$CH$_2$O)$_n$— group has two points of attachment within the reagent.

6. A reagent as claimed in claim 1, in which said leaving group is —S—(CH$_2$CH$_2$O)$_n$—(CH$_2$CH$_2$)—S—, —O—(CH$_2$CH$_2$O)$_n$—(CH$_2$CH$_2$)—O—, —SO$_2$—(CH$_2$CH$_2$O)$_n$—(CH$_2$CH$_2$)—SO$_2$—, —OSO$_2$—(CH$_2$CH$_2$O)$_n$—(CH$_2$CH$_2$)—OSO$_2$—, —N$^+$R$^2$R$^3$—(CH$_2$CH$_2$O)$_n$—(CH$_2$CH$_2$)—N$^+$R$^2$R$^3$—, or one of the groups of formula

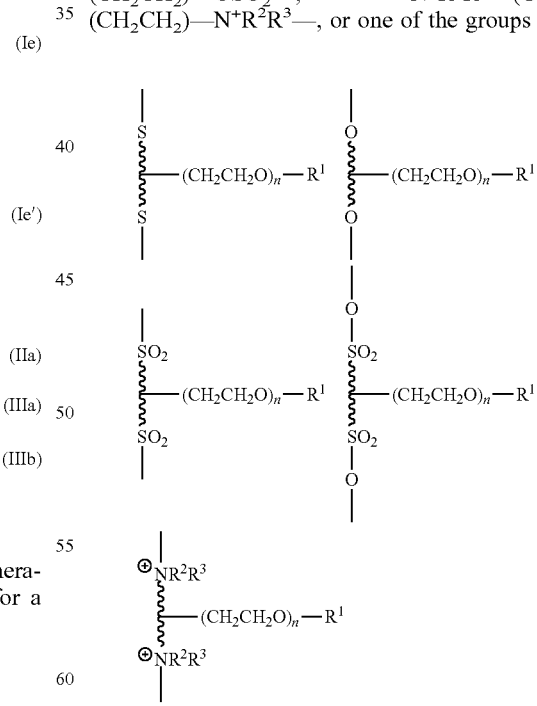

where R$^1$ is a capping group and each of R$^2$ and R$^3$ independently represents a hydrogen atom or a $C_{1-4}$ alkyl group.

7. A reagent as claimed in claim 6, in which said leaving group is —SO$_2$—(CH$_2$CH$_2$O)$_n$—(CH$_2$CH$_2$)—SO$_2$—.

8. A reagent as claimed in claim 5, in which $R^1$ represents a hydrogen atom, a $C_{1-4}$alkyl group, an optionally substituted aryl group, or a group of formula —$CH_2CH_2CO_2H$ or —$CH_2CH_2NH_2$.

9. A reagent as claimed in claim 1, in which D-Q includes a drug or a polymer or both a drug and a polymer.

10. A reagent as claimed in claim 9, in which the drug if present is a cytotoxic drug, and the polymer if present is polyethylene glycol.

11. A conjugating reagent as claimed in claim 1, in which the conjugating reagent is of formula (Ic).

12. A conjugating reagent as claimed in claim 1, in which D is a cytotoxic agent or toxin.

13. A conjugating reagent as claimed in claim 1, in which D is an auristatin or a maytansinoid.

14. A conjugating reagent as claimed in claim 1, in which Q represents a linking group containing a degradable group containing a group susceptible to enzymatic degradation.

15. A conjugating reagent as claimed in claim 1, in which Q represents a linking group containing a group of the formula:

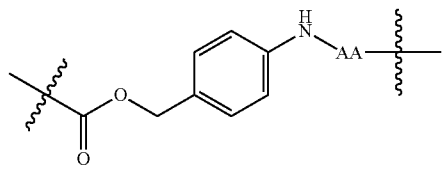

wherein AA represents a protease-specific amino acid sequence.

16. A conjugating reagent as claimed in claim 15, in which AA is Val-Cit.

17. A conjugating reagent as claimed in claim 1, in which W is a keto group.

18. A conjugating reagent as claimed in claim 1, in which A is —$CH_2$— and B is a bond.

19. A conjugating reagent as claimed in claim 1, in which Lisa group of the formula —$SO_2$—$(CH_2CH_2O)_7$—CH.

20. A process for the conjugation of a peptide or protein, which comprises reacting said peptide or protein with a conjugating reagent as claimed in claim 1.

21. A process as claimed in claim 20, in which the protein is a receptor or ligand binding protein or an antibody or antibody fragment.

* * * * *

UNITED STATES PATENT AND TRADEMARK OFFICE
CERTIFICATE OF CORRECTION

PATENT NO. : 10,835,616 B2
APPLICATION NO. : 15/517971
DATED : November 17, 2020
INVENTOR(S) : Godwin et al.

Page 1 of 1

It is certified that error appears in the above-identified patent and that said Letters Patent is hereby corrected as shown below:

In the Claims

Claim 3, Column 130, Line 22, "4alkyl" should read -- $C_{1-4}$alkyl --

Claim 19, Column 132, Line 18, "Lisa" should read -- L is a --

Signed and Sealed this
Second Day of February, 2021

Drew Hirshfeld
*Performing the Functions and Duties of the*
*Under Secretary of Commerce for Intellectual Property and*
*Director of the United States Patent and Trademark Office*